US008044242B2

(12) United States Patent
Nirschl et al.

(10) Patent No.: US 8,044,242 B2
(45) Date of Patent: Oct. 25, 2011

(54) 2-(ARYLOXY) ACETAMIDE FACTOR VIIA INHIBITORS USEFUL AS ANTICOAGULANTS

(75) Inventors: Alexandra A. Nirschl, Yardley, PA (US); Xiaojun Zhang, Furlong, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 468 days.

(21) Appl. No.: 12/282,178

(22) PCT Filed: Mar. 8, 2007

(86) PCT No.: PCT/US2007/063524
§ 371 (c)(1),
(2), (4) Date: Dec. 17, 2008

(87) PCT Pub. No.: WO2007/103996
PCT Pub. Date: Sep. 13, 2007

(65) Prior Publication Data
US 2009/0131473 A1 May 21, 2009

Related U.S. Application Data

(60) Provisional application No. 60/780,610, filed on Mar. 9, 2006.

(51) Int. Cl.
*C07C 213/00* (2006.01)
*C07D 237/30* (2006.01)
*C07D 217/00* (2006.01)
*C07D 513/02* (2006.01)

(52) U.S. Cl. ......... 564/170; 544/237; 546/113; 546/139

(58) Field of Classification Search ........................ None
See application file for complete search history.

(56) References Cited

U.S. PATENT DOCUMENTS

| | | | |
|---|---|---|---|
| 5,023,236 A | 6/1991 | Edgington et al. |
| 5,583,147 A | 12/1996 | Ko et al. |
| 5,843,442 A | 12/1998 | Soule et al. |
| 5,866,542 A | 2/1999 | Vlasuk et al. |
| 6,140,353 A | 10/2000 | Ackermann et al. |
| 6,638,980 B1 | 10/2003 | Su et al. |
| 6,946,489 B2 | 9/2005 | Juraszyk et al. |
| 7,273,867 B2 | 9/2007 | Dorsch et al. |
| 2002/0004608 A1 | 1/2002 | Alig et al. |
| 2003/0135055 A1 | 7/2003 | Dorsch et al. |

OTHER PUBLICATIONS

Arnold, C. Shane, et al., "The antithrombotic and anti-inflammatory effects of BCX-3607, a small molecule tissue factor/factor VIIa inhibitor", Thrombosis Research, vol. 117, pp. 343-349 (2006).
Carson, S.D. et al., "The role of tissue factor in the production of thrombin", Blood Coagulation and Fibrinolysis, vol. 4, pp. 281-292 (1993).
Frédérick, R. et al., "Modulators of the Coagulation Cascade: Focus and Recent Advances in Inhibitors of Tissue Factor, Factor VIIa and their Complex", Current Medicinal Chemistry, vol. 12, pp. 397-417 (2005).
Giesen, P. et al., "Blood-borne tissue factor: Another view of thrombosis", PNAS, vol. 96, pp. 2311-2315 (1999).
Girard, T. et al., "The role of tissue factor/factor VIIa in the pathophysiology of acute thrombotic formation", Current Opinion in Pharmacology, vol. 1, pp. 159-163 (2001).
Himber, J. et al., "Inhibition of tissue factor limits the growth of venous thrombus in the rabbit", J. of Thrombosis and Haemostasis, vol. 1, pp. 889-895 (2003).
Hirsh, J. et al., "New anticoagulants", Blood, vol. 105, pp. 453-463 (2005).
Hoffman, M., "A cell-based model of coagulation and the role of factor VIIa", Blood reviews, vol. 17, pp. S1-S5 (2003).
Lazarus, R. et al., "Inhibitors of Tissue Factor Factor VIIa for Anticoagulant Therapy", Current Medicinal Chemistry, vol. 11, pp. 2275-2290 (2004).
Lee, A. et al., "Dose-Response Study of Recombinant Factor VIIa/Tissue Factor Inhibitor Recombinant Nematode Anticoagulant Protein c2 in Prevention of Postoperative Venous Thromboembolism in Patients Undergoing Total Knee Replacement", Circulation, vol. 104, pp. 74-78 (2001).
Moons, A. et al., "Recombinant Nematode Anticoagulant Protein c2, an Inhibitor of the Tissue Factor/Factor VIIa Complex, in Patients Undergoing Elective Coronary Angioplasty", J. of the American College of Cardiology, vol. 41(12), pp. 2147-2153 (2003).
Morrissey, J.H., "Tissue factor: in at the start . . . and the finish?", J. of Thrombosis and Haemostasis, vol. 1, pp. 878-880 (2003).
Morrissey, J.H., "Quantitation of Activated Factor VII Levels in Plasma Using a Tissue Factor Mutant Selectively Deficient in Promoting Factor VII Activation", Blood, vol. 81, pp. 734-744 (1993).
Olivero, A. et al., "A Selective, Slow Binding Inhibitor of Factor VIIa Binds to a Nonstandard Active Site Conformation and Attenuates Thrombus Formation in Vivo*", The J. of Biological Chemistry, vol. 280(10), pp. 9160-9169 (2005).
Suleymanov, O. et al., "Pharmacological Interruption of Acute Thrombus Formation with Minimal Hemorrhagic Complications by a Small Molecule Tissue Factor/Factor VIIa Inhibitor: Comparison to Factor Xa and Thrombin Inhibition in a Nonhuman Primate Thrombosis Model", The J. of Pharmacology and Experimental Therapeutics, vol. 306(3), pp. 1115-1121 (2003).

(Continued)

Primary Examiner — Janet Andres
Assistant Examiner — Heidi Reese
(74) Attorney, Agent, or Firm — Jing G. Sun

(57) ABSTRACT

The present invention relates generally to novel 2-(aryloxy) acetamides of Formula (I):

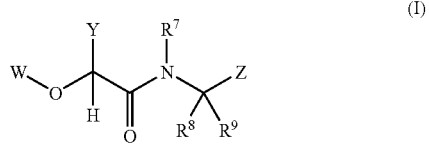

(I)

or stereoisomers, tautomers, pharmaceutically acceptable salts, solvates, or prodrugs thereof, wherein the variables W, Y, Z, $R^7$, $R^8$, and $R^9$ are as defined herein. These compounds are selective inhibitors of the serine protease coagulation factor VIIa which can be used as medicaments.

17 Claims, No Drawings

OTHER PUBLICATIONS

Szalony, J. et al., "Administration of a small molecule tissue factor/Factor VIIa inhibitor in a non-human primate thrombosis model of venous thrombosis: effects on thrombus formation and bleeding time", Thrombosis Research, vol. 112, pp. 167-174 (2003).

Szalony, J. et al., "Pharmacological Intervention at Disparate Sites in the Coagulation Cascade: Comparison of Anti-thrombotic Efficacy vs. Bleeding Propensity in a Rat Model of Acute Arterial Thrombosis", J. of Thrombosis and Thrombolysis, vol. 14(2), pp. 113-121 (2002).

Young, W. et al., "Factor VIIa inhibitors: Chemical optimization, preclinical pharmacokinetics, pharmacodynamics, and efficacy in an arterial baboon thrombosis model", Bioorganic & Medicinal Chemistry Letters, vol. 16, pp. 2037-2041 (2006).

Zbinden, K. et al., "Dose-dependent antithrombotic activity of an orally active tissue factor/factor VIIa inhibitor without concomitant enhancement of bleeding propensity", Bioorganic & Medicinal Chemistry Letters, vol. 14, pp. 5357-5369 (2006).

Zbinden, K. et al., "Design of selective phenylglycine amide tissue factor/factor VIIa inhibitors", Bioorganic & Medicinal Chemistry Letters, vol. 15(3), pp. 817-822 (2004).

US 8,044,242 B2

2-(ARYLOXY) ACETAMIDE FACTOR VIIA INHIBITORS USEFUL AS ANTICOAGULANTS

CROSS-REFERENCE TO RELATED APPLICATIONS

This application is a 371 application of PCT/US2007/063524 filed Mar. 8, 2007, which claims priority benefit of U.S. provisional application Ser. No. 60/780,610, filed Mar. 9, 2006, which is incorporated by reference herein.

FIELD OF THE INVENTION

The present invention provides novel 2-(aryloxy)acetamides, and analogues thereof, which are selective inhibitors of the serine protease coagulation factor VIIa. This invention also relates to pharmaceutical compositions comprising these compounds and methods of using the same.

BACKGROUND OF THE INVENTION

Factor VII is a plasma serine protease involved in the initiation of the coagulation cascade. It is present in human blood at a concentration of approximately 500 ng/mL, with about 1% of the total amount in the proteolytically active form factor VIIa (Morrissey, J. H. et al. *Blood* 1993, 81, 734-744). Factor VIIa binds with high affinity to its cofactor, tissue factor, in the presence of calcium ions to form a complex with enhanced proteolytic activity (Carson, S. D. and Brozna, J. P. *Blood Coag. Fibrinol.* 1993, 4, 281-292). Tissue factor is normally expressed in cells surrounding the vasculature, and is exposed to factor VIIa in blood by vessel injury or atherosclerotic plaque rupture. Once formed, the tissue factor/factor VIIa complex initiates blood coagulation by proteolytic cleavage of factor X to factor Xa, factor IX to factor IXa and autoactivation of additional factor VII to VIIa. Factor Xa, generated either directly by tissue factor/factor VIIa or indirectly through action of factor IXa, catalyzes the conversion of prothrombin to thrombin. Thrombin converts fibrinogen to fibrin, which polymerizes to form the structural framework of a blood clot, and activates platelets, which are a key cellular component of coagulation (Hoffman, M. *Blood Reviews* 2003, 17, S1-S5). In addition, there is evidence that tissue factor is present in blood, likely in an encrypted form that is de-encrypted during clot formation. (Giesen, P. L. A. et al. *Proc. Natl. Acad. Sci.* 1999, 96, 2311-2315; Himber, J. et al. *J. Thromb. Haemost.* 2003, 1, 889-895). The tissue factor/factor VIIa complex derived from blood borne tissue factor may play an important role in propagation of the coagulation cascade (clot growth) and in thrombus formation in the absence of vessel wall injury (i.e., stasis induced deep vein thrombosis or sepsis). The source of blood borne tissue factor is an area of active research (Morrissey, J. H. *J. Thromb. Haemost.* 2003, 1, 878-880).

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thrombotic or thromboembolic disorders and include acute coronary syndrome, unstable angina, myocardial infarction, ischemic stroke, deep vein thrombosis, peripheral occlusive arterial disease, transient ischemic attack, and pulmonary embolism. In addition, thrombosis occurs on artificial surfaces in contact with blood, including catheters and artificial heart valves. Therefore, drugs that inhibit blood coagulation, or anticoagulants, are "pivotal agents for prevention and treatment of thromboembolic disorders" (Hirsh, J. et al. *Blood* 2005, 105, 453-463).

Because of its key role in the coagulation cascade, researchers have postulated that inhibition of factor VIIa could be used to treat or prevent thrombotic or thromboembolic disease. (Girard, T. J.; Nicholson, N. S. *Curr. Opin. Pharmacol.* 2001, 1, 159-163; Lazarus, R. A., et al. *Curr. Med. Chem.* 2004, 11, 2275-2290; Frederick, R. et al. *Curr. Med. Chem.* 2005, 12, 397-417.) Several studies have confirmed that various biological and small molecule inhibitors of factor VIIa have in vivo antithrombotic efficacy with a low bleeding liability. For instance, it has been demonstrated that a biological factor VIIa inhibitor XK1, comprising a hybrid of Factor X light chain and tissue factor pathway inhibitor first kunitz domain, prevents thrombus formation in a rat model of arterial thrombosis, with no change in bleeding time or total blood loss (Szalony, J. A. et al. *J. Thrombosis and Thrombolysis* 2002, 14, 113-121). In addition, small molecule active site directed factor VIIa inhibitors have demonstrated antithrombotic efficacy in animal models of arterial thrombosis (Suleymanov, O., et al. *J Pharmacology and Experimental Therapeutics* 2003, 306, 1115-1121; Olivero, A. G. et al. *J. Biol. Chem.* 2005, 280, 9160-9169; Young, W. B., et al. *Bioorg. Med. Chem. Lett.* 2006, 16, 2037-2041; Zbinden, K. G. et al. *Bioorg. Med. Chem.* 2006, 14, 5357-5369) and venous thrombosis (Szalony, J. A., et al. Thrombosis Research 2003, 112, 167-174; Arnold, C. S., et al. *Thrombosis Research* 2006, 117, 343-349), with little impact on bleeding time or blood loss. Moreover, the biological factor VIIa inhibitor recombinant nematode anticoagulant protein c2 (rNAPc2) is currently under clinical investigation for treatment of acute coronary syndromes. Results of initial clinical trials demonstrate that rNAPc2 prevents deep vein thrombosis in patients undergoing total knee replacement (Lee, A., et al. *Circulation* 2001, 104, 74-78), reduces systemic thrombin generation in patients undergoing coronary angioplasty (Moons, A. H. M. *J. Am. Coll. Cardiol.* 2003, 41, 2147-2153), and reduces magnitude and duration of ischemic events in patients with acute coronary syndromes (Giugliano, R. P. et al. World Congress of Cardiology 2006, Barcelona, Poster #3897).

Work has accordingly been performed to identify and optimize factor VIIa inhibitors. For example, U.S. Pat. No. 5,866,542 describes recombinant nematode anticoagulant proteins which inhibit factor VIIa. U.S. Pat. No. 5,843,442 discloses monoclonal antibodies or antibody fragments possessing factor VIIa inhibitory activity, and U.S. Pat. No. 5,023,236 presents tripeptides and tripeptide derivatives that inhibit factor VIIa.

While a number of factor VIIa inhibitors have been discussed in the art, improved inhibitors, especially non-peptide inhibitors, of serine proteases for the treatment of thromboembolic disorders are always desirable. The present invention discloses 2-(aryloxy)acetamides and analogues thereof as inhibitors of coagulation factor VIIa and, as such, their utility in the treatment of thromboembolic disorders.

In addition, it is also desirable to find new compounds with improved pharmacological characteristics compared with known serine protease inhibitors. For example, it is preferred to find new compounds with improved factor VIIa inhibitory activity and improved selectivity for factor VIIa versus other serine proteases. Also, it is preferred to find new compounds with improved activity in in vitro clotting assays, such as the prothrombin time (PT) assay. (for a description of the PT assay see, Goodnight, S. H.; Hathaway, W. E. Screening Tests of Hemostasis. *Disorders of Thrombosis and Hemostasis: a clinical guide*, 2$^{nd}$ edition, McGraw-Hill: New York, 2001 pp. 41-51). It is also desirable and preferable to find compounds with advantageous and improved characteristics in one or more of the following categories, which are given as examples and are not intended to be limiting: (a) pharmacokinetic properties, including oral bioavailability, half life, and clearance; (b) pharmaceutical properties; (c) dosage requirements; (d) factors which decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

SUMMARY OF THE INVENTION

The present invention provides 2-(aryloxy)acetamides, and analogues thereof, which are useful as selective inhibitors of serine protease enzymes, especially factor VIIa, including stereoisomers, tautomers, stereoisomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for modulation of the coagulation cascade comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating thrombotic or thromboembolic disorders comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of a thromboembolic disorder.

These and other features of the invention will be set forth in the expanded form as the disclosure continues.

DETAILED DESCRIPTION OF THE INVENTION

In a first aspect, the present invention provides, inter alia, a compound of Formula (I):

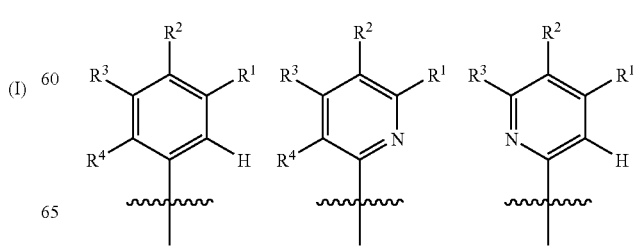

or stereoisomers, tautomers, pharmaceutically acceptable salts, solvates, or prodrugs thereof, wherein:

W is substituted with 0-2 $R^6$ and selected from:

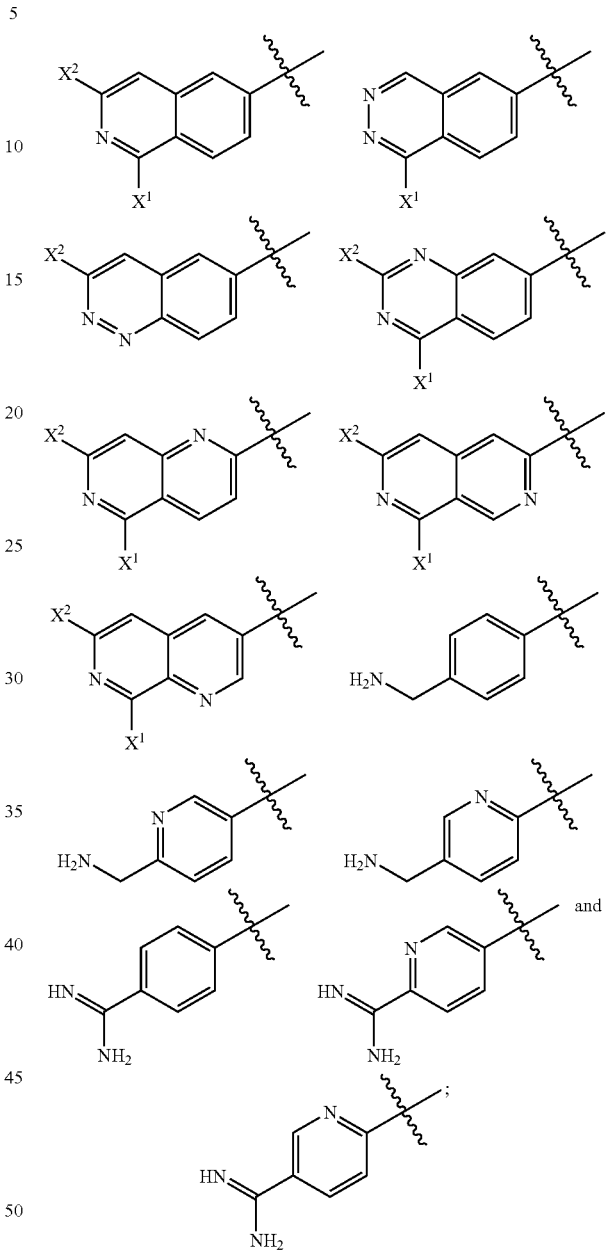

$X^1$ and $X^2$ are, independently at each, H or $NH_2$;

Y is selected from:

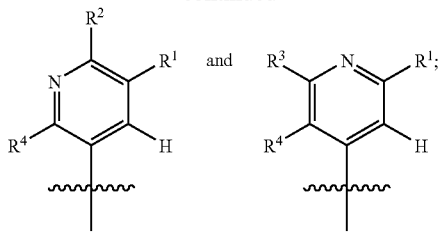

Z is phenyl substituted with 0-3 $R^{10}$, naphthyl substituted with 0-3 $R^{10}$, or a 5- to 10-membered heterocycle comprising: carbon atoms and 1-4 heteroatoms selected from N, $NR^c$, O, and $S(O)_p$, wherein said heterocycle is substituted with 0-3 $R^{11}$;

$R^1$ is, independently at each occurrence, H, F, Cl, Br, I, $C_{1-5}$ alkyl substituted with 0-1 OH, $C_{1-5}$ haloalkyl, $C_{2-5}$ alkenyl, $C_{2-5}$ alkynyl, —O—$C_{1-5}$ alkyl, —O—$C_{1-5}$ haloalkyl, —S—$C_{1-5}$ alkyl, or $C_{3-6}$ cycloalkyl;

$R^2$ and $R^3$ are, independently at each occurrence, H, F, Cl, Br, I, $OR^a$, $SR^a$, $OCF_3$, $OCHF_2$, $OCH_2F$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle is substituted with 0-3 $R^f$;

$R^4$ is, independently at each occurrence, H, F, Cl, Br, I, $OR^a$, $SR^a$, $OCF_3$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle are substituted with 0-3 $R^f$;

alternatively, $R^2$ and $R^3$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

alternatively, $R^3$ and $R^4$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

$R^6$ is, independently at each, F, Cl, Br, I, CN, OH, $CF_3$, $C_{1-4}$ alkyl, $C_{1-4}$ haloalkyl, or $C_{1-4}$ alkoxy;

$R^7$ is H, $C_{1-4}$ alkyl, —$CH_2CO_2R^a$, —$CH_2CH_2CO_2R^a$, —$CH_2CH_2OH$, or —$CH_2CH_2CH_2OH$, tetrazolyl, —$CH_2CONHSO_2R^e$, or —$CH_2CH_2CONHSO_2R^e$;

$R^8$ is H, CN, —$CO_2R^a$, —$C(O)NR^cR^d$, tetrazolyl, or $C_{1-4}$ alkyl substituted with 0-2 $R^{8a}$;

$R^{8a}$ is, independently at each, =O, $OR^a$, F, Cl, Br, I, CN, $NO_2$, —$OCF_3$, —$NR^bR^c$, —$C(O)R^a$, —$CO_2R^a$, —$OC(O)R^a$, —$OC(O)NR^cR^d$, —$NR^dC(O)R^a$, —$C(O)NR^cR^d$, —$NR^cC(O)NR^cR^d$, $NR^cC(O)OR^a$, —$SO_2NR^cR^d$, —$NR^cSO_2R^i$, —$NR^cSO_2NR^cR^d$, —$SO_2NHC(O)R^a$, —$C(O)NHSO_2R^a$, —$NR^cSO_2CF_3$, —$SO_2CF_3$, —$S(O)_pR^i$, —$(CF_2)_rCF_3$, tetrazole, $C_{3-6}$ cycloalkyl substituted with 0-3 $R^f$, phenyl substituted with 0-3 $R^f$, or 5- to 6-membered heterocycle comprising: carbon atoms and 1-4 heteroatoms selected from N, $NR^c$, O, and $S(O)_p$, wherein said heterocycle is substituted with 0-3 $R^f$;

alternatively, $R^8$ and $R^9$ can be taken together with the carbon atom to which they are attached to form a 3- to 5-membered carbocycle;

$R^9$ is H or $C_{1-4}$ alkyl;

$R^{10}$ is, independently at each occurrence, F, Cl, Br, I, —$(CH_2)_r$—$OR^a$, $SR^a$, $OCF_3$, $SCF_3$, CN, $NO_2$, —$B(OH)_2$, —$(CH_2)_r$—$NR^bR^c$, —$C(O)R^a$, —$(CH_2)_r$—$CO_2R^a$, —$(CH_2)_r$—$NR^cCO_2R^a$, —$NR^dC(O)R^a$, —$(CH_2)_r$—$C(O)NR^cR^d$, —$NR^cC(O)NR^cR^d$, —$SO_2NR^cR^d$, —$OSO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, or —$(CH_2)_r$-5- to 10-membered heterocycle comprising: carbon atoms and 1-4 heteroatoms selected from N, $NR^c$, O, and $S(O)_p$, wherein said heterocycle are substituted with 0-3 $R^f$;

alternatively, when two $R^{10}$ groups are substituted on adjacent ring atoms, they can be taken together with the ring atoms to which they are attached to form a 5- to 7-membered carbocycle or heterocycle comprising: carbon atoms and 0-4 heteroatoms selected from N, O, and $S(O)_p$, wherein said carbocycle or heterocycle is substituted with 0-2 $R^i$;

$R^{11}$ is, independently at each occurrence, =O, F, Cl, Br, I, —$(CH_2)_r$—$OR^a$, $SR^a$, $OCF_3$, $SCF_3$, CN, $NO_2$, —$B(OH)_2$, —$(CH_2)_r$—$NR^bR^c$, —$C(O)R^a$, —$(CH_2)_r$—$CO_2R^a$, —$(CH_2)_r$—$NR^cCO_2R^a$, —$NR^dC(O)R^a$, —$(CH_2)_r$—$C(O)NR^cR^d$, —$NR^cC(O)NR^cR^d$, —$SO_2NR^cR^d$, —$OSO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$, —$(CH_2)_r$—$C_{3-10}$ carbocycle substituted with 0-3 $R^f$, or —$(CH_2)_r$-5- to 10-membered heterocycle comprising: carbon atoms and 1-4 heteroatoms selected from N, $NR^c$, O, and $S(O)_p$, wherein said heterocycle are substituted with 0-3 $R^f$;

$R^a$ is, independently at each, H, $C_{1-6}$ alkyl substituted with 0-4 $R^h$, —$(CH_2)_r$—$C_{3-7}$ carbocycle substituted with 0-4 $R^f$, or —$(CH_2)_r$-5- to 10-membered heterocycle comprising: carbon atoms and 1-4 heteroatoms selected from N, $NR^g$, O, and $S(O)_p$, wherein said heteroaryl is substituted with 0-4 $R^f$;

$R^b$ is, independently at each, H, $C_{1-6}$ alkyl, —$(CH_2)_n$-phenyl, $(C_{1-6}$ alkyl)C(O)—, $(C_{3-6}$ cycloalkyl)-$C_{0-4}$ alkyl-C(O)—, $(C_{6-10}$ aryl)-$C_{0-4}$ alkyl)-C(O)—, (5- to 10-membered heteroaryl)-$C_{0-4}$ alkyl-C(O)—, $(C_{1-6}$ alkyl)-NHC(O)—, $(C_{1-6}$ alkyl)$_2$-NHC(O)—, $(C_{6-10}$ aryl)-$C_{0-4}$ alkyl-NHC(O)—, (5- to 10-membered heteroaryl)-$C_{0-4}$ alkyl-NHC(O)—, $(C_{1-6}$ alkyl)-$SO_2$—, $(C_{6-10}$ aryl)-$C_{0-4}$ alkyl-$SO_2$—, or (5- to 10-membered heteroaryl)-$C_{0-4}$ alkyl-$SO_2$—, wherein said phenyl, aryl and heteroaryl are substituted with 0-2 $R^f$;

$R^c$ is, independently at each, H, $C_{1-6}$ alkyl substituted with 0-3 $R^h$, —$(CH_2)_n$—$C_{3-7}$ cycloalkyl substituted with 0-3 $R^h$, or —$(CH_2)_n$-phenyl substituted with 0-3 $R^h$;

alternatively, $R^b$ and $R^c$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^d$ is, independently at each, H, $C_{1-6}$ alkyl, —$(CH_2)_r$—$C_{3-10}$ carbocycle substituted with 0-3 $R^f$, or a —$(CH_2)_r$-5- to 12-membered heterocycle comprising: carbon atoms and 1-4 heteroatoms selected from N, $NR^g$, O, and $S(O)_p$, wherein said heterocycle is substituted with 0-3 $R^f$;

alternatively, $R^c$ and $R^d$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^e$ is, independently at each, =O, $OR^a$, F, Cl, Br, I, CN, $NO_2$, $-SR^a$, $-OCF_3$, $-NR^bR^c$, $-C(O)R^a$, $-CO_2R^a$, $-NR^dC(O)R^a$, $-C(O)NR^cR^d$, $-OC(O)R^a$, $-NR^dC(O)OR^a$, $-NR^dC(O)NR^cR^d$, $-OC(O)NR^cR^d$, $-SO_2NR^cR^d$, $-NC(O)OR^a$, $-NR^cSO_2NR^cR^d$, $-NR^cSO_2R^i$, $-NR^cSO_2CF_3$, $-SO_2CF_3$, $-S(O)_pR^i$, $-(CF_2)_rCF_3$, $C_{3-10}$ carbocycle substituted with 0-3 $R^f$, or a 5- to 12-membered heterocycle comprising: carbon atoms and 1-4 heteroatoms selected from N, $NR^g$, O, and $S(O)_p$, wherein said heterocycle is substituted with 0-3 $R^f$;

$R^f$ is, independently at each, =O, $OR^a$, F, Cl, Br, I, CN, $NO_2$, $-SR^a$, $-OCF_3$, $-NR^cR^c$, $-C(O)R^a$, $-CO_2R^a$, $-NR^cC(O)R^a$, $-C(O)NR^cR^c$, $-OC(O)R^a$, $-NR^cC(O)OR^a$, $-NR^cC(O)NR^cR^c$, $-OC(O)NR^cR^c$, $-SO_2NR^cR^c$, $-NR^cSO_2NR^cR^c$, $-NR^cSO_2R^i$, $-NR^cSO_2CF_3$, $-SO_2CF_3$, $-S(O)_pR^i$, $-(CF_2)_rCF_3$, $C_{1-6}$ alkyl, $C_{2-6}$ alkenyl, $C_{2-6}$ alkynyl, $C_{3-10}$ carbocycle substituted with 0-3 $R^h$, or a 5- to 12-membered heterocycle comprising: carbon atoms and 1-4 heteroatoms selected from N, $NR^g$, O, and $S(O)_p$, and substituted with 0-3 $R^h$;

$R^g$ is, independently at each, H, $C_{1-6}$ alkyl, or $-(CH_2)_n$-phenyl;

$R^h$ is, independently at each, =O, $-(CH_2)_rOR^g$, F, Cl, Br, I, CN, $NO_2$, $-OCF_3$, $-NR^gR^g$, $-C(O)R^g$, $-CO_2R^g$, $-NR^gC(O)R^g$, $-C(O)NR^gR^g$, $-SO_2NR^gR^g$, $-NR^gSO_2NR^gR^g$, $-NR^gSO_2-C_{1-4}$ alkyl, $-NR^gSO_2CF_3$, $-NR^gSO_2$-phenyl, $-SO_2CF_3$, $-S(O)_p-C_{1-4}$ alkyl, $-S(O)_p$-phenyl, $-(CF_2)_rCF_3$, $C_{1-6}$ alkyl, $C_{2-6}$ alkenyl, $C_{2-6}$ alkynyl, $(C_{1-6}$ alkyl$)C(O)$—, $(C_{3-6}$ cycloalkyl$)-C_{0-4}$ alkyl-C(O)—, $(C_{6-10}$ aryl$)-(C_{0-4}$ alkyl$)-C(O)$—, (5-10 membered heteroaryl$)-C_{0-4}$ alkyl-C(O)—, $(C_{1-6}$ alkyl$)$-NHC(O)—, $(C_{1-6}$ alkyl$)_2$-NHC(O)—, $(C_{6-10}$ aryl$)-C_{0-4}$ alkyl-NHC(O)—, (5-10 membered heteroaryl$)-C_{0-4}$ alkyl-NHC(O)—, $(C_{1-6}$ alkyl$)-SO_2$—, $(C_{6-10}$ aryl$)-C_{0-4}$ alkyl-$SO_2$—, (5-10 membered heteroaryl$)-C_{0-4}$ alkyl-$SO_2$—, $-(CH_2)_r-C_{3-10}$ carbocycle, or a $-(CH_2)_r$-5- to 12-membered heterocycle comprising: carbon atoms and 1-4 heteroatoms selected from N, $NR^g$, O, and $S(O)_p$;

$R^i$ is, independently at each, H, $C_{1-6}$ alkyl substituted with 0-3 $R^h$, $C_{3-6}$ cycloalkyl substituted with 0-3 $R^h$, $-(CH_2)_n$-phenyl substituted with 0-3 $R^h$, $-(CH_2)_r$-5- to 10-membered heterocycle comprising: carbon atoms and 1-4 heteroatoms selected from N, $NR^g$, O, and $S(O)_p$, wherein said heterocycle is substituted with 0-3 $R^h$;

n, at each, is selected from 0, 1, 2, 3, and 4;

p, at each, is selected from 0, 1, and 2; and r, at each, is selected from 0, 1, 2, 3, and 4;

provided that when $R^8$ and $R^9$ are both H, then Z is other than unsubstituted phenyl.

In a second aspect, the present invention includes the compounds of Formula (I) or a stereoisomer, tautomer, pharmaceutically acceptable salt, solvate, or prodrug thereof, wherein:

W is substituted with 0-2 $R^6$ and selected from:

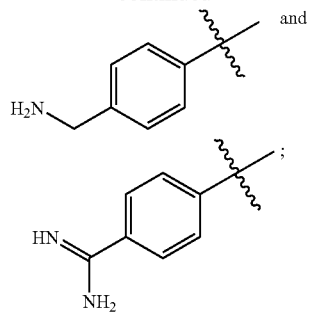

$R^1$ is, independently at each occurrence, H, F, Cl, Br, $C_{1-3}$ alkyl substituted with 0-1 OH, $C_{1-3}$ haloalkyl, $C_{2-3}$ alkenyl, $C_{2-3}$ alkynyl, —O—$C_{1-3}$ alkyl, or $C_{3-6}$ cycloalkyl;

$R^2$ and $R^3$ are, independently at each occurrence, H, F, Cl, Br, I, $OR^a$, $SR^a$, $OCF_3$, $OCHF_2$, $OCH_2F$, CN, $NO_2$, $-NR^bR^c$, $-C(O)R^a$, $-CO_2R^a$, $-NR^dC(O)R^a$, $-C(O)NR^cR^d$, $-NR^cC(O)OR^a$, $-NR^cC(O)NR^cR^d$, $-SO_2NR^cR^d$, $-NR^cSO_2NR^cR^d$, $-NR^cSO_2R^i$, $-NR^cSO_2CF_3$, $-SO_2CF_3$, $-S(O)_pR^i$, $-(CF_2)_rCF_3$, $C_{1-4}$ alkyl substituted with 0-2 $R^e$, $C_{2-4}$ alkenyl substituted with 0-2 $R^e$, or $C_{2-4}$ alkynyl substituted with 0-2 $R^e$;

$R^4$ is, independently at each occurrence, H, F, Cl, Br, I, $OR^a$, $SR^a$, $OCF_3$, CN, $NO_2$, $-NR^bR^c$, $-C(O)R^a$, $-CO_2R^a$, $-NR^dC(O)R^a$, $-C(O)NR^cR^d$, $-NR^cC(O)OR^a$, $-NR^cC(O)NR^cR^d$, $-SO_2NR^cR^d$, $-NR^cSO_2NR^cR^d$, $-NR^cSO_2R^i$, $-NR^cSO_2CF_3$, $-SO_2CF_3$, $-S(O)_pR^i$, $-(CF_2)_rCF_3$, $C_{1-4}$ alkyl substituted with 0-2 $R^e$, $C_{2-4}$ alkenyl substituted with 0-2 $R^e$, or $C_{2-4}$ alkynyl substituted with 0-2 $R^e$; and Z is phenyl substituted with 0-3 $R^{10}$, naphthyl substituted with 0-3 $R^{10}$, or a heterocycle substituted with 0-3 $R^{11}$ and selected from: furyl, thienyl, thiazolyl, imidazolyl, pyrazolyl, pyridyl, dihydroindolyl, indolyl, or 2,3-dihydro-1,4-benzodioxinyl.

In a third embodiment, the present invention includes a compound of Formula (II):

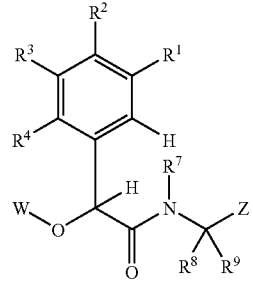

(II)

or a stereoisomer, tautomer, pharmaceutically acceptable salt, solvate, or prodrug thereof, wherein:

W is substituted with 0-2 $R^6$ and selected from:

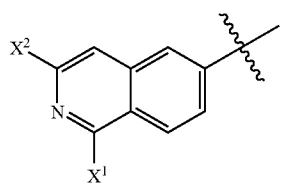
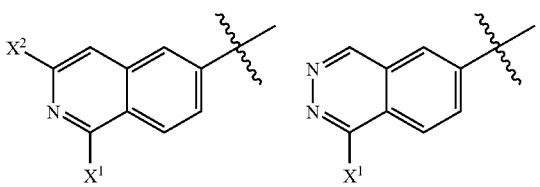

-continued

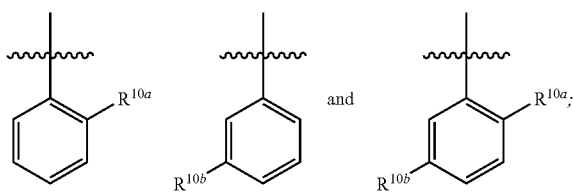

$X^1$ and $X^2$ are, independently at each occurrence, H or $NH_2$;

Z is selected from:

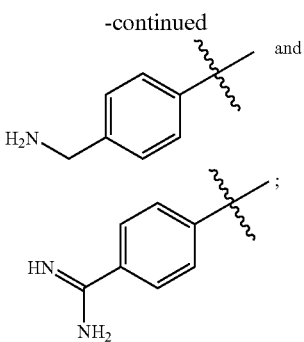

$R^1$ is H, F, Cl, Br, $C_{1-3}$ alkyl substituted with 0-1 OH, $C_{1-3}$ haloalkyl, $C_{2-3}$ alkenyl, $C_{2-3}$ alkynyl, —O—$C_{1-3}$ alkyl, or $C_{3-6}$ cycloalkyl;

$R^2$ and $R^3$ are, independently at each occurrence, H, F, Cl, Br, I, $OR^a$, $SR^a$, $OCF_3$, $OCHF_2$, $OCH_2F$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-4}$ alkyl substituted with 0-2 $R^e$, $C_{2-4}$ alkenyl substituted with 0-2 $R^e$, or $C_{2-4}$ alkynyl substituted with 0-2 $R^e$;

$R^4$ is, independently at each occurrence, H, F, Cl, Br, I, $OR^a$, $SR^a$, $OCF_3$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-4}$ alkyl substituted with 0-2 $R^e$, $C_{2-4}$ alkenyl substituted with 0-2 $R^e$, or $C_{2-4}$ alkynyl substituted with 0-2 $R^e$;

alternatively, $R^2$ and $R^3$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

alternatively, $R^3$ and $R^4$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

$R^6$ is, independently at each, F, Cl, $CH_3$, OH or $CF_3$;

$R^7$ is H, $C_{1-4}$ alkyl, —$CH_2CO_2R^a$, —$CH_2CH_2CO_2R^a$, —$CH_2CH_2OH$, —$CH_2CH_2CH_2OH$, tetrazolyl, —$CH_2CONHSO_2R^e$, or —$CH_2CH_2CONHSO_2R^e$;

$R^8$ is H, $C_{1-4}$ alkyl, $CO_2R^a$, —$CH_2CO_2R^a$, —$CH_2OH$, —$CH_2CH_2OH$, tetrazolyl, —$CONHSO_2R^e$, or —$CH_2CONHSO_2R^e$;

$R^9$ is H or Me;

alternatively, $R^8$ and $R^9$ can be taken together with the carbon atom to which they are attached to form a 3- to 5-membered carbocycle;

$R^{10a}$ and $R^{10b}$ are, independently at each occurrence, H, F, Cl, Br, I, $SR^2$, $SCF_3$, CN, $NO_2$, —$B(OH)_2$, —$C(O)R^a$, —$(CH_2)_r$—$CO_2R^a$, —$(CH_2)_r$—$NR^cCO_2R^a$, —$NR^dC(O)R^a$, —$(CH_2)_r$—$C(O)NR^cR^d$, —$NR^cC(O)NR^cR^d$, —$SO_2NR^cR^d$, —$OSO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^a$ is, independently at each, H, $C_{1-6}$ alkyl substituted with 0-4 $R^h$, —$(CH_2)_r$—$C_{3-7}$ carbocycle substituted with 0-4 $R^f$, or —$(CH_2)_r$-5- to 10-membered heterocycle comprising: carbon atoms and 1-4 heteroatoms selected from N, $NR^g$, O, and $S(O)_p$, wherein said heteroaryl is substituted with 0-4 $R^f$;

$R^b$ is, independently at each, H, $C_{1-6}$ alkyl, —$(CH_2)_n$-phenyl, $(C_{1-6}$ alkyl)$C(O)$—, $(C_{3-6}$ cycloalkyl)-$C_{0-4}$ alkyl-$C(O)$—, $(C_{6-10}$ aryl)-$(C_{0-4}$ alkyl)-$C(O)$—, (5- to 10-membered heteroaryl)-$C_{0-4}$ alkyl-$C(O)$—, $(C_{1-6}$ alkyl)-NHC(O)—, $(C_{1-6}$ alkyl)$_2$-NHC(O)—, $(C_{6-10}$ aryl)-$C_{0-4}$ alkyl-NHC(O)—, (5- to 10-membered heteroaryl)-$C_{0-4}$ alkyl-NHC(O)—, $(C_{1-6}$ alkyl)-$SO_2$—, $(C_{6-10}$ aryl)-$C_{0-4}$ alkyl-$SO_2$—, or (5- to 10-membered heteroaryl)-$C_{0-4}$ alkyl-$SO_2$—, wherein said phenyl, aryl and heteroaryl are substituted with 0-2 $R^f$;

$R^c$ is, independently at each, H, $C_{1-6}$ alkyl substituted with 0-3 $R^h$, —$(CH_2)_n$—$C_{3-7}$ cycloalkyl substituted with 0-3 $R^h$, or —$(CH_2)_n$-phenyl substituted with 0-3 $R^h$;

alternatively, $R^b$ and $R^c$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^d$ is, independently at each, H, $C_{1-6}$ alkyl, —$(CH_2)_r$—$C_{3-10}$ carbocycle substituted with 0-3 $R^f$ or a —$(CH_2)_r$-5- to 12-membered heterocycle comprising: carbon atoms and 1-4 heteroatoms selected from N, $NR^g$, O, and $S(O)_p$, wherein said heterocycle is substituted with 0-3 $R^f$;

alternatively, $R^c$ and $R^d$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^e$ is, independently at each, =O, $OR^a$, F, Cl, Br, I, CN, $NO_2$, —$SR^a$, —$OCF_3$, —$NR^bR^c$, —$C(O)R^a$, —$CO_2R^a$, —$NR^dC(O)R^a$, —$C(O)NR^cR^d$, —$OC(O)R^a$, —$NR^dC(O)OR^a$, —$NR^dC(O)NR^cR^d$, —$OC(O)NR^cR^d$, —$SO_2NR^cR^d$, —$NC(O)OR^a$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{3-10}$ carbocycle substituted with 0-3 $R^f$, or a 5- to 12-membered heterocycle comprising: carbon atoms and 1-4 heteroatoms selected from N, $NR^g$, O, and $S(O)_p$, wherein said heterocycle is substituted with 0-3 $R^f$;

$R^f$ is, independently at each, =O, $OR^g$, F, Cl, Br, I, CN, $NO_2$, —$SR^g$, —$OCF_3$, —$NR^cR^c$, —$C(O)R^g$, —$CO_2R^g$, —$NR^cC(O)R^g$, —$C(O)NR^cR^c$, —$OC(O)R^g$, —$NR^cC(O)OR^g$, —$NR^cC(O)NR^cR^c$, —$OC(O)NR^cR^c$, —$SO_2NR^cR^c$, —$NR^cSO_2NR^cR^c$, —$NR^cSO_2R^i$, —$NR^cSO_2CF_3$, —$SO_2CF_3$, —$S(O)_pR^i$, —$(CF_2)_rCF_3$, $C_{1-6}$ alkyl, $C_{2-6}$ alkenyl, $C_{2-6}$ alkynyl, $C_{3-10}$ carbocycle substituted with 0-3 $R^h$, or a 5- to 12-membered heterocycle comprising: carbon atoms and 1-4 heteroatoms selected from N, $NR^g$, O, and $S(O)_p$, and substituted with 0-3 $R^h$;

$R^g$ is, independently at each, H, $C_{1-6}$ alkyl, or —$(CH_2)_n$-phenyl;

$R^h$ is, independently at each, =O, —$(CH_2)_rOR^g$, F, Cl, Br, I, CN, $NO_2$, —$OCF_3$, —$NR^gR^g$, —$C(O)R^g$, —$CO_2R^g$, —$NR^gC(O)R^g$, —$C(O)NR^gR^g$, —$SO_2NR^gR^g$, —$NR^gSO_2NR^gR^g$, —$NR^gSO_2$—$C_{1-4}$ alkyl, —$NR^gSO_2CF_3$, —$NR^gSO_2$-phenyl, —$SO_2CF_3$, —$S(O)_p$—$C_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$ alkyl)-C(O)—, (5-10 membered heteroaryl)-C$_{0-4}$ alkyl-C(O)—, (C$_{1-6}$ alkyl)-NHC(O)—, (C$_{1-6}$ alkyl)$_2$-NHC(O)—, (C$_{6-10}$ aryl)-C$_{0-4}$ alkyl-NHC(O)—, (5-10 membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, (5-10 membered heteroaryl)-C$_{0-4}$ alkyl-SO$_2$—, —(CH$_2$)$_r$—C$_{3-10}$ carbocycle, or a —(CH$_2$)$_r$-5- to 12-membered heterocycle comprising: carbon atoms and 1-4 heteroatoms selected from N, NR$^g$, O, and S(O)$_p$;

R$^i$ is, independently at each, H, C$_{1-6}$ alkyl substituted with 0-3 R$^h$, C$_{3-6}$ cycloalkyl substituted with 0-3 R$^h$, —(CH$_2$)$_n$-phenyl substituted with 0-3 R$^h$, —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-3 R$^h$;

n, at each, is selected from 0, 1, 2, 3, and 4;
p, at each, is selected from 0, 1, and 2; and
r, at each, is selected from 0, 1, 2, 3, and 4.

In a fourth embodiment, the present invention includes a compound of Formula (II) or a stereoisomer, tautomer, pharmaceutically acceptable salt, solvate, or prodrug thereof, wherein:

W is substituted with 0-1 R$^6$ and selected from:

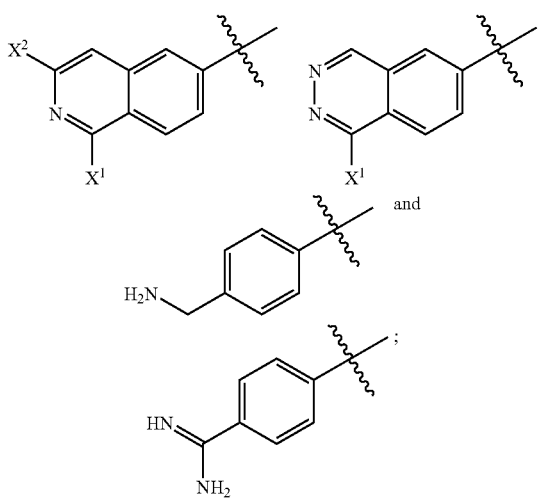

R$^1$ is H, F, Cl, Br, Me, Et, vinyl, 2-propenyl, ethynyl, —CH(OH)Me, OMe, OEt, or cyclopropyl;

R$^2$ and R$^3$ are, independently at each occurrence, H, F, Cl, Br, I, OR$^a$, SR$^a$, OCF$_3$, CN, NO$_2$, —NR$^b$R$^c$, —C(O)R$^a$, —CO$_2$R$^a$, —NR$^d$C(O)R$^a$, —C(O)NR$^c$R$^d$, —SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-4}$ alkyl substituted with 0-2 R$^e$, C$_{2-4}$ alkenyl substituted with 0-2 R$^e$, or C$_{2-6}$ alkynyl substituted with 0-2 R$^e$;

R$^4$ is, independently at each occurrence, H, F, Cl, Br, I, OR$^a$, SR$^a$, OCF$_3$, CN, NO$_2$, —NR$^b$R$^c$, —C(O)R$^a$, —CO$_2$R$^a$, —NR$^d$C(O)R$^a$, —C(O)NR$^c$R$^d$, —SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-4}$ alkyl substituted with 0-2 R$^e$, C$_{2-4}$ alkenyl substituted with 0-2 R$^e$, or C$_{2-4}$ alkynyl substituted with 0-2 R$^e$;

R$^a$ is, independently at each, H, C$_{1-6}$ alkyl substituted with 0-2 R$^h$, —(CH$_2$)$_r$—C$_{3-6}$ cycloalkyl substituted with 0-2 R$^f$, —(CH$_2$)$_r$-phenyl substituted with 0-3 R$^f$ or —(CH$_2$)$_r$-5- to 6-membered heterocycle comprising: carbon atoms and 1-4 heteroatoms selected from N, NR$^g$, O, and S(O)$_p$, wherein said heteroaryl is substituted with 0-3 R$^f$;

R$^b$ is, independently at each, H, C$_{1-6}$ alkyl, —(CH$_2$)$_n$-phenyl, (C$_{1-6}$ alkyl)C(O)—, (C$_{3-6}$ cycloalkyl)-C$_{0-4}$ alkyl-C(O)—, phenyl-(C$_{0-4}$ alkyl)-C(O)—, (5- to 6-membered heteroaryl)-C$_{0-4}$ alkyl-C(O)—, (C$_{1-6}$ alkyl)-NHC(O)—, (C$_{1-6}$ alkyl)$_2$-NHC(O)—, phenyl-C$_{0-4}$ alkyl-NHC(O)—, (5- to 6-membered heteroaryl)-C$_{0-4}$ alkyl-NHC(O)—, (C$_{1-6}$ alkyl)-SO$_2$—, phenyl-C$_{0-4}$ alkyl-SO$_2$—, or (5- to 6-membered heteroaryl)-C$_{0-4}$ alkyl-SO$_2$—, wherein said phenyl and heteroaryl are substituted with 0-2 R$^f$;

R$^c$ is, independently at each, H, C$_{1-6}$ alkyl substituted with 0-3 R$^h$, —(CH$_2$)$_n$—C$_{3-6}$ cycloalkyl substituted with 0-2 R$^h$, or —(CH$_2$)$_n$-phenyl substituted with 0-3 R$^h$;

R$^d$ is, independently at each, H, C$_{1-6}$ alkyl, —(CH$_2$)$_n$—C$_{3-6}$ cycloalkyl substituted with 0-2 R$^f$, —(CH$_2$)$_r$-phenyl substituted with 0-3 R$^f$, or a —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-3 R$^f$;

R$^e$ is, independently at each, =O, OR$^a$, F, Cl, Br, I, CN, NO$_2$, —SR$^a$, —OCF$_3$, —NR$^b$R$^c$, —C(O)R$^a$, —CO$_2$R$^a$, —NR$^d$C(O)R$^a$, —C(O)NR$^c$R$^d$, —OC(O)R$^a$, —NR$^d$C(O)OR$^a$, —NR$^d$C(O)NR$^c$R$^d$, —OC(O)NR$^c$R$^d$, —SO$_2$NR$^c$R$^d$, —NC(O)OR$^a$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{3-6}$ cycloalkyl substituted with 0-2 R$^f$, phenyl substituted with 0-3 R$^f$ or a 5- to 10-membered heterocycle comprising: carbon atoms and 1-4 heteroatoms selected from N, NR$^g$, O, and S(O)$_p$, wherein said heterocycle is substituted with 0-3 R$^f$;

R$^f$ is, independently at each, =O, OR$^g$, F, Cl, Br, I, CN, NO$_2$, —SR$^g$, —OCF$_3$, —NR$^c$R$^c$, —C(O)R$^g$, —CO$_2$R$^g$, —NR$^c$C(O)R$^g$, —C(O)NR$^c$R$^c$, —OC(O)R$^g$, —NR$^c$C(O)OR$^g$, —NR$^c$C(O)NR$^c$R$^c$, —OC(O)NR$^c$R$^c$, —SO$_2$NR$^c$R$^c$, —NR$^c$SO$_2$NR$^c$R$^c$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl, C$_{2-6}$ alkenyl, C$_{2-6}$ alkynyl, C$_{3-6}$ cycloalkyl substituted with 0-2 R$^f$, phenyl substituted with 0-3 R$^f$, or a 5- to 10-membered heterocycle comprising: carbon atoms and 1-4 heteroatoms selected from N, NR$^g$, O, and S(O)$_p$, and substituted with 0-3 R$^h$;

R$^h$ is, independently at each, =O, —(CH$_2$)$_r$OR$^g$, F, Cl, Br, I, CN, NO$_2$, —OCF$_3$, —NR$^g$R$^g$, —C(O)R$^g$, —CO$_2$R$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —SO$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$ alkyl)-C(O)—, (5-10 membered heteroaryl)-C$_{0-4}$ alkyl-C(O)—, (C$_{1-6}$ alkyl)-NHC(O)—, (C$_{1-6}$ alkyl)$_2$-NHC(O)—, (C$_{6-10}$ aryl)-C$_{0-4}$ alkyl-NHC(O)—, (5-10 membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, (5-10 membered heteroaryl)-C$_{0-4}$ alkyl-SO$_2$—, C$_{3-6}$ cycloalkyl, phenyl, or a —(CH$_2$)$_r$-5- to 10-membered heterocycle comprising: carbon atoms and 1-4 heteroatoms selected from N, NR$^g$, O, and S(O)$_p$; and R$^i$ is, independently at each, H, C$_{1-6}$ alkyl substituted with 0-3 R$^h$, C$_{3-6}$ cycloalkyl substituted with 0-3 R$^h$, —(CH$_2$)$_n$-phenyl substituted with 0-3 R$^h$, —(CH$_2$)$_r$-5- to 6-membered heterocycle comprising: carbon atoms and 1-4 heteroatoms selected from N, NR$^g$, O, and S(O)$_p$, wherein said heterocycle is substituted with 0-3 R$^h$.

In a fifth embodiment, the present invention includes a compound of Formula (II) or a stereoisomer, tautomer, pharmaceutically acceptable salt, solvate, or prodrug thereof, wherein:

W is substituted with 0-1 $R^6$ and selected from:

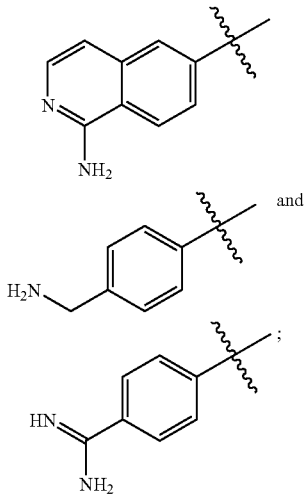

$R^1$ is H, F, Cl, Br, Me, Et, vinyl, 2-propenyl, ethynyl, —CH(OH)Me, OMe, OEt, or cyclopropyl;
$R^2$ is H, F, Cl, Me, Et, OMe, O(i-Pr), or —OCHF$_2$;
$R^3$ is H, OMe, or OEt;
$R^4$ is H or F;
$R^7$ is H, $C_{1-4}$ alkyl, or —CH$_2$CO$_2$R$^a$;
$R^8$ is H or $C_{1-4}$ alkyl;
$R^9$ is H; and
$R^{10a}$ and $R^{10b}$ are, independently at each occurrence, H, $C_{1-4}$ alkyl, F, Cl, —S—$C_{1-4}$ alkyl, CF$_3$, SCF$_3$, CO$_2$Me, CONH$_2$, —NHCOH, —NHCOMe, —NHCOEt, —NHCOPr, —NHCO(i-Pr), —NHCO(i-Bu), —NHCO-cyclopropyl, —N(Me)COMe, —NHCO$_2$Me, —NHCO$_2$Et, —NHCONH$_2$, —NHCONHMe, —NHCONMe$_2$, —NHCON(Me)Et, —NHCON(Me)(i-Pr), —NHCO-(1-azetidinyl), —NHCO-(1-pyrrolidinyl), —NHCO-(3-thiazolidinyl), —SO$_2$Me, —SO$_2$Et, —SO$_2$Pr, —SO$_2$(i-Pr), —SO$_2$(i-Bu), —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$-(4-morpholinyl), —SO$_2$-(4-thiamorpholinyl), —SO$_2$-(4-Me-1-piperazinyl), —SO$_2$NH$_2$, —SO$_2$NHMe, —SO$_2$NHEt, —SO$_2$NH(i-Pr), —SO$_2$NH-cyclopropyl, —SO$_2$NH-cyclohexyl, —SO$_2$NH(t-Bu), —SO$_2$N(Me)Bn, —SO$_2$NMe$_2$, —OSO$_2$NH$_2$, —NHSO$_2$NH$_2$, —NHSO$_2$Me, Ph, 4-F-Ph, NO$_2$, or —B(OH)$_2$.

In a sixth embodiment, the present invention includes a compound of Formula (II) or a stereoisomer, tautomer, pharmaceutically acceptable salt, solvate, or prodrug thereof, wherein:

$R^1$ is OMe or OEt;
$R^2$ is OMe or O(i-Pr);
$R^3$ is H;
$R^4$ is H or F;
$R^7$ is H or Me;
$R^8$ is H;
$R^9$ is H;
$R^{10a}$ is, independently at each, H, —SO$_2$—$C_{1-4}$ alkyl, —SO$_2$-cyclopropyl, —SO$_2$-cyclobutyl, or 3,5-diethyl-1H-pyrazol-1-yl; and $R^{10b}$ is, independently at each, H, —NHCOMe, —NHCOEt, —NHCO$_2$Me, or —NHCO$_2$Et.

In a seventh embodiment, the present invention includes a compound of Formula (III):

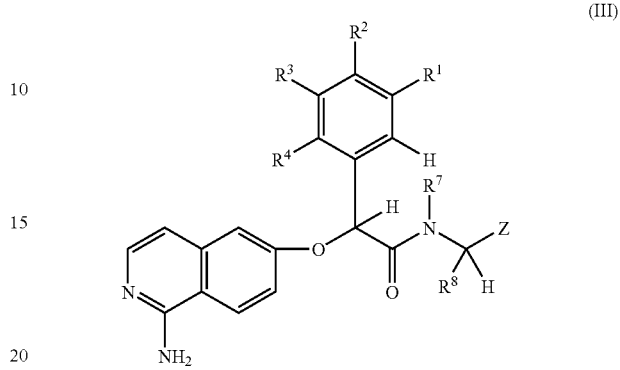

or a stereoisomer, tautomer, pharmaceutically acceptable salt, solvate, or prodrug thereof, wherein:

Z is selected from:

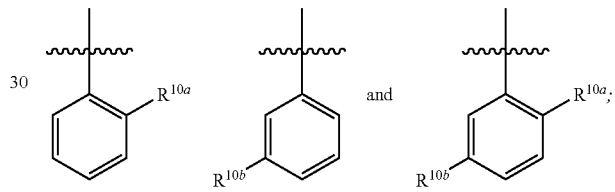

$R^1$ is H, F, Cl, Br, Me, Et, vinyl, 2-propenyl, ethynyl, —CH(OH)Me, OMe, OEt, or cyclopropyl;
$R^2$ is H, F, Cl, Me, Et, OMe, O(i-Pr), or —OCHF$_2$;
$R^3$ is H, OMe, or OEt;
$R^4$ is H or F;
$R^7$ is H, $C_{1-4}$ alkyl, or —CH$_2$CO$_2$R$^a$;
$R^8$ is H or $C_{1-4}$ alkyl; and
$R^{10a}$ and $R^{10b}$ are, independently at each occurrence, H, $C_{1-4}$ alkyl, F, Cl, —S—$C_{1-14}$ alkyl, CF$_3$, SCF$_3$, CO$_2$Me, CONH$_2$, —NHCOH, —NHCOMe, —NHCOEt, —NHCOPr, —NHCO(i-Pr), —NHCO(i-Bu), —NHCO-cyclopropyl, —N(Me)COMe, —NHCO$_2$Me, —NHCO$_2$Et, —NHCONH$_2$, —NHCONHMe, —NHCONMe$_2$, —NHCON(Me)Et, —NHCON(Me)(i-Pr), —NHCO-(1-azetidinyl), —NHCO-(1-pyrrolidinyl), —NHCO-(3-thiazolidinyl), —SO$_2$Me, —SO$_2$Et, —SO$_2$Pr, —SO$_2$(i-Pr), —SO$_2$(i-Bu), —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$-(4-morpholinyl), —SO$_2$-(4-thiamorpholinyl), —SO$_2$-(4-Me-1-piperazinyl), —SO$_2$NH$_2$, —SO$_2$NHMe, —SO$_2$NHEt, —SO$_2$NH(i-Pr), —SO$_2$NH-cyclopropyl, —SO$_2$NH-cyclohexyl, —SO$_2$NH(t-Bu), —SO$_2$N(Me)Bn, —SO$_2$NMe$_2$, —OSO$_2$NH$_2$, —NHSO$_2$NH$_2$, —NHSO$_2$Me, Ph, 4-F-Ph, NO$_2$, or —B(OH)$_2$.

In an eighth embodiment, the present invention includes a compound of Formula (III) or a stereoisomer, tautomer, pharmaceutically acceptable salt, solvate, or prodrug thereof, wherein:

$R^1$ is H, F, Cl, Me, Et, OMe, or OEt;
$R^8$ is H;
$R^{10a}$ is, independently at each, H, —SO$_2$—$C_{1-4}$ alkyl, —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$NH—C$_{1-4}$ alkyl, —SO$_2$NH-cyclopropyl, —SO$_2$NMe$_2$, CONMe$_2$, CO(1-pyrrolidinyl), CO(1-piperidinyl), 1-piperidyl, 4-morpholinyl, or 3,5-diethyl-1H-pyrazol-1-yl; and R$^{10b}$ is, independently at each, H, —NHCOH, —NHCOMe, —NHCOEt, —NHCO$_2$Me, —NHCO$_2$Et, —NHCONHMe, —NHCONH$_2$, —NHCONMe$_2$, —NHCON(Me)Et, —NHCON(Me)(i-Pr), —NHCO-(1-azetidinyl), —NHCO-(1-pyrrolidinyl), —NHCO-(3-thiazolidinyl), —OSO$_2$NH$_2$, —NHSO$_2$NH$_2$, —NHSO$_2$Me, —SO$_2$NH$_2$, or NO$_2$.

In a ninth embodiment, the present invention includes a compound of Formula (III) or a stereoisomer, tautomer, pharmaceutically acceptable salt, solvate, or prodrug thereof, wherein:

R$^7$ is H;
R$^8$ is H;
R$^{10a}$ is, independently at each, —SO$_2$—C$_{1-4}$ alkyl, —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$NH—C$_{1-4}$ alkyl, —SO$_2$NH-cyclopropyl, —SO$_2$NMe$_2$, CONMe$_2$, CO(1-pyrrolidinyl), CO(1-piperidinyl), 1-piperidyl, 4-morpholinyl, or 3,5-diethyl-1H-pyrazol-1-yl; and R$^{10b}$ is, independently at each, —NHCOH, —NHCOMe, —NHCOEt, —NHCO$_2$Me, —NHCO$_2$Et, —NHCONHMe, —NHCONMe$_2$, —NHCON(Me)Et, —NHCON(Me)(i-Pr), —NHCO-(1-azetidinyl), —NHCO-(1-pyrrolidinyl), —NHCO-(3-thiazolidinyl), —NHCONH$_2$, —OSO$_2$NH$_2$, —NHSO$_2$NH$_2$, —NHSO$_2$Me, or —SO$_2$NH$_2$.

In a tenth embodiment, the present invention includes a compound of Formula (III) or a stereoisomer, tautomer, pharmaceutically acceptable salt, solvate, or prodrug thereof, wherein:

R$^7$ is H, C$_{1-4}$ alkyl, or —CH$_2$CO$_2$R$^a$;
R$^8$ is H;
R$^{10a}$ is, independently at each, —SO$_2$—C$_{1-4}$ alkyl, —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$NH—C$_{1-4}$ alkyl, —SO$_2$NH-cyclopropyl, —SO$_2$NMe$_2$, CONMe$_2$, CO(1-pyrrolidinyl), CO(1-piperidinyl), 1-piperidyl, or 4-morpholinyl, or 3,5-diethyl-1H-pyrazol-1-yl; and R$^{10b}$ is H.

In an eleventh embodiment, the present invention includes a compound of Formula (III) or a stereoisomer, tautomer, pharmaceutically acceptable salt, solvate, or prodrug thereof, wherein:

R$^7$ is H, C$_{1-4}$ alkyl, or —CH$_2$CO$_2$R$^a$;
R$^8$ is H;
R$^{10a}$ is, independently at each, —SO$_2$—C$_{1-4}$ alkyl, —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$NH—C$_{1-4}$ alkyl, —SO$_2$NH-cyclopropyl, —SO$_2$NMe$_2$, CONMe$_2$, CO(1-pyrrolidinyl), CO(1-piperidinyl), 1-piperidyl, 4-morpholinyl, or 3,5-diethyl-1H-pyrazol-1-yl; and R$^{10b}$ is, independently at each, —NHCOH, —NHCOMe, —NHCOEt, —NHCO$_2$Me, —NHCO$_2$Et, —NHCONHMe, —NHCONMe$_2$, —NHCON(Me)Et, —NHCON(Me)(i-Pr), —NHCO-(1-azetidinyl), —NHCO-(1-pyrrolidinyl), —NHCO-(3-thiazolidinyl), —NHCONH$_2$, —OSO$_2$NH$_2$, —NHSO$_2$NH$_2$, —NHSO$_2$Me, or —SO$_2$NH$_2$.

In a twelfth embodiment, the present invention includes a compound of Formula (III) or a stereoisomer, tautomer, pharmaceutically acceptable salt, solvate, or prodrug thereof, wherein:

R$^7$ is H, C$_{1-4}$ alkyl, or —CH$_2$CO$_2$R$^a$;
R$^8$ is H;
R$^{10a}$ is H;
R$^{10b}$ is, independently at each, —NHCOH, —NHCOMe, —NHCOEt, —NHCO$_2$Me, —NHCO$_2$Et, —NHCONHMe, —NHCONMe$_2$, —NHCON(Me)Et, —NHCON(Me)(i-Pr), —NHCO-(1-azetidinyl), —NHCO-(1-pyrrolidinyl), —NHCO-(3-thiazolidinyl), —NHCONH$_2$, —OSO$_2$NH$_2$, —NHSO$_2$NH$_2$, —NHSO$_2$Me, or —SO$_2$NH$_2$.

In a thirteenth embodiment, the present invention includes a compound of Formula (IIa):

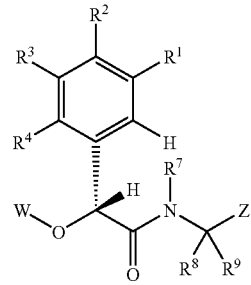

(IIa)

wherein
W, Z, R$^1$, R$^2$, R$^3$, R$^4$, R$^7$, R$^8$ and R$^9$ are the same as defined in the third embodiment.

In a fourteenth aspect, the present invention provides a compound selected from the exemplified examples or stereoisomers, tautomers, pharmaceutically acceptable salts, solvates, or prodrugs thereof.

In another embodiment the present invention provides a pharmaceutical composition comprising a pharmaceutically acceptable carrier and at least one of the compounds of the present invention or stereoisomers, tautomers, pharmaceutically acceptable salts, solvates, or prodrugs thereof.

In another embodiment the present invention provides a pharmaceutical composition comprising a pharmaceutically acceptable carrier and a therapeutically effective amount of at least one of the compounds of the present invention or stereoisomers, tautomers, pharmaceutically acceptable salt, solvates, or prodrugs thereof.

In another embodiment, the present invention provides a novel process for making one of the compounds of the present invention or stereoisomers, tautomers, pharmaceutically acceptable salt, solvates, or prodrugs thereof.

In another embodiment, the present invention provides a novel intermediate for making one of the compounds of the present invention or stereoisomers, tautomers, pharmaceutically acceptable salt, solvates, or prodrugs thereof.

In another embodiment the present invention provides a method for modulation of the coagulation cascade and/or contact activation system comprising administering to a host in need of such treatment a therapeutically effective amount of at least one of the compounds of the present invention or stereoisomers, tautomers, pharmaceutically acceptable salt, solvates, or prodrugs thereof.

In another embodiment the present invention provides a method for treating thrombotic or thromboembolic disorders comprising: administering to a host in need of such treatment a therapeutically effective amount of at least one of the compounds of the present invention or stereoisomers, tautomers, pharmaceutically acceptable salt, solvates, or prodrugs thereof.

In another embodiment, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a novel method of treating a patient in need of thromboembolic disorder treatment, comprising: administering a compound of the present invention or stereoisomers, tautomers, pharmaceutically acceptable salt, solvates, or prodrugs thereof in an amount effective to treat a thromboembolic disorder.

In another embodiment, the present invention provides a pharmaceutical composition further comprising at least one additional herapeutic agent selected from one or more of potassium channel openers, potassium channel blockers, calcium channel blockers, sodium hydrogen exchanger inhibitors, antiarrhythmic agents, antiatheroaclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In a preferred embodiment, the present invention provides a pharmaceutical composition wherein the additional therapeutic agent(s) is an antihypertensive agent selected from ACE inhibitors, AT-1 receptor antagonists, beta-adrenergic receptor antagonists, ETA receptor antagonists, dual ETA/AT-1 receptor antagonists, and vasopeptidase inhibitors, an antiarrythmic agent selected from IKur inhibitors, an anticoagulant agent selected from thrombin inhibitors, antithrombin-III activators, heparin co-factor II activators, other factor VIIa inhibitors, other plasma kallikrein inhibitors, plasminogen activator inhibitor (PAI-1) antagonists, thrombin activatable fibrinolysis inhibitor (TAFI) inhibitors, factor IXa inhibitors, factor Xa inhibitors, and factor XIa inhibitors, or an antiplatelet agent selected from GPIIb/IIIa blockers, protease activated receptor (PAR-1) antagonists, phosphodiesterase-III inhibitors, $P2Y_1$ receptor antagonists, $P2Y_{12}$ receptor antagonists, thromboxane receptor antagonists, cyclooxygense-1 inhibitors, and aspirin, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, antistreplase, urokinase, and streptokinase, or a combination thereof.

In a preferred embodiment, the present invention provides a pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent selected from clopidogrel and aspirin, or a combination thereof.

In a preferred embodiment, the present invention provides a pharmaceutical composition, wherein the additional therapeutic agent is the anti-platelet agent clopidogrel.

In another embodiment, the present invention provides a novel method, comprising: administering a compound of the present invention or stereoisomers, tautomers, pharmaceutically acceptable salt, solvates, or prodrugs thereof in an amount effective to treat a thromboembolic disorder.

In another embodiment, the present invention provides a compound of the present invention or stereoisomers, tautomers, pharmaceutically acceptable salt, solvates, or prodrugs thereof, for use in therapy.

In another embodiment, the present invention also provides the use of a compound of the present invention or stereoisomers, tautomers, pharmaceutically acceptable salt, solvates, or prodrugs thereof, for the manufacture of a medicament for the treatment of a thrombotic or a thromboembolic disorder.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of a thrombotic or thromboembolic disorder.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of a thrombotic or thromboembolic disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat a thrombotic or thromboembolic disorder.

In another preferred embodiment, the present invention provides a novel article of manufacture, further comprising: (d) a second container; wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis using optically active starting materials or optically active catalysts. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. The inventive compounds may be in the free or hydrate form.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 700 grams per mole. Even more preferably, the molecular weight is less than about 600 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases wherein there are quaternary carbon atoms on compounds of the present invention, these may be replaced by silicon atoms, provided they do not form Si—N or Si—O bond.

When any variable occurs more than one time in any constituent or formula for a compound, its definition at each is independent of its definition at every other. Thus, for example, if a group is shown to be substituted with 0-3 $R^f$, then said group may optionally be substituted with up to three $R^f$ groups and $R^f$ at each is selected independently from the definition of $R^f$.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_{1-6}$ alkyl" denotes alkyl having 1 to 6 carbon atoms. Alkyl groups can be unsubstituted or substituted so that one or more of its hydrogens are replaced by another chemical group. Examples of alkyl include, but are not limited to, methyl (Me), ethyl (Et), n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl, and the like.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. Branched cycloalkyl groups such as 1-methylcyclopropyl and 2-methylcyclopropyl are included in the definition of "cycloalkyl".

"Alkoxy" or "alkyloxy" represents an alkyl group as defined above with the indicated number of carbon atoms attached through an oxygen bridge. For example, "$C_{1-6}$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, 7, or 8-membered monocyclic or bicyclic or 7, 8, 9, 10, 11, 12, or 13-membered bicyclic or tricyclic ring system consisting of carbon atoms, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, and indanyl.

As used herein, the term "bicyclic carbocycle" or "bicyclic carbocyclic group" is intended to mean a stable 9 or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl. When the term "carbocycle" is used, it is intended to include "aryl".

"Aryl" groups refer to monocyclic or polycyclic aromatic hydrocarbons, including, for example, phenyl, naphthyl, phenanthranyl, and the like. Aryl moieties are well known and described, for example, in *Hawley's Condensed Chemical Dictionary* (13 ed.), R. J. Lewis, ed., J. Wiley & Sons, Inc., New York (1997). Aryl groups can be substituted or unsubstituted.

As used herein, the term "heterocycle" or "heterocyclic group" is intended to mean a stable 5, 6, or 7-membered monocyclic or polycyclic or 7, 8, 9, 10, 11, 12, 13, or 14-membered polycyclic heterocyclic ring which is saturated, partially unsaturated or fully unsaturated, and which consists of carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9 or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydrobenzofuranyl, chromanyl, 1,2,3,4-tetrahydro-quinoxaline, and 1,2,3,4-tetrahydro-quinazoline.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Preferred heteroaryl groups are stable 5, 6, or 7-membered monocyclic or 7, 8, 9, or 10-membered bicyclic heterocyclic aromatic rings which consists of carbon atoms and 1, 2, 3, or 4 heteroatoms independently selected from the group consisting of N, NH, O and S. It is to be noted that total number of S and O atoms in the aromatic heterocycle is not more than 1. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, oxadiazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like. Heteroaryl groups can be substituted or unsubstituted.

Also included are fused ring and spiro compounds containing, for example, the above carbocycles or heterocycles.

Bridged rings are also included in the definition of carbocycle or heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

When a dotted ring is used within a ring structure, this indicates that the ring structure may be saturated, partially saturated or unsaturated.

The term "counterion" is used to represent a small, negatively charged species such as chloride, bromide, hydroxide, acetate, and sulfate.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, the disclosure of which is hereby incorporated by reference.

Isotopically labeled compounds of the present invention, i.e., wherein one or more of the atoms described are replaced by an isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of prodrugs,* edited by H. Bundgaard, (Elsevier, 1985), and *Methods in Enzymology,* Vol. 42, at pp. 309-396, edited by K. Widder, et. al. (Academic Press, 1985);

b) *A Textbook of Drug Design and Development,* edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews,* Vol. 8, p. 1-38 (1992);

d) H. Bundgaard, et al., *Journal of Pharmaceutical Sciences,* Vol. 77, p. 285 (1988); and e) N. Kakeya, et. al., *Chem Phar Bull.,* Vol. 32, p. 692 (1984).

Preparation of Prodrugs is Well Known in the Art and Described in, for example, *Medicinal Chemistry: Principles and Practice,* ed. F. D. King, The Royal Society of Chemistry, Cambridge, UK, 1994, which is incorporated herein by reference in its entirety.

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like. Methods of solvation are generally known in the art.

As used herein, the term "patient" or "host" encompasses all mammalian species.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination with other active ingredients to inhibit factor VIIa or to treat the disorders listed herein. When applied to a combination, the term refers to combined amounts of the active ingredients that result in the therapeutic effect, whether administered in combination, serially or simultaneously. The combination of compounds is preferably a synergistic combination. Synergy, as described, for example, by Chou and Talalay, *Adv. Enzyme Regul.* 1984, 22:27-55, occurs when the effect (in this case, anticoagulant effect) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The term "pharmaceutical composition" means a composition comprising a compound of the invention in combination with at least one additional pharmaceutical carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th ed., 1990, which is incorporated herein by reference in its entirety.

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "M" for molar, "mmol" for millimole or millimoles, "min" for minute or minutes, "h" for hour or hours, "rt" for room temperature, "atm" for atmosphere, "psi" for pounds per square inch, "RT" for retention time, "sat" or "sat'd" for saturated, "MW" for molecular weight, "MS" for mass spectrometry, "ESI" for electrospray ionization mass spectroscopy, "HR" for high resolution, "LC-MS" for liquid chromatography mass spectrometry, "HPLC" for high pressure liquid chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, "tlc" or "TLC" for thin layer chromatography, and "α", "β", "R", "S", "E", and "Z" are stereochemical designations familiar to one skilled in the art.

As used throughout the specification, the following abbreviations for chemical reagents apply:

AcOH or HOAc is acetic acid,
AIBN is 2,2'-azo-bis-isobutylnitrile,
$BH_3.SMe_2$ is borane-dimethyl sulfide complex,
$BH_3$.THF is borane-tetrahydrofuran complex,
BINAP is 2,2'-bis(diphenylphosphino)-1,1'-binaphthalene,
Bn is benzyl,
Boc is tert-butyl oxycarbonyl,
BOP is benzotriazol-1-yloxy-tris(dimethylamino)phosphonium hexafluorophosphate,
Bu is butyl,
iBu or i-Bu is isobutyl,
t-Bu is tert-butyl,
Cbz is carbonylbenzyloxy,
CbzSerOtBu is (S)-2-tert-butoxycarbonylamino-3-hydroxy-propionic acid tert-butyl ester,
CDI is 1,1'-carbonyldiimidazole,
$CH_2Cl_2$ is dichloromethane,
$CH_3CN$ is acetonitrile,
Davis oxaziridine is 2-benzenesulfonyl-3-phenyl-oxaziridine,
DBU is 1,8-diazabicyclo[5.4.0]undec-7-ene,
DCE is 1,2-dichloroethane,
DEAD is diethyl azodicarboxylate,
DIBAH is diisobutylaluminum hydride,
DIC is 1,3-diisopropylcarbodiimide,
DIEA or DIPEA is N,N-diisopropylethyl amine,
DMA is N,N-dimethylacetamide,
DMAP is dimethylaminopyridine,
DME is dimethyl ether,
DMF is dimethylformamide,
DMPU is 1,3-dimethyl-3,4,5,6-tetrahydro-2(1H)-pyrimidone,
DMSO is dimethyl sulfoxide,
DPPA is diphenylphosphoryl azide,
EDCI or EDC is 1-(3-dimethylaminopropyl)-3-ethylcarbodiimide hydrochloride,
Et is ethyl,
EtOH is ethanol,
EtOAc is ethyl acetate,
$Et_2O$ is diethyl ether,
HATU is O-(7-azabenzotriazol-1-yl)-N,N,N',N'-tetramethyluronium,
HBTU is O-benzotriazol-1-yl-N,N,N',N'-tetramethyluronium hexafluorophosphate,
HCl is hydrochloric acid,
HOAt or HOAT is 1-hydroxy-7-azabenzotriazole,
HOBt or HOBT is 1-hydroxybenzotriaole,
$H_3PO_4$ is phosphoric acid,
$K_2CO_3$ is potassium carbonate,
LAH is lithium aluminum hydride
LDA is lithium diisopropylamide,
LiHMDS is bis(trimethylsilyl)amide,
LiOH is lithium hydroxide,
mCPBA or MCPBA is meta-chloroperbenzoic acid,
Me is methyl,
MeOH is methanol,
$MgSO_4$ is magnesium sulfate,
MoOPH is oxodiperoxymolybdenum(pyridine)(hexamethylphosphoric triamide),
MsCl is methanesulfonyl chloride,
Na is sodium,
NaH is sodium hydride,
$NaHCO_3$ is sodium bicarbonate,
$NaHSO_3$ is sodium thiosulfate,
NaOAc is sodium acetate,
NaOH is sodium hydroxide,
$Na_2SO_4$ is sodium sulfate,
NBS is N-bromosuccinimide,
NCS is N-chlorosuccinimide,
Ni is nickel,
OAc is acetate,
Pd/C is palladium on carbon,
$Pd(PPh_3)_4$ is tetraks (triphenylphosphine) palladium,
Ph is phenyl,
Pr is propyl,
iPr or i-Pr is isopropyl,
i-PrOH or IPA is isopropanol,
PyBroP or Py-BroP is bromotripyrrolidinophosphonium hexafluorophosphate,
Selectfluor™ is [1 (chloromethyl)-4-fluoro-1,4-diazoniabicyclo[2,2,2]octanebis(tetrafluoroborate)],
TBAF is tetrabutylammoniumfluoride,
TBAI is tetrabutylammonium iodide,
tBME is tert-butyl methyl ether,
TEA is triethylamine,
TFA is trifluoroacetic acid,
TFAA is trifluoroacetic anhydride,
THF is tetrahydrofuran.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. Preferred methods include, but are not limited to, those described below. All references cited herein are hereby incorporated in their entirety herein by reference.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3nd Edition, 1999). All references cited herein are hereby incorporated in their entirety herein by reference.

Compounds having the general Formula (I):

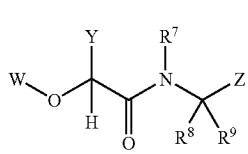

wherein $R^7$, $R^8$, $R^9$, W, Y and Z are each as defined above, can be prepared by coupling an acid of Formula (Ia):

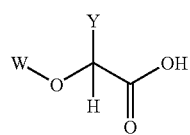

with an amine of Formula (Ib):

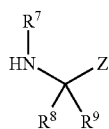

under conditions suitable for forming an amide bond between the acid and the amine. Coupling conditions can be found in Bodanszky, "Principles of Peptide Synthesis, Second Edition" Springer Verlag Ed, Berlin (1993). Coupling reagents include CDI, DIC, and EDCI. Optionally, an intermediate activated ester can be prepared by adding one equivalent of 1-hydroxybenzotriazole or 1-hydroxy-7-azabenzotriazole. Other coupling reagents include HATU, HBTU, and Py-Brop which are usually reacted in the presence of one equivalent of a tertiary base such as DIEA or TEA. Protection and deprotection of functional groups may be required before or after the amide formation step to afford a compound of Formula (I).

The intermediate acid of Formula (Ia) can be prepared according to the steps described in Scheme 1. Thus, when X is a leaving group such as Cl, Br or $OSO_2Me$, alcohols 1 (prepared following the methods shown in later Schemes and in the Examples) react with acetate derivatives 2 under basic conditions to give 3. When X=OH, alcohols 1 react with acetate derivatives 2 under Mitsonobu conditions (*Bull. Chem. Soc. Jpn.* 1967, 40, 2380), for example, in the presence of triphenylphosphine and DEAD. PG is a protecting group such as methyl or benzyl. Deprotection of PG in 3 by hydrolysis or hydrogenation gives acid intermediates Ia.

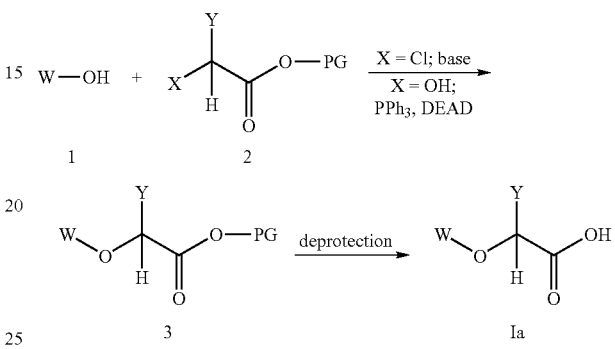

Scheme 1

For W—OH=1-aminoisoquinolin-6-ol and its derivatives, these alcohols can be prepared following the reactions shown in Scheme 2. Acids 5 can be accessed from bromides 4 via lithium halogen exchange using, for example, n-BuLi, followed by treatment with carbon dioxide. Acids 5 can then be advanced to benzamides 6 via formation of the primary amide using, for example, oxalyl chloride and DMF then ammonium hydroxide, followed by treatment with N,N-dimethylformamide in a solvent such as N,N-dimethylacetamide. Heating benzamides 6 in the presence of a base such as potassium tert-butoxide provides cyclized products 7. These can then be advanced by methods known to those skilled in the art (an example is shown in Scheme 2 and is exemplified later in the Examples) to 1-aminoisoquinolin-6-ol and its derivatives (9).

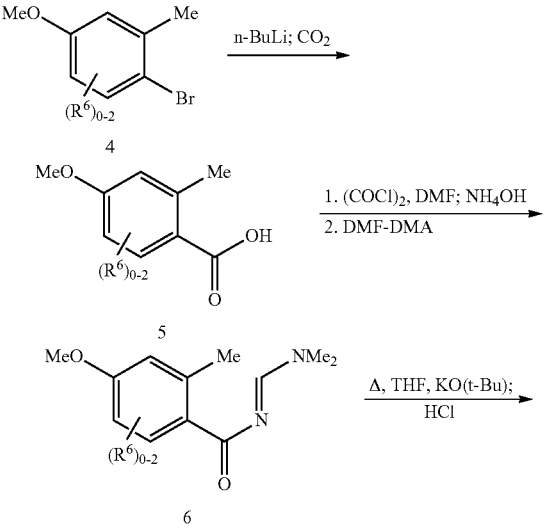

Scheme 2

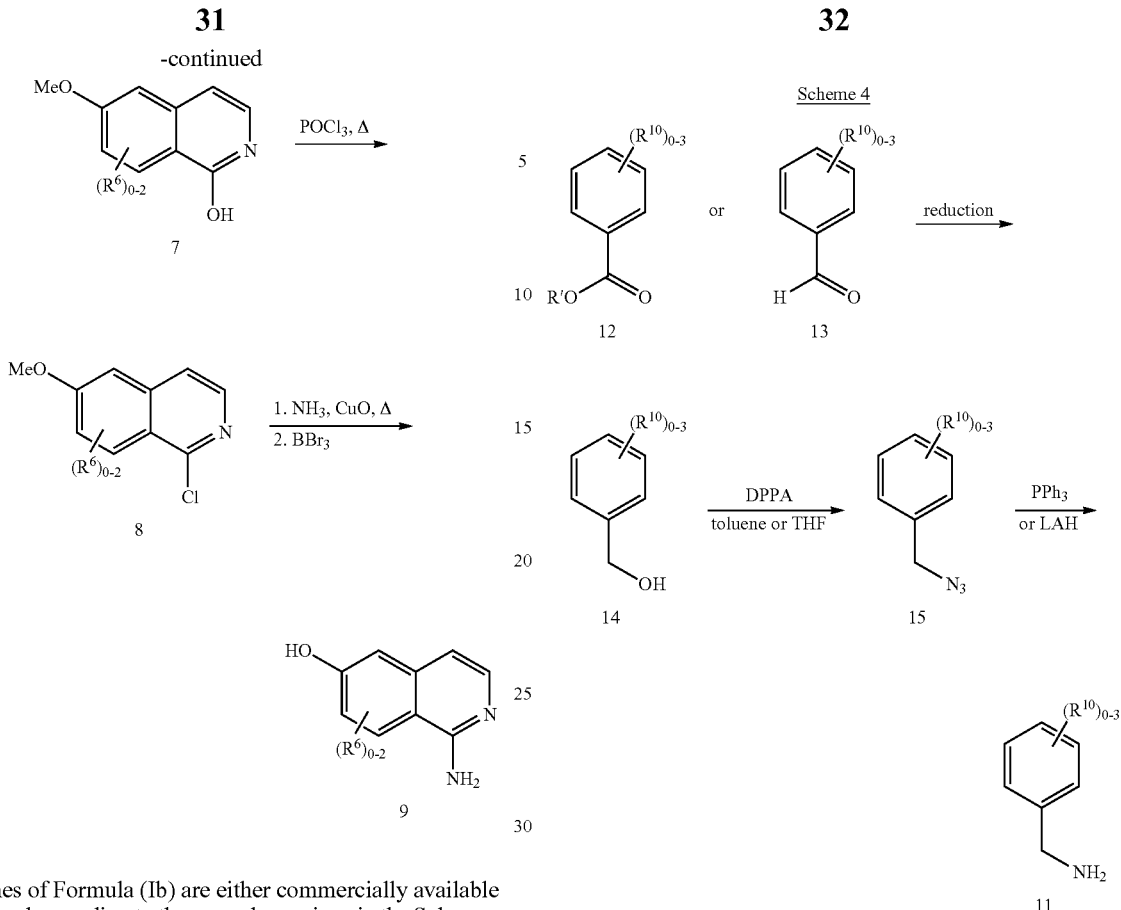

Amines of Formula (Ib) are either commercially available or prepared according to the procedures given in the Schemes below and Examples. In general, functionalized benzylamines 11 can be prepared as exemplified in Scheme 3 via reduction of commercially available or prepared benzonitriles 10 (as shown in the Schemes and Examples that follow) via, for example, hydrogenation in the presence of a catalyst such as Pd/C or Raney Nickel, or using a hydride source, such as $BH_3$ or LAH in THF. Alternatively, as shown in Scheme 4, benzylamines 11 can be prepared from esters 12 or aldehydes 13 via reduction to benzyl alcohols 14 using, for example, LAH, followed by conversion to azides 15 with an appropriate reagent such as diphenylphosphoryl azide in a solvent such as THF or toluene. Reduction of azides 15 with, for example, LAH or triphenylphosphine, provides benzylamines 11. Finally, as shown in Scheme 5, benzylamines 11 can also be prepared from esters 12 via hydrolysis, then formation of the primary amide via, for example, treatment with ammonium hydroxide in the presence of appropriate coupling reagents, such as EDC and HOBT or HOAT, followed by reduction of the derived primary amide with a hydride source, such as $BH_3$.

Scheme 3

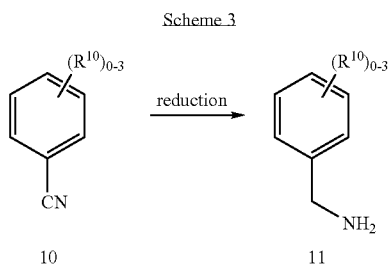

Amines of Formula (Ib), in which $R^7$=alkyl can be prepared in several ways. For example, they can be prepared from benzylamines 11 as exemplified in Scheme 6 via protection with, for example, trifluoroacetic anhydride to give 16, followed by alkylation with an alkyl halide, for example, methyl iodide to provide trifluoroacetates 17. Deprotection with a base such as potassium carbonate yields the desired N-methyl benzylamines 18. Amines of Formula (Ib), in which $R^7$=alkyl can also be prepared from benzamides 20 (see Scheme 7) which can be accessed from acids 19 via, for example, acid chloride formation and reaction with amine $NH_2R^7$ or via coupling with amine $NH_2R^7$ in the presence of coupling agents, for example, EDC and HOAT and a base such as DIPEA. Reduction of benzamides 20 via methods known to those skilled in the art provides benzylamines 18. Finally, amines of Formula (Ib), in which $R^7$=alkyl can also be prepared from aldehydes 13 via reductive amination (Scheme 8) under conditions known to those skilled in the art.

Scheme 6

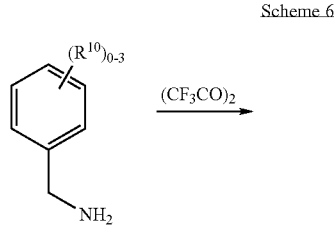

Scheme 7

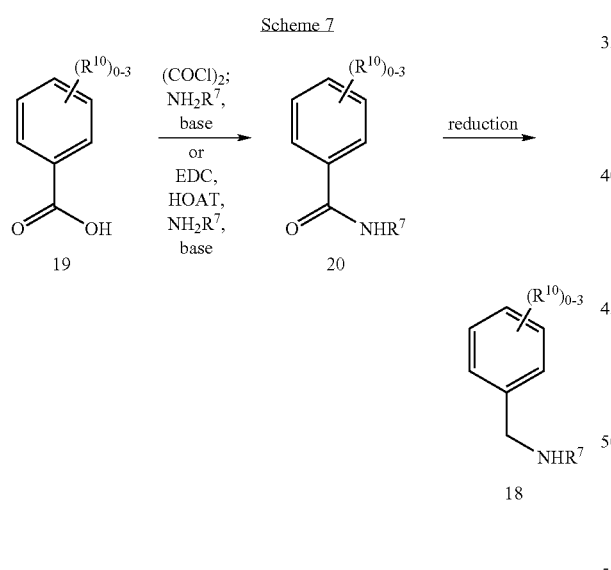

Scheme 8

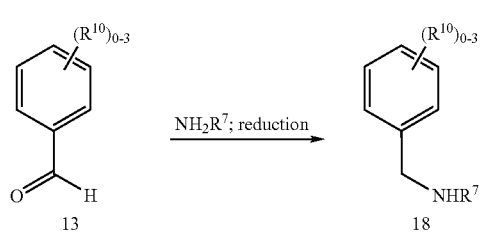

Benzylamines 23 containing an ortho-sulfone substituent can be prepared, as shown in Scheme 9, from sulfides 21, via oxidation to benzonitrile sulfones 22 with an appropriate oxidizing agent, such as MCPBA. Benzonitriles 22 can then be converted to the corresponding benzylamines 23 as was previously shown in Scheme 3.

Scheme 9

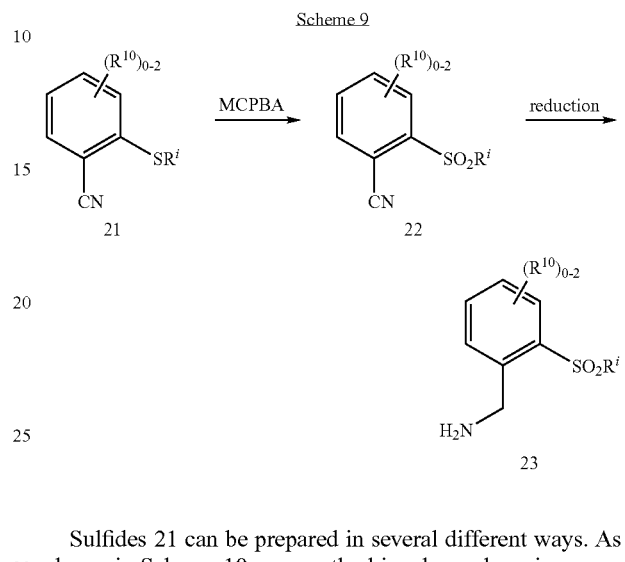

Sulfides 21 can be prepared in several different ways. As shown in Scheme 10, one method involves advancing commercially available o-bromobenzonitriles 24 via lithium-halogen exchange using, for example n-butyl lithium at cold temperatures in a solvent such as THF followed by reaction with disulfides $R^iSSR^i$. Sulfides 21 can then be converted to the corresponding benzylamines 23 by oxidation to the sulfones then reduction to the benzylamines as was previously shown in Schemes 3 and 9.

Scheme 10

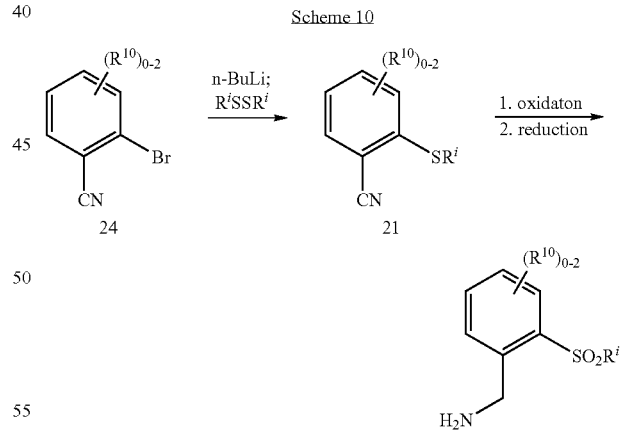

In addition, as shown in Scheme 11, sulfides 21 can also be prepared from o-cyanophenyldisulfides 25 by reaction with organometallic nucleophiles $R^iM$, for example, Grignard reagents. Sulfides 21 can then be converted to the corresponding benzylamines 23 by oxidation to the sulfones then reduction to the benzylamines as was previously shown in Schemes 3 and 9.

Scheme 11

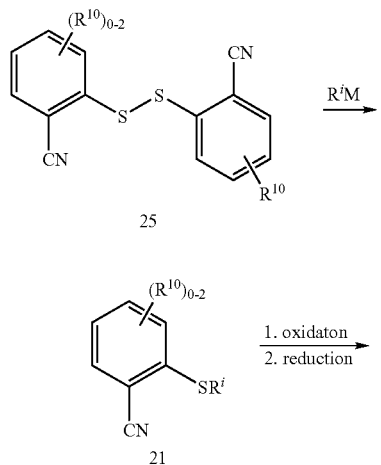

As shown in Scheme 12, sulfides 21 can also be prepared from o-fluorobenzonitriles 26 via reaction with R$^i$SH in a solvent such as DMF in the presence of a base such as sodium carbonate. Sulfides 21 can then be converted to the corresponding benzylamines 23 by oxidation to the sulfones then reduction to the benzylamines as was previously shown in Schemes 3 and 9. Also, sulfides 21 can be converted to benzylamines 27 by treatment with a reducing agent, such as BH$_3$.

Scheme 12

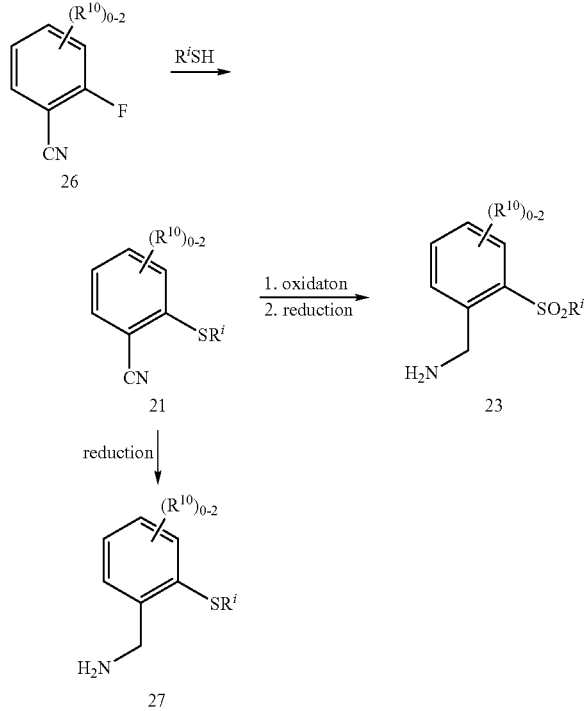

Finally, as shown in Scheme 13, sulfides 29 can be prepared from thiosalicylates 28 via alkylation with alkyl halides R$^i$X, followed by oxidation to the sulfones 30 as was previously shown in Scheme 9. The esters 30 can be converted to benzylamines 23 as was previously shown in Scheme 4 or Scheme 5.

Scheme 13

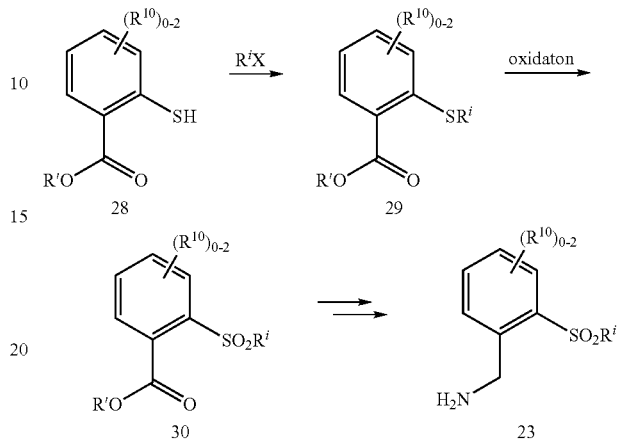

Benzylamines 33 containing a heterocyclic substituent can be prepared as shown in Scheme 14. Fluorobenzonitriles 26 are treated with amines 31 in a solvent such as acetonitrile. The resulting benzonitriles 32 are then converted to the benzylamines 33 as was previously shown in Scheme 3.

Scheme 14

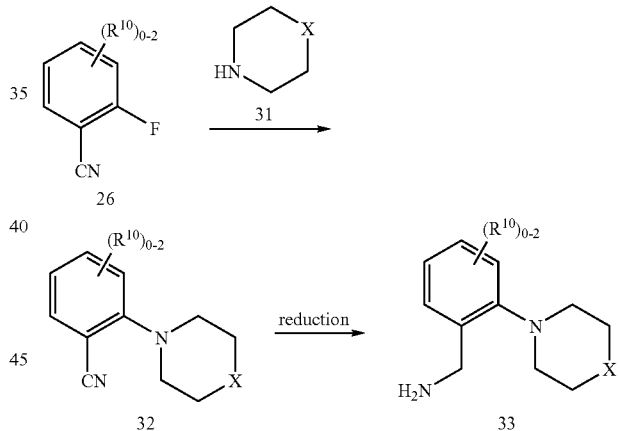

As shown in Scheme 15, benzylamines 37 containing an ortho-sulfonamide substituent can be prepared from o-cyano sulfonyl chlorides 34 via reaction with amines 35 (or amine hydrochloride salts) in the presence of a base, for example, TEA, in a solvent such as THF or water. Benzonitriles 36 can then be converted to the corresponding benzylamines 37 as was previously shown in Scheme 3.

Scheme 15

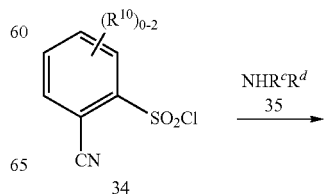

-continued

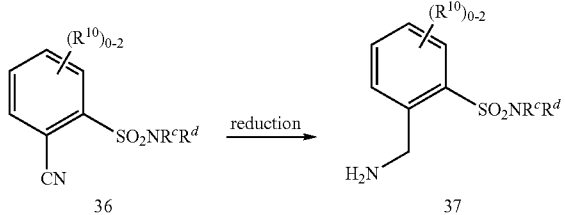

Benzylamines 40 containing an amide substituent can be derived from cyanobenzoic acids 38 as shown in Scheme 16, by treatment of acids 38 with amines 35 (or amine hydrochloride salts) in the presence of appropriate coupling reagents such as EDC, HOAT and a base such as DIEA. The derived benzonitriles 39 can then be converted to the benzylamines 40 as was previously shown in Scheme 3. Alternatively, amides 40 can be prepared as shown in Scheme 17 from isobenzofuran-1(3H)-ones 41 by treatment with amines 35 in the presence of trimethylaluminum. The derived benzyl alcohols 42 can then be converted to the corresponding benzylamines as was previously shown in Scheme 4.

Scheme 16

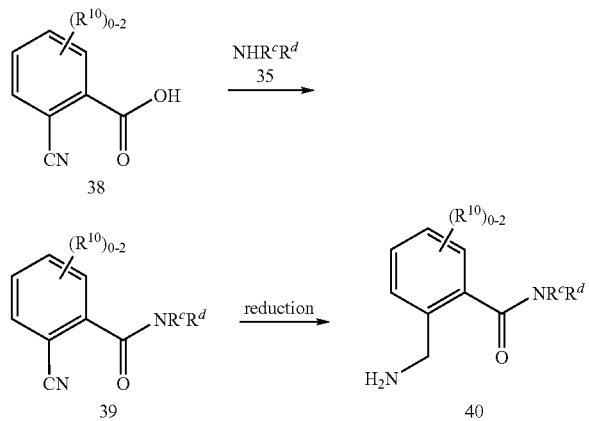

Scheme 17

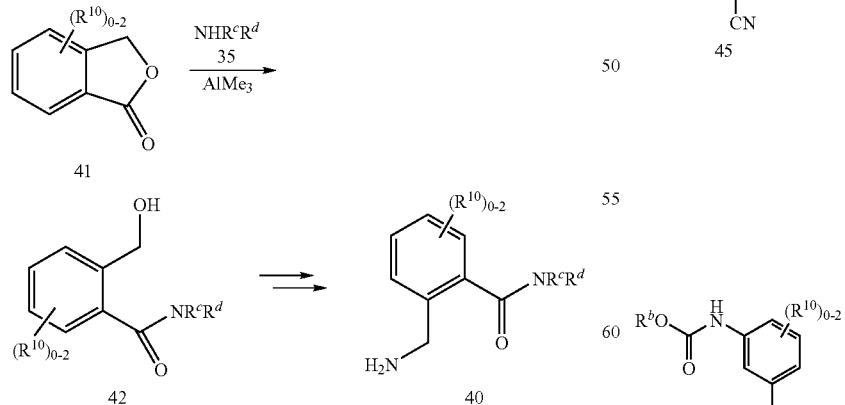

Benzylamines 44 containing an ortho-ether substituent can be prepared, as shown in Scheme 18, from phenols 41, via alkylation with alkyl halides 42. The derived benzonitriles 43 can then be converted to the corresponding benzylamines 44 as was previously shown in Scheme 3.

Scheme 18

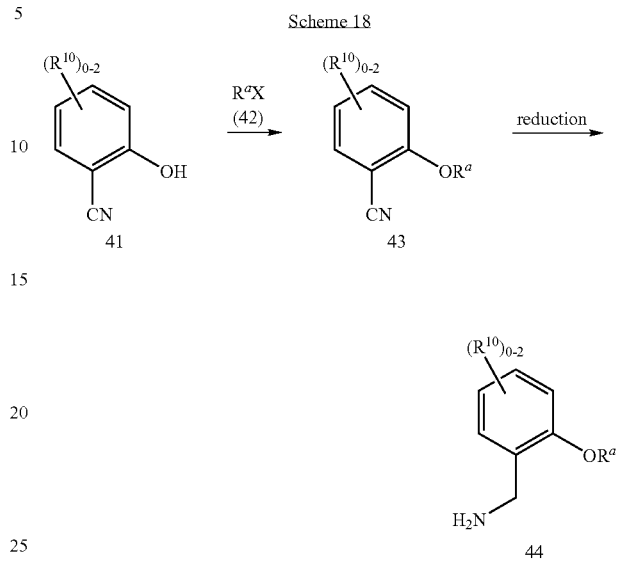

As exemplified in Scheme 19, functionalized benzylamines 48, 51 and 54 containing acetamide, urea or carbamate substituents can be prepared from nitro compounds 45 via reduction to the anilines 46 with, for example, iron in acetic acid. As exemplified in Scheme 20, anilines 46 can be treated with phosgene followed by amine 35 to provide ureas 47, or with anhydrides 49 to provide acetamides 50, or with alkyl chloroformates 52 to give carbamates 53. The benzonitrile products 47, 50 and 53 can then be converted to the desired benzylamines 48, 51 and 54 using methods previously shown in Scheme 3.

Scheme 19

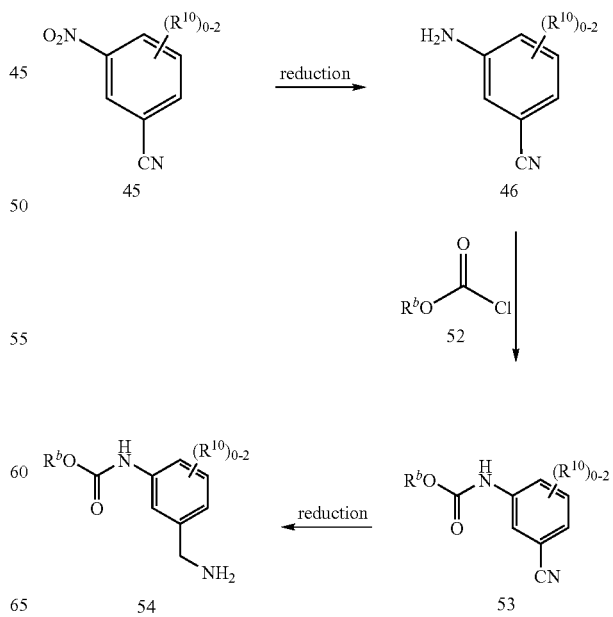

Scheme 20

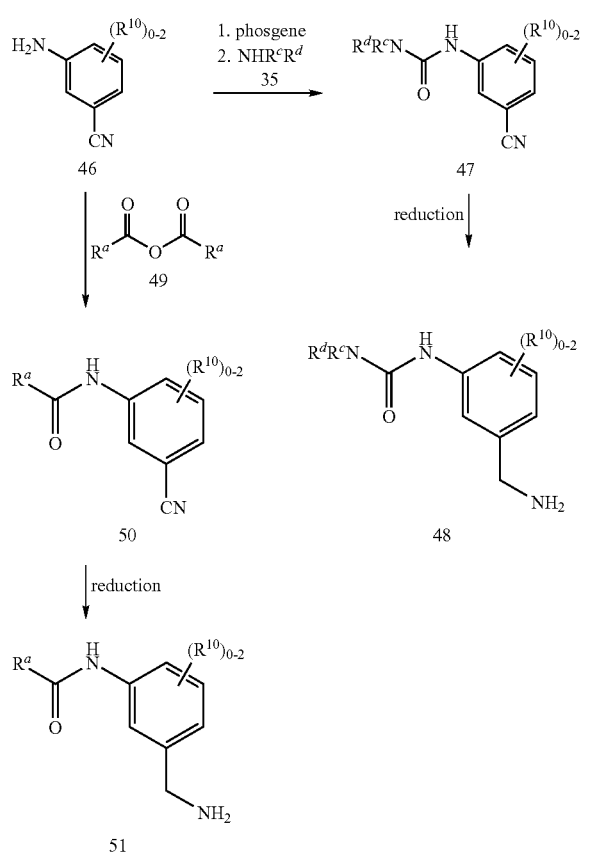

The compound of the instant invention herein described may have asymmetric centers. For example, the chiral carbon atom in Formula (I) as indicated below, exist in either as S or R configuration.

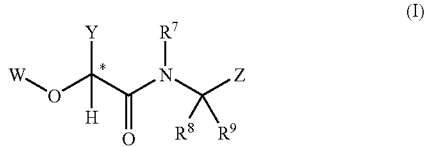
(I)

Thus, the stereoisomeric configurations of each compound of Formula (I), (II) or (III) are considered part of the invention. For example, but not limited to therein, in compounds of Formula (II), the following two stereoisomeric configurations are possible:

isomer-1

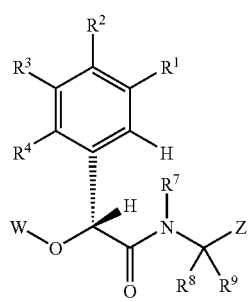

isomer-2

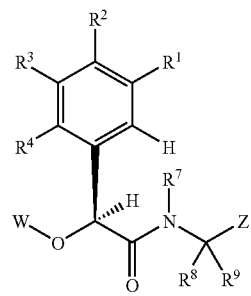

They are collectively, as well as individually, considered part of the invention. In a preferred stereoisomeric embodiment the present invention provides for a stereoisomeric configuration of isomer-1 for all embodiments of Formula (I), (II) or (III), or tautomer, pharmaceutically acceptable salt, solvate, or prodrug form thereof.

EXAMPLES

The following Examples have been prepared, isolated and characterized using the methods disclosed herein. The following Examples demonstrate a partial scope of the invention and are not meant to be limiting of the scope of the invention.

In the following experimental procedures, solution ratios express a volume relationship, unless stated otherwise. NMR chemical shifts (δ) are reported in parts per million. Flash chromatography (see Still, W. C. et al. *J. Org. Chem.* 1978, 43, 2923, for a description of the method) was carried out on ISCO CombiFlash™ systems using prepacked $SiO_2$ cartridges and eluting with gradients of the specified solvents. Reverse phase high pressure liquid chromatography (HPLC) was carried out on C18 HPLC columns using methanol/water gradients containing 0.1% trifluoroacetic acid.

Example 1

N-(2-(Cyclopropylsulfanyl)benzyl)-2-(1-aminoisoquinolin-6-yloxy)-2-(3-ethoxy-4-isopropoxyphenyl)-N-methylacetamide Trifluoroacetic Acid Salt

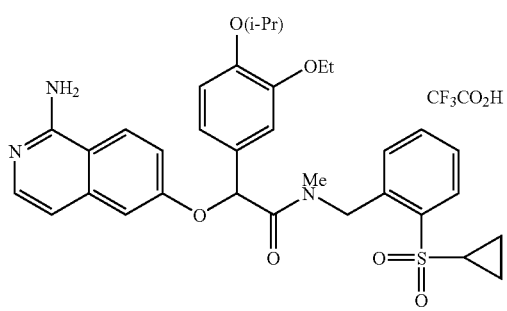

1A: 2-(Cyclopropylsulfanyl)benzonitrile

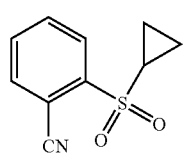

To 2,2'-dithio-bis(benzonitrile) (obtained from Sumitomo Seika) (2.00 g, 7.46 mmol) in THF (37 mL) at −78° C., a 0.5 M THF solution of cyclopropyl magnesium bromide (149 mL, 74.6 mmol) was added via addition funnel. After 10 min, the reaction was quenched with saturated aqueous ammonium chloride (200 mL). After warming to rt, the reaction product was diluted with water and ethyl acetate and the layers were separated. The organic layer was washed with water and brine, dried (MgSO$_4$), filtered and concentrated. The resulting residue was purified via silica gel chromatography eluting with 15% ethyl acetate/hexane to provide 2-(cyclopropylthio)benzonitrile as a yellow oil (1.36 g). The oil was dissolved in CH$_2$Cl$_2$, ~75% MCPBA (6.00 g, 26.1 mmol) was added and the reaction was stirred at rt for 2 h. 1N NaOH was added and the layers were separated. The organic layer was washed with 1N NaOH (3×) and brine (1×) then dried (MgSO$_4$), filtered and concentrated to provide 1A (1.50 g, 97% yield, 2 steps) as a white solid.

1B: (2-(Cyclopropylsulfanyl)phenyl)methanamine Hydrochloride Salt

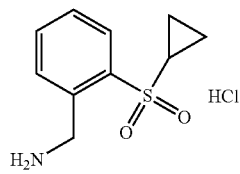

To 1A (1.50 g, 7.25 mmol) in refluxing THF (72 mL) was added a 2M THF solution of BH$_3$.SMe$_2$ (10.8 mL, 21.7 mmol). After heating at reflux for 2 h, the reaction was cooled to rt and 6M HCl (4.32 mL) was slowly added. The reaction was heated to reflux for 30 min, then cooled to rt, concentrated and azeotroped (3×) with THF/MeOH on a rotary evaporator. The resulting residue was taken up in THF and filtered to provide 1B (1.40 g, 79%) as a white solid. $^1$H NMR (400 MHz, CD$_3$OD) δ ppm 1.15 (m, 2H) 1.29 (m, 2H) 2.91 (m, 1H) 4.52 (s, 2H) 7.72 (m, J=7.69, 7.69 Hz, 2H) 7.80 (t, J=6.81 Hz, 1H) 8.04 (d, J=7.91 Hz, 1H).

1C: N-(2-(Cyclopropylsulfanyl)benzyl)-2,2,2-trifluoroacetamide

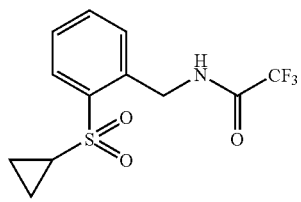

To 1B (1.16 g, 4.70 mmol) in CH$_2$Cl$_2$ (47 mL) at 0° C. was added DIPEA (1.60 mL, 9.40 mmol) followed by trifluoroacetic anhydride (3.30 mL, 23.5 mmol). After stirring (0° C. to rt) for 1.5 h, the reaction was concentrated. The resulting residue was dissolved in ethyl acetate, washed with water and brine, dried (MgSO$_4$), filtered and concentrated to provide 1C (1.68 g) as a yellow oil. LC-MS: 307.93 (M+H)$^+$.

1D: N-(2-(Cyclopropylsulfanyl)benzyl)-2,2,2-trifluoro-N-methylacetamide

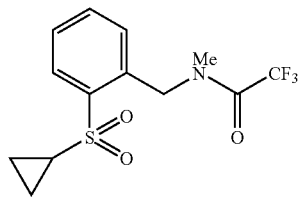

To 1C (1.68 g, 5.47 mmol) in CH$_3$CN (55 mL) was added potassium carbonate (1.13 g, 8.20 mmol), tetrabutylammonium bromide (88 mg, 0.27 mmol) and methyl iodide (3.40 mL, 54.7 mmol) and the reaction was heated to reflux overnight. After cooling to rt and concentrating, the remaining residue was dissolved in ethyl acetate and washed with water (3×) and brine. The organic layer was dried (MgSO$_4$), filtered and concentrated to provide 1D (1.50 g) as a yellow oil. LC-MS: 321.95 (M+H)$^+$.

1E: (2-(Cyclopropylsulfanyl)phenyl)-N-methyl-methanamine Hydrochloride

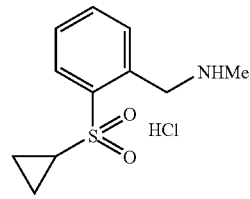

To 1D (1.50 g, 4.67 mmol) in MeOH (23 mL) and water (5 mL) was added potassium carbonate (3.20 g, 23.4 mmol) and the reaction was refluxed for 45 min. After cooling to rt, the mixture was filtered and the filtrate was concentrated. The resulting residue was dissolved in ethyl acetate and washed with water and brine. The aqueous layer was back-extracted with ethyl acetate (5×). The combined organic layers were dried (MgSO$_4$), filtered and concentrated to provide a yellow oil. The oil was dissolved in THF and 4N HCl in 1,4-dioxane (2.2 mL) was added. The resulting white solid was filtered to provide 1E (1.00 g). $^1$H NMR (400 MHz, CD$_3$OD) δ ppm 1.03-1.21 (m, 2H), 1.30 (ddd, J=7.14, 4.50, 4.17 Hz, 2H), 2.80 (s, 3H), 2.84-3.03 (m, 1H), 2.86-3.05 (m, 1H), 4.41-4.65 (m, 2H), 7.59-7.93 (m, 3H), 8.06 (d, J=7.91 Hz, 1H). LC-MS: 226.10 (M+H)$^+$.

1F: 4-Methoxy-2-methylbenzoic Acid

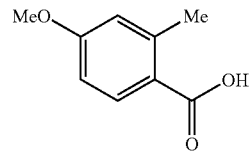

A flask equipped with a mechanical stirrer, reflux condenser and addition funnel was charged with magnesium (61.4 g) and THF (1 L) and put under a nitrogen atmosphere. The magnesium was treated with 4-bromo-3-methylanisole (500 g) and the reaction flask was warmed to 40° C. until reaction was well initiated. The remaining 4-bromo-3-methylanisole (9.5 kg) was added continuously over the next 1.5 h. The reaction temperature was maintained between 50-60° C. with an ice/water bath. The ice bath was removed during the last 10% of the addition. Once the last of the bromide was added, the reaction was allowed to stir for 1.5 h, during which time the temperature dropped to 35° C. At this point, there was very little unconsumed magnesium remaining, however the reaction solution was heated to 60° C. for 30 min to ensure completion. The reaction was cooled to −10° C. and excess carbon dioxide was added into the reaction mixture through the condenser. The reaction became quite thick, and the temperature rose to ~30° C. At this point an additional 1 L of THF was added. The carbon dioxide was added until the reaction was complete and the temperature began to drop. A total of 350 mL THF was removed under reduced pressure. The resulting thick slurry was quenched with a mixture of 4.4 L ice cold water and 320 mL concentrated HCl. To the resulting thick white slurry an additional 4 L water was added. The resulting precipitate was filtered and washed with 1.5 L water, dried on the funnel overnight, and dried at 60° C. under high vacuum to provide 386.05 g of 1F as a white powder. HPLC showed a peak at the expected retention time 15.67 min and a purity of 97.45% at 220 nm, and 98.98% at 254 nm.

1G: 4-Methoxy-2-methylbenzamide

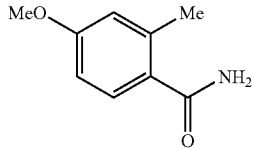

A mixture of 1F (386.05 g) in $CH_2Cl_2$ (3 L) was combined in a flask equipped with a mechanical stirrer, reflux condenser and addition funnel to provide a very thick slurry. DMF (1 mL) was added as catalyst, followed by oxalyl chloride (330 g) dropwise over about 2 h. The acidic effluent gasses were scrubbed through a $K_2CO_3$ scrubber. The slurry slowly dissolved during the addition to provide a red solution of acid chloride. $CH_2Cl_2$ (1.3 L) was removed at 30° C. with slight vacuum, and the resulting concentrated solution of acid chloride was polish filtered through a course sintered glass funnel to remove some insoluble matter. This filtered solution was concentrated to a crystalline residue and pumped down under high vacuum for 30 min to remove any excess oxalyl chloride. The crystalline residue was dissolved in THF (550 mL) and titrated into a large flask containing ice cold concentrated ammonium hydroxide (1 L) over ~15 min. The temperature quickly rose to ~30° C. with the formation of a thick slurry of product. To this oily slurry of product, water (3 L) was added over ~15 min to provide a thick white slurry of product. This product was filtered over course sintered glass and washed with water (1.5 L) and dried under nitrogen/vacuum for 36 h. 367.8 g of 1G was isolated as an off-white solid. HPLC showed a peak at the expected retention time of 11.85 min, with a purity of 95.15% at 220 nm, and 97.29% at 254 nm.

1H: 4-Methoxy-2-methylbenzoyl(N,N-dimethyl)formamidine

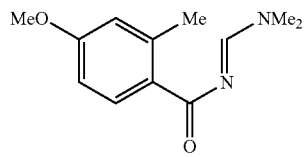

1G (296.15 g, 1.794 mol) was dissolved in THF (1.5 L) in a flask equipped with a mechanical stirrer and distillation head to give a thick slurry. DMF-DMA (263 mL, 1.1 eq) was added in one portion and slowly heated to gentle reflux. After 30 min at reflux, the reaction mixture became a homogeneous solution. The reaction was maintained at reflux for 1.5 h, and checked by HPLC and TLC (10:1 $CH_2Cl_2$/MeOH). At atmospheric pressure, 1150 mL THF was distilled out and replaced with 1500 mL heptane (Note that if the solution is not quite saturated, remaining THF should be removed by distillation). The remaining solution was cooled slowly to rt overnight with stirring, seeded at 68° C. Rapid crystallization was observed. The resulting slurry was cooled to 0° C., filtered and washed with heptanes (500 mL) and dried under vacuum at rt for 48 h. 384.6 g (97.4%) of 1H was isolated as a light tan crystalline solid. HPLC-MS using a neutral buffer ammonium acetate buffer system showed only a single peak, with the expected mass.

1I: 6-Methoxyisoquinolin-1-ol

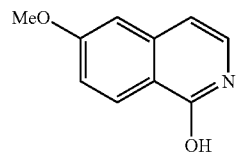

A slurry of 1H (16.33 g) in a small amount of THF (25 mL) was heated to 60° C. in a flask equipped with a stir bar, reflux condenser, and addition funnel. A solution of 1M potassium tert-butoxide in THF (105 mL) was titrated in over a period of 30 min. The reaction turned a light yellow, and began to precipitate a solid product after about 10 min and became a thick suspension after 30 min. The reaction was cooled to ~30° C. and neutralized to pH 7 with 9.5 mL conc. HCl. Water (about 25 mL) was added to dissolve all the salts, and still an easy phase split remained. The phases were split and the aqueous phase was back extracted with 25 mL ethyl acetate. The organic phases were combined and slowly concentrated at 60° C. to provide a crystalline residue. 12.16 g (93.6%) of 1I was isolated as a light orange solid. An analytical sample was prepared by recrystallization from ethyl acetate. LC retention time=13.533 min. $^1$H NMR (DMSO-$d_6$) δ 3.86 (s, 3H); 6.46 (d, 1H); 7.02-7.13 (m, 3H); 8.08 (d, 1H); 11.03 (s, 1H).

1J: 1-Chloro-6-methoxyisoquinoline

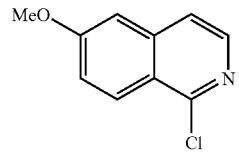

A slurry of 6-methoxyisoquinolone (116 g, 662 mmol) in phosphorous oxychloride (200 mL, 2.14 mol) was charged to a rotavap flask. The resulting thick paste was heated on the rotovap to 90° C. for ~30 min. The reaction thinned to a thick black solution with gas evolution then became pasty again, and was heated continuously at 90° C. for an additional 30 min and checked by TLC. An additional quantity of phosphorous oxychloride (100 mL, 1.07 mol) was added and the reaction was heated continuously for another 2 h. The reaction was complete (checked by TLC; complete consumption of starting material with some production of a polar impurity) so the excess $POCl_3$ was removed under high vacuum to leave a solid mass of crude product. This solid mass was triturated with ethyl acetate (500 mL) at 0° C. for 3.5 h. The solid product was filtered and washed with cold ethyl acetate (250 mL). Mother liquors contained essentially no product and were discarded. The weight of this crude solid salt was ~208 grams. This salt was dissolved in a mixture of cold ethyl acetate (1000 mL) and water (1000 mL) and neutralized to pH=6.75 with $NaHCO_3$ (209 g, 2.49 mol, 3.75 eq based on starting material). The phases were split, and the aqueous phase was back extracted with ethyl acetate (500 mL) and combined with the first product containing the ethyl acetate phase. The ethyl acetate was removed under reduced pressure to yield 110.8 g crude residue. In order to remove the polar impurity, this residue was dissolved in a mixture of ethyl acetate 200 mL and heptanes 100 mL and passed through a silica gel plug (500 g) and eluted with a mixture of ethyl acetate/heptanes 1:1. The product containing fractions was concentrated to a residue to provide pinkish-yellow solids. These solids were recrystallized from hot (~75° C.) heptanes (1000 mL) and cooled to rt then to 0° C. Filtration and washing with cold heptanes (250 mL) followed by drying under vacuum provided purified 1J as a off-white crystalline solid. (98.02 g, 506 mmol, 76.5%).

1K: 6-Methoxyisoquinolin-1-amine

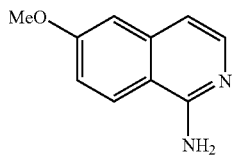

A sealable tube was charged with 1J (770 mg, 3.98 mmol), copper (I) oxide (30 mg) and ~12M ammonia in ethylene glycol (5 mL). The tube was sealed and the reaction was heated to 120° C. for 72 h. After cooling to rt, the reaction was diluted with methanol and was purified via preparative HPLC (MeOH/water/TFA) to provide 1K (832 mg, 72%). LC-MS: 175.23 $(M+H)^+$.

1L: 1-Aminoisoquinolin-6-ol

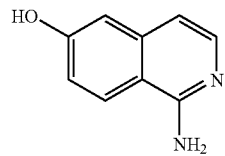

To 1K (345 mg, 2.0 mmol) in $CH_2Cl_2$ (10 mL) at 0° C. was added boron tribromide (8.0 mL, 1M solution in $CH_2Cl_2$). After warming to rt and stirring overnight, the reaction was concentrated and purified via preparative HPLC (MeOH/water/TFA) to provide 1-aminoisoquinolin-6-ol trifluoroacetic acid salt (240 mg, 44%). LC-MS: 161.2 $(M+H)^+$. The product (83 mg, 0.30 mmol) was dissolved in methanol (10 mL), and dianion WA21J Resin (2 g) was added. After stirring for 1 h, the reaction was filtered to provide the free amine 1 L (41 mg, 85%). LC-MS: 161.18 $(M+H)^+$.

1M: Benzyl 2-(1-aminoisoquinolin-6-yloxy)-2-(3-ethoxy-4-isopropoxyphenyl)acetate Trifluoroacetic Acid Salt

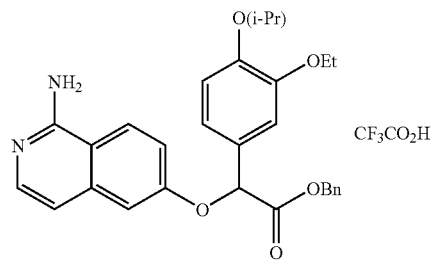

A mixture of 1 L (93 mg, 0.58 mmol) in DMF (5 mL) and 60% NaH (32 mg, 0.80 mmol) was stirred for 20 min. To this mixture was added chloro-(3-ethoxy-4-isopropoxy-phenyl)-acetic acid benzyl ester (WO 2004072101) (265 mg, 0.73 mmol) in DMF (2 mL). After stirring for 1 h, the reaction was diluted with ethyl acetate, washed with water and brine then dried ($Na_2SO_4$), filtered and concentrated. The resulting residue was purified via preparative HPLC (MeOH/water/TFA) to provide 1M (160 mg, 46%). LC-MS: 487.25 $(M+H)^+$.

1N: 2-(1-Aminoisoquinolin-6-yloxy)-2-(3-ethoxy-4-isopropoxyphenyl)acetic Acid Trifluoroacetic Acid Salt

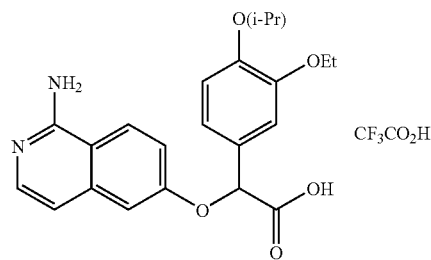

To 1M (131 mg, 0.22 mmol) in THF (8 mL) was added 10% Pd/C (cat.) and the mixture was hydrogenated at 50 psi for 3 h, then at 60 psi for 2 h. The reaction was filtered and concentrated to provide 1N (85 mg, 76%). LC-MS 397.10 $(M+H)^+$.

1O: Example 1

A mixture of 1N (8.0 mg, 0.016 mmol), 1E (11 mg, 0.042 mmol), EDCI (8.0 mg, 0.040 mmol), HOAT (3.0 mg, 0.022 mmol), DIEA (0.02 mL, 0.11 mmol) in $CH_2Cl_2$ (1 mL) and DMF (0.5 mL) was stirred at rt overnight. The reaction was diluted with brine and ethyl acetate, and the layers were separated. The organic layer was concentrated and purified via preparative HPLC (MeOH/H$_2$O/TFA) to provide Example 1 (5 mg, 46%). $^1$H NMR (400 MHz, methanol-d$_4$) δ ppm (rotamers present) 0.96-1.46 (m, 13H) 2.75-2.93 (m, 1H) 3.03, 3.19 (s, 3H) 3.95-4.14 (m, 2H) 4.45, 4.62 (pent., J=6.15 Hz, 1H) 5.14 (dd, 2H) 5.31 (s, 1H) 6.38, 6.49 (s, 1H) 6.81-7.53 (m, 10H) 7.84-7.99 (m, 1H) 8.27, 8.34 (d, J=9.23 Hz, 1H). LC-MS: 604.28 (M+H)$^+$.

Example 2

N-(2-(Cyclobutylsulfanyl)benzyl)-2-(1-aminoisoquinolin-6-yloxy)-2-(3-ethoxy-4-isopropoxyphenyl)acetamide Trifluoroacetic Acid Salt

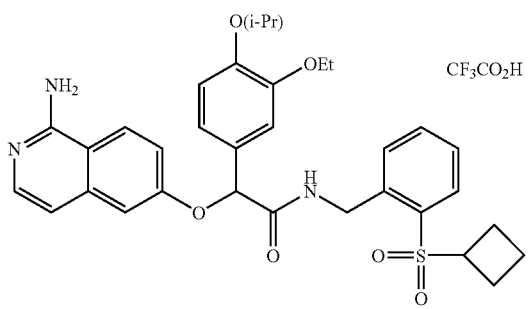

2A: Methyl 2-(cyclobutylsulfanyl)benzoate

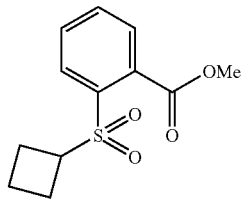

To methylthiosalicylate (3.92 mL, 28.5 mmol) in DMF at 0° C. was added triethylamine (3.97 mL, 28.5 mmol) then cyclobutyl bromide (5.00 g, 37.0 mmol). The ice bath was removed and the reaction was stirred at rt for 1 h then heated to 50° C. overnight. After cooling to rt, diethyl ether was added and the mixture was filtered. The filtrate was diluted with ethyl acetate, then washed with water (6×) and brine (1×). The organic layer was dried (MgSO$_4$), filtered and concentrated to provide a yellow oil. The yellow oil was dissolved in CH$_2$Cl$_2$ (143 mL) and MCPBA (~75%, 19.7 g, ca. 85.5 mmol) was added. The reaction was stirred for 2.5 h, then was cooled to 0° C. 1 N NaOH was added, and the reaction was stirred for 5 min. The layers were separated, and the organic layer was washed with 1 N NaOH (2×). The aqueous layer was back-extracted with CH$_2$Cl$_2$. The combined organic layers were washed with brine, dried (MgSO$_4$), filtered and concentrated to provide 2A as a clear oil (7.20 g). LC-MS: 255.01 (M+H)$^+$.

2B: 2-(Cyclobutylsulfanyl)benzoic Acid

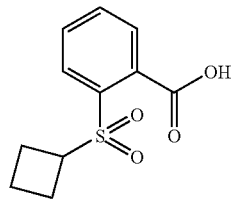

To 2A (7.20 g, 28.3 mmol) in THF (190 mL) was added 1 N LiOH (94 mL). The reaction was stirred for 1 h at rt, then was heated gradually to 65° C. After cooling to rt, the THF was removed under reduced pressure. The remaining solution was cooled to 0° C. and acidified to pH 1 with 1N HCl. The product was extracted with CH$_2$Cl$_2$, and the organic layer was washed with brine, dried (MgSO$_4$), filtered and concentrated to provide 2B as a clear oil (6.30 g). LC-MS: 241.08 (M+H)$^+$.

2C: 2-(Cyclobutylsulfanyl)benzamide

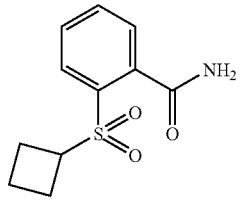

To 2B (6.30 g, 26.2 mmol) in DMF (52.5 mL) was added HOBT.H$_2$O (4.9 g, 32.0 mmol) and EDC (5.98 g, 31.3 mmol). After stirring 1 h at rt, the reaction was cooled to 0° C. and 25% ammonium hydroxide was added. The reaction was stirred for 1.5 h and was then diluted with ethyl acetate/THF and washed with 1N HCl (2×) and 1 N NaOH (2×). The aqueous layer was back-extracted with ethyl acetate. The combined organic layers were washed with brine, dried (MgSO$_4$), filtered and concentrated to provide 2C (5 g) as a yellow solid. LC-MS: 240.08 (M+H)$^+$.

2D: (2-(Cyclobutylsulfanyl)phenyl)methanamine Hydrochloride

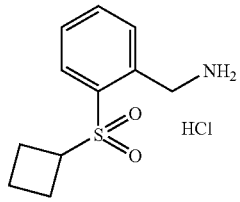

To 2C (5.00 g, 20.9 mmol) in THF (80 mL) at reflux was added a 1M THF solution of BH$_3$.THF (63 mL, 62.7 mmol) via an addition funnel, dropwise over 20 min. After refluxing for 6 h, additional BH$_3$.THF solution was added (20 mL) and refluxing continued overnight. After cooling to rt, 6N HCl (12.5 mL) was added and the reaction was heated again to reflux for 1 h. The reaction was cooled to rt, concentrated then azeotroped (3×) with MeOH/THF. After drying under vacuum for 1 h, the resulting residue was taken up in THF and filtered to provide 2D as a white solid. $^1$H NMR (400 MHz, CD$_3$OD) δ ppm 1.94-2.11 (m, 2H), 2.13-2.26 (m, 2H), 2.43-2.61 (m, 2H), 4.11-4.23 (m, 1H), 4.43 (s, 2H), 7.66-7.76 (m, 2H), 7.81 (t, J=6.81 Hz, 1H), 8.03 (d, J=6.15 Hz, 1H). LC-MS: 226.11 (M+H)$^+$.

2E: Example 2

A mixture of 1N (10 mg, 0.020 mmol), 2D (10 mg, 0.038 mmol), EDCI (10 mg, 0.050 mmol), HOAT (3.0 mg, 0.022 mmol), DIEA (0.02 mL, 0.11 mmol) in DMF (1 mL) was stirred at 60° C. for 2 h. The reaction was diluted with brine and ethyl acetate, and the layers were separated. The organic layer was concentrated and purified via preparative HPLC (MeOH/H$_2$O/TFA) to provide Example 2 (8.6 mg, 60%). $^1$H NMR (400 MHz, CD$_3$OD) δ ppm 1.22 (d, J=6.15 Hz, 6H) 1.30 (t, J=7.03 Hz, 3H) 1.83-1.97 (m, 2H) 1.98-2.15 (m, 2H) 2.29-2.49 (m, 2H) 3.89-4.00 (m, 2H) 4.05-4.23 (m, J=8.20 Hz, 1H) 4.39-4.53 (m, J=6.15 Hz, 1H) 4.61-4.74 (m, 2H) 5.83 (s, 1H) 6.90 (d, J=8.35 Hz, 1H) 6.96 (d, J=7.47 Hz, 1H) 7.01-7.10 (m, 2H) 7.21 (d, J=2.64 Hz, 1H) 7.30 (d, J=8.79 Hz, 1H) 7.34-7.47 (m, 3H) 7.78 (dd, J=7.47, 1.76 Hz, 1H) 8.27 (d, J=9.23 Hz, 1H) 8.75 (t, J=5.93 Hz, 1H). LC-MS: 604.43 (M+H)$^+$.

Example 3

N-(3-Acetylamino-benzyl)-2-(1-aminoisoquinolin-6-yloxy)-2-(3-ethoxy-4-isopropoxy-phenyl)-acetamide Trifluoroacetic Acid Salt

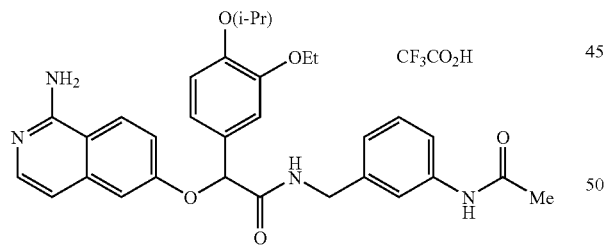

Example 3 (7.2 mg, 55%) was prepared from 1N (10 mg, 0.020 mmol) and commercially available N-(3-(aminomethyl)phenyl)acetamide HCl salt (8 mg, 0.04 mmol) following a procedure analogous to the preparation of Example 2. $^1$H NMR (400 MHz, CD$_3$OD) δ ppm 1.29 (d, J=5.71 Hz, 6H) 1.37 (t, J=6.81 Hz, 3H) 2.08 (s, 3H) 3.95-4.05 (m, 2H) 4.30-4.45 (m, 2H) 4.47-4.60 (m, 1H) 5.83 (s, 1H) 6.89 (d, J=7.91 Hz, 1H) 6.97 (dd, J=12.52, 7.69 Hz, 2H) 7.08-7.20 (m, 3H) 7.25 (d, J=2.20 Hz, 1H) 7.34 (d, J=8.35 Hz, 1H) 7.41-7.54 (m, 3H) 8.32 (d, J=9.23 Hz, 1H) 9.05 (t, J=6.15 Hz, 1H). LC-MS: 543.4 (M+H)$^+$.

Example 4

N-(2-(3,5-Diethyl-1H-pyrazol-1-yl)benzyl)-2-(1-aminoisoquinolin-6-yloxy)-2-(3-ethoxy-4-isopropoxyphenyl)acetamide Ditrifluoroacetic Acid Salt

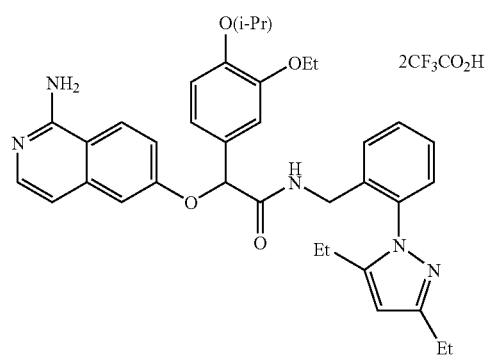

4A: N-(3-Aminobenzyl)-2,2,2-trifluoroacetamide

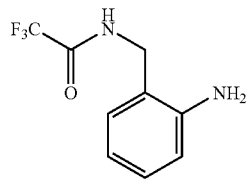

2-Aminobenzylamine (1.5 Kg, 12.28 mol) was charged to 1.5 L tBME and slurried. Heptanes (13.5 L) were charged to bring the solvent ratio to 10% v/v tBME/heptanes. Ethyl trifluoroacetate (1.6 L, 1.9 Kg, 13.5 mol) was added slowly to the reaction at 25±5° C. over 27 min. Visually this reaction went from a gray or off-white slurry to a bright white slurry of fine crystals. The reaction was stirred for 1 h at ambient temperature. The product was filtered and washed with 1.2 L of heptanes then dried by drawing nitrogen through the wet cake overnight to provide 4A (2255 g).

4B: N-(2-(3,5-Diethyl-1H-pyrazol-1-yl)benzyl)-2,2,2-trifluoroacetamide

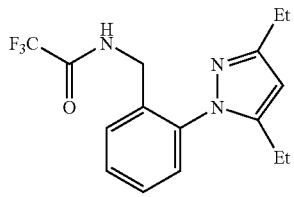

To N-(3-aminobenzyl)-2,2,2-trifluoroacetamide (1.00 g, 4.60 mmol) in conc. HCl (9.2 mL) at 0° C. was added sodium nitrite (481 mg, 6.97 mmol) in cold water (4 mL), dropwise. After stirring at the same temperature for 30 min, tin (II) chloride dihydrate (3.11 g, 13.8 mmol) in cold conc. HCl (4.5 mL) was slowly added and the ice bath was removed. After stirring for 45 min, 2,4-heptadiene (1.18 g, 9.20 mmol) and acetonitrile (1 mL) were added. After 1 h, the reaction was filtered through Celite® washing with ethyl acetate and methylene chloride then concentrated. The residue was dissolved in ethyl acetate and washed with water (2×) and brine (1×). The aqueous layer was back-extracted with ethyl acetate, and the combined organic layers were dried (MgSO$_4$), filtered and concentrated. The resulting residue was purified via silica gel chromatography eluting with 0-50% ethyl acetate/hexanes to provide 4B (280 mg) as a yellow oil. LC-MS: 326.09 (M+H)$^+$.

4C: (2-(3,5-Diethyl-1H-pyrazol-1-yl)phenyl)methanamine Hydrochloride

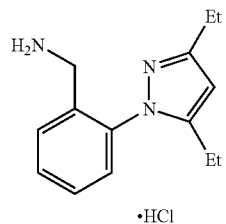

To 4B (140 mg, 0.43 mmol) in MeOH (2 mL) and water (0.30 mL) was added potassium carbonate (297 mg, 2.15 mmol) and the reaction was heated to 80° C. for 2 h. After cooling to rt, the reaction was concentrated and the residue was partioned between ethyl acetate and water. The aqueous layer was back-extracted with ethyl acetate (4×), and the combined organic layers were dried (MgSO$_4$), filtered and concentrated. The residue was diluted with diethyl ether and 4M HCl/dioxane (180 μL) was added. The resulting solid was filtered, and the hygroscopic solid was collected by dissolving in MeOH and concentrating to provide 4C (99 mg) as a yellow oil.

4D: Example 4

Example 4 (9.8 mg, 75%) was prepared from 1N (8.0 mg, 0.016 mmol) and 4C (8 mg, 0.091 mmol) following a procedure analogous to the preparation of Example 2. $^1$H NMR (400 MHz, CD$_3$OD) δ ppm 1.11 (t, J=7.69 Hz, 3H) 1.23 (t, J=7.69 Hz, 3H) 1.29 (d, J=6.15 Hz, 6H) 1.37 (t, J=6.81 Hz, 3H) 2.40 (q, J=7.47 Hz, 2H) 2.62 (q, J=7.62 Hz, 2H) 4.01 (q, J=7.03 Hz, 2H) 4.07 (s, 2H) 4.44-4.61 (m, 1H) 5.85 (s, 1H) 6.14 (s, 1H) 6.96 (d, J=8.35 Hz, 1H) 7.05 (d, J=7.03 Hz, 1H) 7.11 (dd, J=8.35, 1.76 Hz, 1H) 7.16 (d, J=2.20 Hz, 1H) 7.25 (t, J=8.79 Hz, 2H) 7.28-7.33 (m, 2H) 7.32-7.41 (m, 2H) 7.45-7.52 (m, 2H) 8.34 (d, J=9.23 Hz, 1H). LC-MS: 608.50 (M+H)$^+$.

Example 5

N-(5-Acetylamino-2-ethanesulfonyl-benzyl)-2-(1-aminoisoquinolin-6-yloxy)-2-(3-ethoxy-4-isopropoxy-phenyl)-acetamide Trifluoroacetic Acid Salt

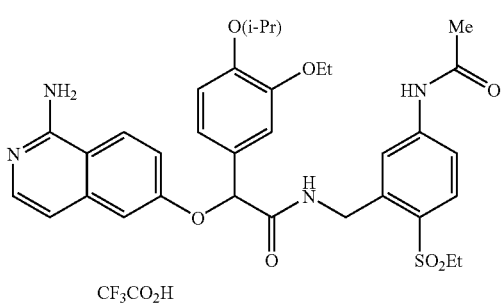

5A: 2-(Ethylthio)-5-nitrobenzonitrile

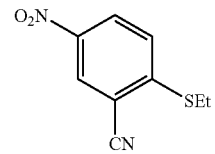

To 2-fluoro-5-nitrobenzonitrile (5.00 g, 30.1 mmol) in DMF (100 mL), triethylamine (9.30 mL, 66.7 mmol) was added and followed by ethanethiol (2.80 mL, 37.9 mmol). After stirring at rt for 1 h, the reaction mixture was poured into water (500 mL). The resulting precipitate was filtered and dried on high vacuum overnight to provide 5A (6.08 g, 97%).

5B: 2-(Ethylsulfonyl)-5-nitrobenzonitrile

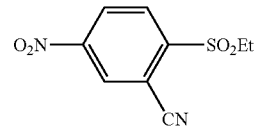

To 5A (6.08 g, 29.2 mmol) in CH$_2$Cl$_2$ (100 mL), ~75% MCPBA (16.0 g, 69.5 mmol) was added. After stirring at rt overnight, the reaction product was washed with saturated aqueous NaHCO$_3$, 1M H$_3$PO$_4$ and brine then dried (Na$_2$SO$_4$), filtered and concentrated. The resulting residue was purified via silica gel chromatography eluting with 10-35% ethyl acetate/hexane to provide 5B (6.20 g, 88%). LC-MS: 209.20 (M+H)$^+$.

5C: N-(3-Cyano-4-(ethylsulfonyl)phenyl)acetamide

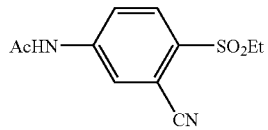

To 5B (3.60 g, 15.0 mmol) in 1:1 acetic acid/acetic anhydride (150 mL), Fe (4.20 g, 75.2 mmol) was added. The reaction mixture was heated to 100° C. for 2 h then poured into ice. After the ice melted, the product was extracted with ethyl acetate, and the organic layer was washed with saturated aqueous NaHCO$_3$ and brine. The organic layer was dried (Na$_2$SO$_4$), filtered and concentrated to provide 5C (3.14 g, 83%). LC-MS: 241.18 (M+H)$^+$.

5D: N-(3-(Aminomethyl)-4-(ethylsulfonyl)phenyl) acetamide

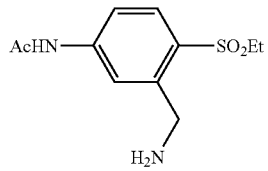

To 5C (423 mg, 1.65 mmol) in MeOH (17 mL), Raney Ni (cat) was added. The mixture was stirred under hydrogen (60 psi) for 8 h, then filtered and concentrated to provide 5D (397 mg, 92%). LC-MS: 253.23 (M+H)$^+$.

5E: Example 5

Example 5 (9.8 mg, 59%) was prepared from 1N (11 mg, 0.022 mmol) and 5D (23 mg, 0.091 mmol) following a procedure analogous to the preparation of Example 1. $^1$H NMR (400 MHz, CD$_3$OD) δ ppm 1.16 (t, J=7.25 Hz, 3H) 1.25 (d, J=6.15 Hz, 6H) 1.33 (t, J=7.03 Hz, 3H) 2.09 (s, 3H) 3.25-3.29 (m, 2H) 3.89-4.01 (m, 2H) 4.42-4.54 (m, 1H) 4.67 (d, J=4.83 Hz, 2H) 5.85 (s, 1H) 6.91 (d, J=8.79 Hz, 1H) 6.96 (d, J=7.03 Hz, 1H) 7.04-7.13 (m, 2H) 7.21 (d, J=2.20 Hz, 1H) 7.36-7.48 (m, 2H) 7.59 (dd, J=8.79, 2.20 Hz, 1H) 7.69-7.80 (m, 2H) 8.28 (d, J=9.23 Hz, 1H) 8.78 (t, J=6.15 Hz, 1H). LC-MS: 635.28 (M+H)$^+$.

Example 6

N-(5-Acetylamino-2-ethanesulfonyl-benzyl)-2-(1-aminoisoquinolin-6-yloxy)-2-(3,4-dimethoxy-phenyl)-acetamide Trifluoroacetic Acid Salt

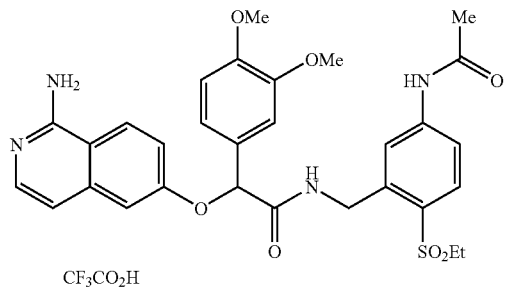

6A: 2-(3,4-Dimethoxyphenyl)-2-hydroxyacetonitrile

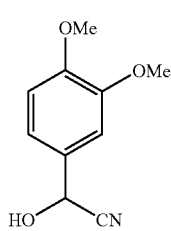

To 3,4-dimethoxybenzaldehyde (1.66 g, 10 mmol) in ethyl acetate (20 mL) was added NaHSO$_3$ (5.2 g, 50 mmol) in water (20 mL), followed by potassium cyanide (3.26 g, 50 mmol) in water (20 mL). The mixture was stirred overnight at rt, then warmed to 50° C. for 6 h. The reaction was cooled to rt, diluted with ethyl acetate, and the layers were separated. The organic layer was washed with brine, dried (Na$_2$SO$_4$), filtered and concentrated. The resulting residue was purified via silica gel chromatography (0-50% ethyl acetate/hexanes) to provide 6A (1.25 g, 65%) and starting material, 3,4-dimethoxybenzaldehyde (0.52 mg). 6A: LC-MS: 176.22 (M–H$_2$O)$^+$.

6B: Methyl 2-(3,4-dimethoxyphenyl)-2-hydroxyacetate

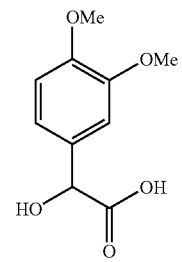

To 2-(3,4-dimethoxyphenyl)-2-hydroxyacetonitrile (1.25 g, 6.48 mmol) in ether (20 mL) and MeOH (1.5 mL) at –10° C. was added 4N HCl in dioxane (6 mL, 24 mmol). The reaction was stirred at –10° C. for 1 h, then stored at 4° C. for 2 days. The reaction was filtered, and washed with ether. The solid was dissolved in water (15 mL) and CH$_2$Cl$_2$ (15 mL) and stirred for 1 h. The layers were separated, and the aqueous layer was extracted with CH$_2$Cl$_2$ (3×20 mL), dried (Na$_2$SO$_4$), filtered and concentrated. The resulting residue was purified via silica gel chromatography (0-60% ethyl acetate/hexanes) to provide 6B (1.35 g, 92%). LC-MS: 249.16 (M+Na)$^+$.

6C: 2-(3,4-Dimethoxyphenyl)-2-hydroxyacetic Acid

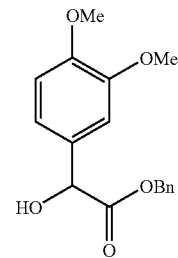

6B (890 mg, 3.9 mmol) was dissolved in THF (6 mL). 1M LiOH (6 mL) was added, and the reaction was stirred at rt for 1 h. The solvent was removed under reduced pressure, and water (10 mL) was added. The solution was acidified with 1 N HCl, then extracted with ethyl acetate (3×20 mL). The organic layer was concentrated to provide 6C (830 mg, 100%). LC-MS: 235.11 (M+Na)$^+$.

6D: Benzyl 2-(3,4-dimethoxyphenyl)-2-hydroxyacetate

To 6C (830 mg, 3.9 mmol) in DMF (15 mL) was added cesium carbonate (2.6 g, 8.0 mmol) followed by benzyl bromide (0.6 mL, 5 mmol). After stirring at rt overnight, the reaction was diluted with water, and was extracted with ethyl acetate (2×30 mL). The organic layer was washed with brine, dried (Na$_2$SO$_4$), filtered and concentrated. The resulting residue was purified via silica gel chromatography (0-40% ethyl acetate/hexanes) to provide 6D (520 mg, 44%). LC-MS 445.31 (M+H)$^+$.

6E: Benzyl 2-chloro-2-(3,4-dimethoxyphenyl)acetate

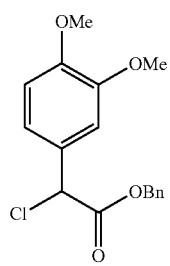

To 6D (450 mg, 1.5 mmol) in CH$_2$Cl$_2$ (5 mL) at 0° C. was added triethylamine (0.42 mL, 3.0 mmol) followed by mesyl chloride (0.14 mL, 1.8 mmol). After stirring at rt overnight, the reaction was concentrated and purified via silica gel chromatography (0-25% ethyl acetate/hexanes) to provide 6E (268 mg, 56%). $^1$H NMR (400 MHz, CD$_3$OD) δ ppm 3.81 (s, 3H) 3.87 (s, 3H) 5.19 (m, 2H) 5.36 (s, 1H) 6.81 (d, J=8.35 Hz, 1H) 6.93-7.07 (m, 2H) 7.20-7.42 (m, 5H).

6F: Benzyl 2-(1-aminoisoquinolin-6-yloxy)-2-(3,4-dimethoxyphenyl)acetate Trifluoroacetic Acid Salt

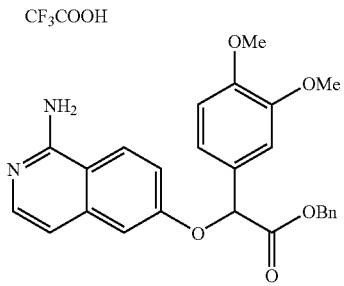

A mixture of 1-aminoisoquinolin-6-ol (1L) (30 mg, 0.19 mmol) in DMF (1 mL) and 60% NaH (10 mg, 0.25 mmol) was stirred for 10 min. To this mixture was added 6E (80 mg, 0.25 mmol) in DMF (1 mL). After stirring for 1 h, the reaction was diluted with ethyl acetate, washed with water and brine then dried (Na$_2$SO$_4$), filtered and concentrated. The resulting residue was purified via preparative HPLC (MeOH/water/TFA) to provide 6F (60 mg, 69%). LC-MS: 445.31 (M+H)$^+$.

6G: 2-(1-Aminoisoquinolin-6-yloxy)-2-(3,4-dimethoxyphenyl)acetic Acid

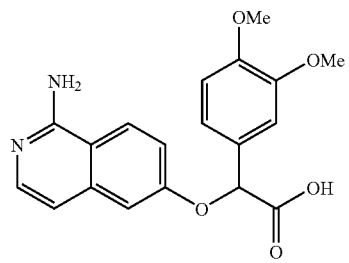

6F (130 mg, 0.29 mmol) was dissolved in THF (8 mL). To this solution was added 10% Pd/C (cat.), and the mixture was hydrogenated at 50 psi for 16 h. The reaction was filtered and concentrated to provide 6G (113 mg, 10%). LC-MS: 355.19 (M+H)$^+$.

6H: Example 6

Example 6 (16 mg, 31%) was prepared from 6G (26 mg, 0.073 mmol) and 5D (30 mg, 0.081 mmol) following a procedure analogous to the preparation of Example 2. $^1$H NMR (400 MHz, CD$_3$OD) δ ppm 1.19 (t, J=7.25 Hz, 3H) 2.11 (s, 3H) 3.19-3.38 (m, 2H) 3.78 (s, 3H) 3.81 (s, 3H) 4.70 (t, J=6.15 Hz, 2H) 5.89 (s, 1H) 6.94 (d, J=7.91 Hz, 1H) 6.98 (d, J=7.03 Hz, 1H) 7.10-7.18 (m, 2H) 7.24 (d, J=2.20 Hz, 1H) 7.36-7.51 (m, 2H) 7.59 (dd, J=8.57, 1.98 Hz, 1H) 7.70-7.83 (m, 2H) 8.30 (d, J=9.23 Hz, 1H) 8.82 (t, J=6.15 Hz, 1H). LC-MS: 593.38 (M+H)$^+$.

Example 7

N-(5-Acetylamino-2-ethanesulfonyl-benzyl)-2-(1-aminoisoquinolin-6-yloxy)-2-(2-fluoro-4,5-dimethoxy-phenyl)-acetamide Trifluoroacetic Acid Salt

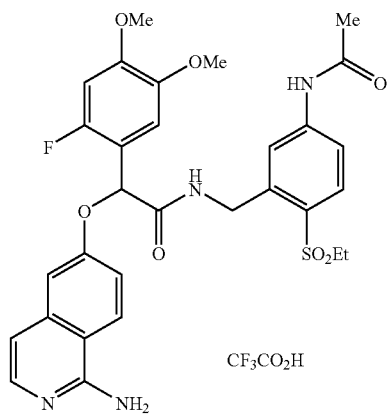

7A: Methyl 2-(2-fluoro-4,5-dimethoxyphenyl)-2-hydroxyacetate

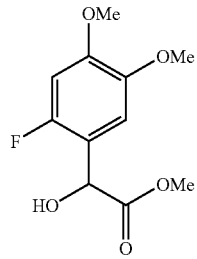

7A (1.05 g, 44%) was prepared in 2 steps from 2-fluoro-4,5-dimethoxybenzaldehyde following procedures analogous to the preparation of 6B. LC-MS: 267.11 (M+Na)$^+$.

7B: Methyl 2-chloro-2-(2-fluoro-4,5-dimethoxyphenyl)acetate

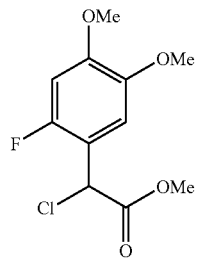

To 7A (280 mg, 1.2 mmol) in CH$_2$Cl$_2$ (5 mL) at 0° C. was added triethylamine (0.42 mL, 3.0 mmol) followed by mesyl chloride (0.12 mL, 1.5 mmol). After stirring at rt overnight, the reaction was filtered, concentrated and purified via silica gel chromatography (0-30% ethyl acetate/hexanes) to provide 7B (268 mg, 89%).

7C: Methyl 2-(1-aminoisoquinolin-6-yloxy)-2-(2-fluoro-4,5-dimethoxyphenyl)-acetate Trifluoroacetic Acid Salt

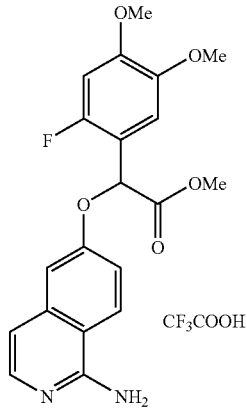

A mixture of 1-aminoisoquinolin-6-ol (1L) (32 mg, 0.20 mmol) in DMF (1 mL) and 60% NaH (10 mg, 0.25 mmol) was stirred for 10 min. To this mixture was added 7B (58 mg, 0.22 mmol) in DMF (0.7 mL). After stirring for 1 h, the reaction was filtered, concentrated and purified via preparative HPLC (MeOH/water/TFA) to provide 7C (80 mg, 80%). LC-MS: 387.21 (M+H)$^+$.

7D: 2-(1-Aminoisoquinolin-6-yloxy)-2-(2-fluoro-4,5-dimethoxyphenyl)acetic Acid Trifluoroacetic Acid Salt

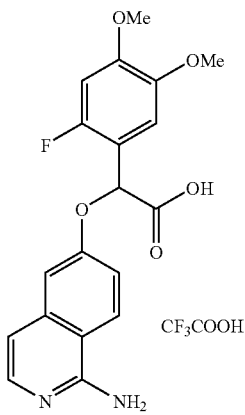

7C (80 mg, 0.21 mmol) was dissolved in THF (2 mL). 1M LiOH (0.4 mL) was added, and the reaction was stirred at rt for 0.5 h. Additional 1M LiOH was added (0.4 mL) and the reaction was stirred for 3 h. The solvent was removed under reduced pressure, and water (10 mL) was added. The solution was acidified with 1 N HCl, then purified via preparative HPLC (MeOH/water/TFA) to provide 7D (65 mg, 64%). LC-MS: 373.18 (M+H)$^+$.

7E: Example 7

A mixture of 7D (29 mg, 0.079 mmol), 5D (44 mg, 0.12 mmol), EDCI (10 mg, 0.050 mmol), HOAT (3.0 mg, 0.022 mmol), DIEA (0.02 mL, 0.11 mmol) in DMF (1 mL) was stirred at 60° C. for 2 h. The reaction was diluted with brine and ethyl acetate, and the layers were separated. The organic layer was concentrated and purified via silica gel chromatography (0-10% MeOH/CH$_2$Cl$_2$). TFA (2 drops) in MeOH (10 mL) was added, and the solution was concentrated to provide Example 7 (31 mg, 54%). $^1$H NMR (400 MHz, CD$_3$OD) δ ppm 1.09 (t, J=7.25 Hz, 3H) 2.00 (s, 3H) 3.17-3.20 (m, 2H) 3.58 (s, 3H) 3.69 (s, 3H) 4.64 (t, J=5.93 Hz, 2H) 6.08 (s, 1H) 6.72 (d, J=11.42 Hz, 1H) 6.85 (d, J=7.03 Hz, 1H) 6.90 (d, J=7.03 Hz, 1H) 7.18 (d, J=2.20 Hz, 1H) 7.30-7.39 (m, 2H) 7.50 (dd, J=8.79, 2.20 Hz, 1H) 7.64-7.77 (m, 2H) 8.20 (d, J=9.23 Hz, 1H) 8.80 (t, J=5.93 Hz, 1H). LC-MS: 611.44 (M+H)$^+$.

Example 8

Methyl 3-((2-(1-aminoisoquinolin-6-yloxy)-2-(3,4-dimethoxyphenyl)-acetamido)methyl)-4-isopropoxyphenylcarbamate Trifluoroacetic Acid Salt

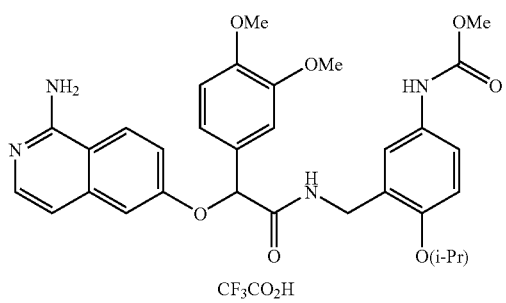

8A: 2-Isopropoxy-5-nitrobenzaldehyde

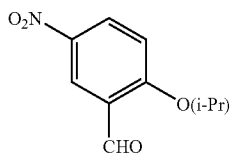

To commercially available 2-hydroxy-5-nitrobenzaldehyde (500 mg, 3.0 mmol) in DMF (10 mL) in a sealable tube was added isopropyl iodide (1.02 g, 6.0 mmol) and potassium carbonate (1.7 g, 12 mmol). The tube was sealed and heated to 95° C. overnight. After cooling to rt, the reaction was diluted with ethyl acetate. The layers were separated, and the organic layer was washed with brine, then concentrated and purified via silica gel chromatography (10-20% ethyl acetate/hexane) to provide 8A (560 mg, 89%). $^1$H NMR (400 MHz, CDCl$_3$) δ ppm 1.48 (d, J=6.15 Hz, 6H) 4.69-4.96 (m, 1H) 7.10 (d, J=9.23 Hz, 1H) 8.40 (dd, J=9.23, 3.08 Hz, 1H) 8.70 (d, J=3.08 Hz, 1H) 10.46 (s, 1H).

8B: (2-Isopropoxy-5-nitrophenyl)methanol

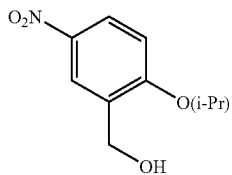

To 8A (210 mg, 1.0 mmol) in hexane (10 mL) was added sodium borohydride (1 mg, 0.30 mmol) and silica gel (0.50 g). The mixture was degassed with Ar for 3 min, then stirred at 40° C. for 3 h under Ar. The reaction was filtered, concentrated and purified via silica gel chromatography (0-20% ethyl acetate/hexane) to provide 8B (195 mg, 92%). LC-MS: 212.19 (M+H)$^+$.

8C: 2-(Azidomethyl)-1-isopropoxy-4-nitrobenzene

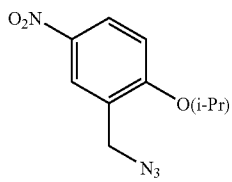

To 8B (190 mg, 0.89 mmol) in THF (5 mL) at 0° C. was added DPPA (300 mg, 1.1 mmol) in THF (1 mL) and DBU (170 mg, 1.9 mmol). The cold bath was removed and the reaction was stirred at rt overnight. The reaction was then concentrated and purified via silica gel chromatography (0-15% ethyl acetate/hexane) to provide 8C (160 mg, 90%) and starting material (8B) (30 mg). 8C: LC-MS: 237.16 (M+H)$^+$.

8D: (2-Isopropoxy-5-nitrophenyl)methanamine Trifluoroacetic Acid Salt

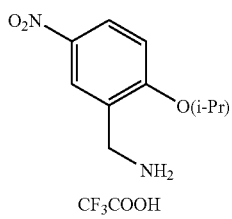

To 8C (160 mg, 0.68 mmol) in THF (5 mL) and water (1 mL) was added triphenylphosphine polymer (20 mg, 1.6 mmol). After stirring at 50° C. for 2 h, the reaction was filtered, concentrated and purified via preparative HPLC (MeOH/water/TFA) to provide 8D (115 mg, 52%). LC-MS: 211.18 (M+H)$^+$.

8E: tert-Butyl 2-isopropoxy-5-nitrobenzylcarbamate

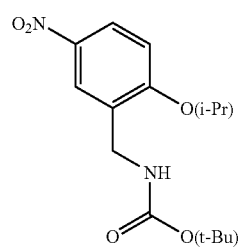

To 8D (95 mg, 0.29 mmol) in water (1 mL) and THF (2 mL) was added sodium bicarbonate (97 mg, 1.2 mmol) followed by di-tert-butyl dicarbonate (77 mg, 0.35 mmol). After stirring at rt for 1 h, the reaction was diluted with ethyl acetate. The layers were separated, and the organic layer was concentrated and purified via silica gel chromatography (0-30% ethyl acetate/hexane) to provide 8E (78 mg, 88%). LC-MS: 333.20 (M+Na)$^+$.

8F: tert-Butyl 5-amino-2-isopropoxybenzylcarbamate

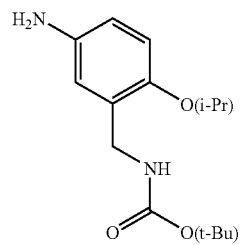

To 8E (72 mg, 0.23 mmol) in MeOH (6 mL) was added Pd/C (cat.) and the mixture was hydrogenated at 55 psi overnight. The reaction was filtered and concentrated to provide 8F (65 mg, 99%). LC-MS: 303.22 (M+Na)$^+$.

8G: [3-(tert-Butoxycarbonylamino-methyl)-4-isopropoxy-phenyl]-carbamic Acid Methyl Ester

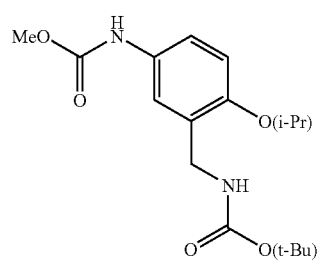

To 8F (24 mg, 0.09 mmol) in pyridine (15 mL) at 0° C. was added methyl chloroformate (18 μL, 0.24 mmol). After removing the ice bath and stirring at rt 7 h, the reaction was concentrated and purified via preparative HPLC (MeOH/water/TFA) to provide 8G (24 mg, 83%). LC-MS: 361.22 (M+Na)⁺.

8H: Methyl 3-(aminomethyl)-4-isopropoxyphenylcarbamate Trifluoroacetic Acid Salt

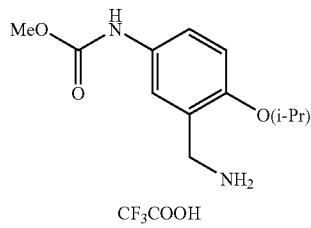

8G (17 mg, 0.05 mmol) was dissolved in CH₂Cl₂ (1 mL) and trifluoroacetic acid (0.2 mL) was added. After stirring at rt for 10 min, the reaction was concentrated to provide 8H (10 mg, 57%). LC-MS: 239.21 (M+H)⁺.

8I: Example 8

Example 8 (6.2 mg, 16%) was prepared from 6G (26 mg, 0.055 mmol) and (8H (10 mg, 0.03 mmol) following a procedure analogous to the preparation of Example 2. ¹H NMR (400 MHz, CD₃OD) δ ppm 1.16 (d, J=6.15 Hz, 3H) 1.20 (d, J=5.71 Hz, 3H) 3.69 (s, 3H) 3.77 (s, 3H) 3.81 (s, 3H) 4.27-4.51 (m, 3H) 5.08 (s, 1H) 6.64 (d, J=2.20 Hz, 1H) 6.75-6.84 (m, 2H) 6.90-6.98 (m, 1H) 7.04-7.12 (m, 2H) 7.11-7.22 (m, J=9.01, 2.42 Hz, 3H) 7.30 (d, J=7.03 Hz, 1H) 8.06 (d, J=9.23 Hz, 1H) 8.38 (t, J=5.49 Hz, 1H). LC-MS: 575.45 (M+H)⁺.

Example 9

N-(3-Acetylamino-benzyl)-2-(4-carbamimidoyl-phenoxy)-2-(3-ethoxy-4-isopropoxy-phenyl)-acetamide Trifluoroacetic Acid Salt

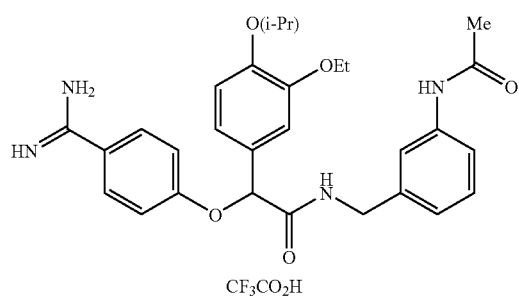

9A: Methyl 2-(4-cyanophenoxy)-2-(3-ethoxy-4-isopropoxyphenyl)acetate

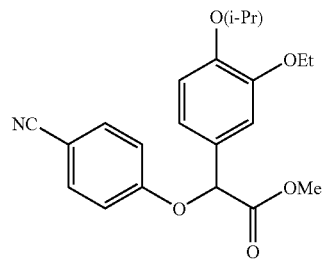

To a mixture of 4-hydroxybenzonitrile (252 mg, 2.12 mmol), methyl 2-(3-ethoxy-4-isopropoxyphenyl)-2-hydroxyacetate(WO 2004072101) (710 mg, 2.65 mmol) and triphenyl phosphine (682 mg, 2.60 mmol) in THF (10 mL) was added DEAD (1.18 mL, 2.60 mmol). The mixture was stirred at rt for 18 h before it was quenched with saturated NaHCO₃ and extracted with ethyl acetate. The organic extract was dried over Na₂SO₄. After removal of solvent, the crude product was purified by flash column chromatography to give 9A (390 mg, 50% yield). ¹H NMR (400 MHz, CDCl₃) δ ppm 1.31 (d, J=6.16 Hz, 6H) 1.40 (t, J=7.03 Hz, 3H) 3.73 (s, 3H) 4.02-4.10 (m, 2H) 4.46-4.55 (m, 1H) 5.61 (s, 1H) 6.90 (d, J=8.35 Hz, 1H) 6.97-7.04 (m, 4H) 7.59 (d, J=9.23 Hz, 2H).

9B: Methyl 2-(4-(N-hydroxycarbamimidoyl)phenoxy)-2-(3-ethoxy-4-isopropoxyphenyl)acetate

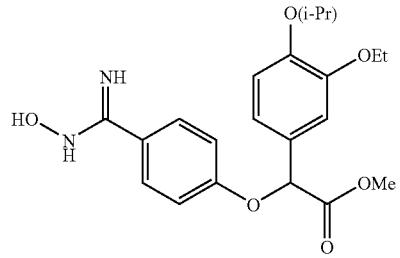

To hydroxyamine HCl salt (363 mg, 5.2 mmol) in DMSO (5.0 mL) was added triethyl amine (0.725 mL, 5.2 mmol). After stirring at rt for 10 min, the cloudy solution was filtered directly into a round-bottom flask containing 9A (482 mg, 1.3 mmol). The mixture was stirred at 60° C. for 18 h before it was diluted with ethyl acetate and washed with 5% NaHCO₃/brine. The organic extract was dried over Na₂SO₄ and concentrated to give 9B as a white solid. LC-MS 403 (M+H)⁺.

9C: Methyl 2-(4-carbamimidoylphenoxy)-2-(3-ethoxy-4-isopropoxyphenyl)acetate Acetic Acid Salt

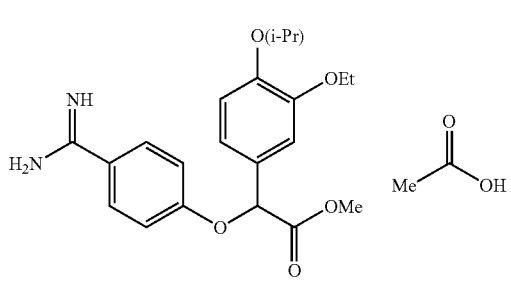

To 9B (575 mg, 1.43 mmol) in acetic acid (14 mL) was added acetic anhydride (0.155 mL, 1.64 mmol) and 10% Pd/C (90 mg). The mixture was hydrogenated with a hydrogen balloon at rt for 3.0 h. After removal of solvent, 9C (580 mg, 100% yield) was obtained as a white solid. $^1$H NMR (400 MHz, CDCl$_3$) δ ppm 1.24 (d, J=6.16 Hz, 6H) 1.30 (t, J=7.03 Hz, 3H) 1.69 (s, 3H) 3.66 (s, 3H) 4.00 (q, J=7.03 Hz, 2H) 4.46-4.50 (m, 1H) 6.09 (s, 1H) 6.90 (d, J=8.35 Hz, 1H) 6.97-7.14 (m, 4H) 7.72 (d, J=9.23 Hz, 2H). LC-MS 387 (M+H)$^+$.

9D: Methyl 2-(4-(N-(benzyloxycarbonyl)carbamimidoyl)phenoxy)-2-(3-ethoxy-4-isopropoxyphenyl)acetate

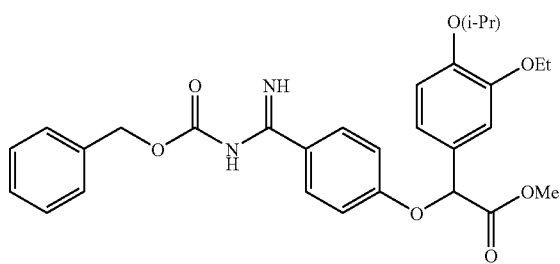

To a suspension of 9C (570 mg, 1.12 mmol) in CH$_2$Cl$_2$ (12 mL) was added 1.0 M NaHCO$_3$ (11.2 mL, 11.2 mmol), followed by benzyl chloroformate (0.22 mL, 1.5 mmol) in CH$_2$Cl$_2$ (3.0 mL). The mixture was stirred at rt for 30 min. TLC indicated some 9C still present. Another portion of benzyl chloroformate (0.1 mL, 0.84 mmol) in CH$_2$Cl$_2$ (3.0 mL) was added. After stirring at rt for 1.0 h, the reaction was quenched with ammonium hydroxide (0.65 mL), and extracted with CH$_2$Cl$_2$. The organic extract was washed with brine and dried over Na$_2$SO$_4$. After removal of the solvent, the crude product was purified by flash column chromatography eluting with ethyl acetate/hexanes (1:1) to give 9D (570 mg, 73% yield) as a white solid. $^1$H NMR (400 MHz, CDCl$_3$) δ ppm 1.32 (d, J=6.16 Hz, 6H) 1.38 (t, J=7.03 Hz, 3H) 3.71 (s, 3H) 4.04 (q, J=7.03 Hz, 2H) 4.46 (m, 1H) 5.18 (s, 2H) 5.58 (s, 1H) 6.85 (d, J=8.8 Hz, 1H) 6.90 (d, J=8.35 Hz, 2H) 7.09 (m, 2H) 7.20-7.40 (m, 6H), 7.82 (d, J=9.20 Hz, 2H).

9E: 2-(4-(N-(Benzyloxycarbonyl)carbamimidoyl)phenoxy)-2-(3-ethoxy-4-isopropoxyphenyl)acetic Acid

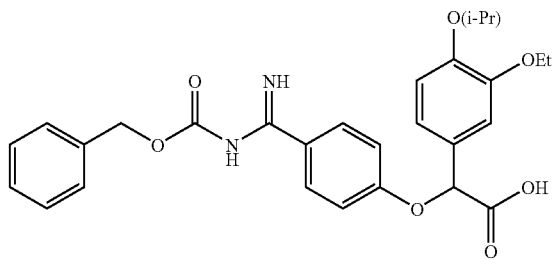

To 9D (570 mg, 1.09 mmol) in THF (6.0 mL) and MeOH (0.5 mL) was added LiOH (1.0 M, 1.92 mL, 1.92 mmol). The mixture was stirred at rt for 1.0 h before it was acidified with 1.0 N HCl (5.0 mL). The mixture was extracted with ethyl acetate, washed with brine and dried over Na$_2$SO$_4$. After removal of solvent, 9E (500 mg, 90% yield) was obtained as a white solid. $^1$H NMR (400 MHz, DMSO-d$_6$) δ ppm 1.23 (d, J=6.16 Hz, 6H) 1.30 (t, J=7.03 Hz, 3H) 4.00 (q, J=7.03 Hz, 2H) 4.49 (m, 1H) 5.09 (s, 2H) 5.85 (s, 1H) 6.90-7.38 (m, 11H) 7.95 (d, J=9.20 Hz, 2H).

9F: Example 9

A mixture of 9E (50 mg, 0.098 mmol), commercially available N-(3-(aminomethyl)phenyl)-acetamide hydrochloride (34 mg, 0.17 mmol), EDCI (37.5 mg, 0.20 mmol), HOAT (13 mg, 0.098 mmol), N-methylmorpholine (0.032 mL, 0.29 mmol) in CH$_2$Cl$_2$ (5 mL) and DMF (2 mL) was stirred at rt overnight. The reaction was diluted with CH$_2$Cl$_2$ then washed with brine and water. The organic layer was dried (Na$_2$SO$_4$), filtered and concentrated. The resulting residue was dissolved in MeOH (5 mL), Pd/C (50 mg) was added, and the mixture was hydrogenated under a hydrogen balloon for 1 h. Additional Pd/C (25 mg) was added, and hydrogenation was continued for an additional hour. The reaction was filtered and purified via preparative HPLC (acetonitrile/H$_2$O/TFA) to provide Example 9 (22 mg, 35%). $^1$H NMR (400 MHz, CD$_3$OD) δ ppm 1.29 (d, J=6.15 Hz, 6H) 1.36 (t, J=7.03 Hz, 3H) 3.89-4.09 (m, 2H) 4.34-4.47 (m, 2H) 4.45-4.61 (m, 1H) 5.73 (s, 1H) 6.94 (d, J=8.35 Hz, 1H) 7.02-7.35 (m, 9H) 7.75 (d, J=9.23 Hz, 2H). LC-MS: 462.4 (M+H)$^+$.

Example 10

N-Benzyl-2-(4-carbamimidoylphenoxy)-2-(3-ethoxy-4-isopropoxyphenyl)acetamide Trifluoroacetic Acid Salt

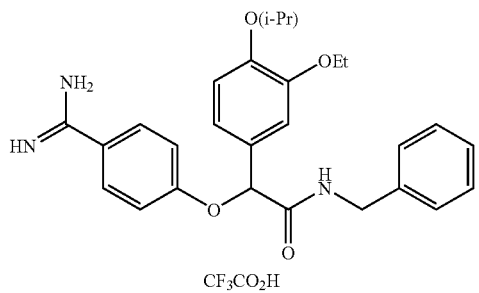

A mixture of 9E (39 mg, 0.075 mmol), benzylamine (17 mg, 0.15 mmol), EDCI (60 mg, 0.31 mmol), HOAT (4.4 mg, 0.032 mmol), DIEA (0.09 mL, 0.52 mmol) in CH$_2$Cl$_2$ (3 mL) was stirred at rt overnight. The reaction was concentrated and purified via preparative HPLC (MeOH/H$_2$O/TFA) to provide benzyl (4-(2-(benzylamino)-1-(3-ethoxy-4-isopropoxyphenyl)-2-oxyethoxy)phenyl)(imino)-methylcarbamate trifluoroacetic acid salt. This product was dissolved in MeOH (3 mL), Pd/C (cat.) was added, and the mixture was hydrogenated under a hydrogen balloon for 1 h. The reaction was filtered and purified via preparative HPLC (MeOH/H$_2$O/TFA) to provide Example 10 (19 mg, 44%). $^1$H NMR (400 MHz, CD$_3$OD) δ ppm 1.29 (d, J=6.15 Hz, 6H) 1.36 (t, J=7.03 Hz, 3H) 3.89-4.09 (m, 2H) 4.34-4.47 (m, 2H) 4.45-4.61 (m, 1H) 5.73 (s, 1H) 6.94 (d, J=8.35 Hz, 1H) 7.02-7.35 (m, 9H) 7.75 (d, J=9.23 Hz, 2H). LC-MS: 462.4 (M+H)⁺.

Example 11

N-(2-(Cyclopropylsulfanyl)benzyl)-2-(4-carbamimidoylphenoxy)-2-(3-ethoxy-4-isopropoxyphenyl)acetamide Trifluoroacetic Acid Salt

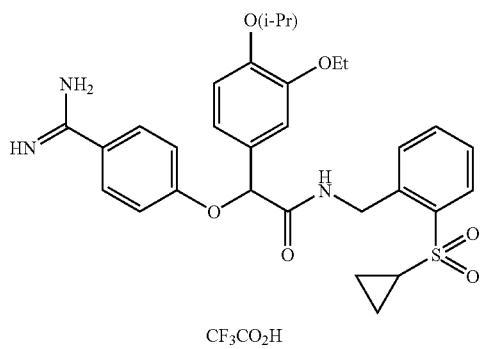

Example 11 (5.7 mg, 11%) was prepared in two steps from 9E (40 mg, 0.079 mmol) and 1B (23 mg, 0.091 mmol) following procedures analogous to the preparation of Example 10. ¹H NMR (400 MHz, CD₃OD) δ ppm 0.99-1.10 (m, 2H) 1.15-1.23 (m, 2H) 1.28 (d, J=6.15 Hz, 6H) 1.35 (t, J=7.03 Hz, 3H) 2.81-2.95 (m, 1H) 3.89-4.03 (m, 2H) 4.43-4.57 (m, 1H) 4.84-4.88 (m, 2H) 5.78 (s, 1H) 6.93 (d, J=8.35 Hz, 1H) 7.02-7.11 (m, 2H) 7.20 (d, J=9.23 Hz, 2H) 7.37 (d, J=7.47 Hz, 1H) 7.41-7.55 (m, 2H) 7.69-7.80 (m, 2H) 7.81-7.92 (m, 1H) 8.85 (t, J=6.15 Hz, 1H). LC-MS: 566.46 (M+H)⁺.

Example 12

N-(5-Acetylamino-2-ethanesulfonyl-benzyl)-2-(4-carbamimidoyl-phenoxy)-2-(3-ethoxy-4-isopropoxy-phenyl)-acetamide Trifluoroacetic Acid Salt

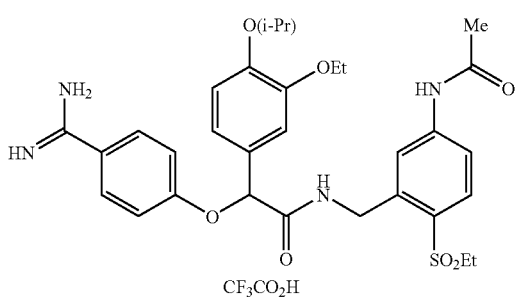

Example 12 (28 mg, 39%) was prepared in two steps from 9E (51 mg, 0.10 mmol) and 5D following procedures analogous to the preparation of Example 10. ¹H NMR (400 MHz, CD₃OD)₆ ppm 1.11 (t, J=7.25 Hz, 3H) 1.18 (d, J=6.15 Hz, 6H) 1.25 (t, J=7.03 Hz, 3H) 2.05 (s, 3H) 3.17-3.22 (m, 2H) 3.73-3.94 (m, 2H) 4.33-4.48 (m, 1H) 4.52-4.72 (m, 2H) 5.66 (s, 1H) 6.81 (d, J=7.91 Hz, 1H) 6.90-6.99 (m, 2H) 7.06-7.16 (m, 2H) 7.54 (dd, J=8.35, 2.20 Hz, 1H) 7.59-7.68 (m, 2H) 7.68-7.82 (m, 2H). LC-MS: 611.11 (M+H)⁺.

Example 13

N-(3-Acetylamino-benzyl)-2-(4-aminomethyl-phenoxy)-2-(3-ethoxy-4-isopropoxy-phenyl)-acetamide Trifluoroacetic Acid Salt

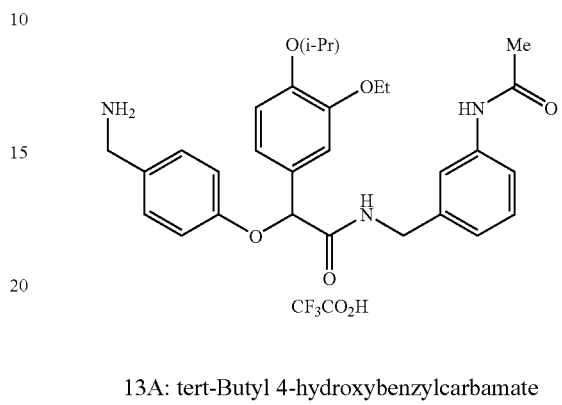

13A: tert-Butyl 4-hydroxybenzylcarbamate

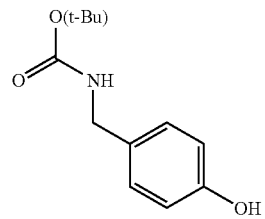

To 4-(aminomethyl)phenol (123 mg, 1.0 mmol) in THF (2 mL) was added sodium bicarbonate (250 mg, 3.0 mmol) in water (2 mL) followed by di-tert-butyl-dicarbonate (240 mg, 1.1 mmol). After stirring at rt for 2 h, the reaction was diluted with ethyl acetate, washed with brine, dried (Na₂SO₄), filtered and concentrated. The resulting residue was purified via silica gel chromatography eluting with 0-40% ethyl acetate/hexane to provide 13A (223 mg, 100%). LC-MS: 246.17 (M+Na)⁺.

13B: Benzyl 2-(4-((tert-butoxycarbonyl)methyl)phenoxy)-2-(3-ethoxy-4-isopropoxyphenyl)acetate

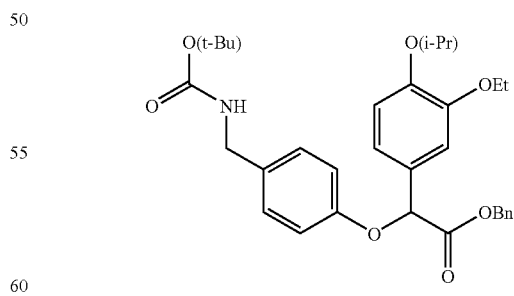

To a solution of 13A (112 mg, 0.5 mmol) in THF (3 mL) was added 60% sodium hydride (24 mg, 0.6 mmol). After stirring at rt for 20 min, chloro-(3-ethoxy-4-isopropoxy-phenyl)-acetic acid benzyl ester (WO 2004072101) (181 mg, 0.5 mmol) was added and the mixture was stirred at rt overnight. The reaction was diluted with ethyl acetate and washed with brine. The layers were separated, and the organic layer was concentrated and purified via preparative HPLC to provide 13B (85 mg, 31%). LC-MS: 572.42 (M+Na)+.

13C: 2-(4-((tert-Butoxycarbonyl)methyl)phenoxy)-2-(3-ethoxy-4-isopropoxyphenyl)acetic Acid

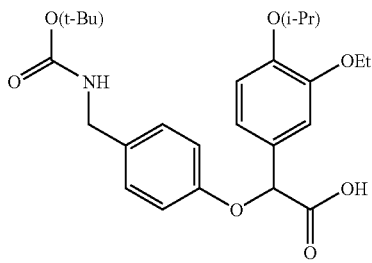

A mixture of 13B (85 mg, 0.15 mmol) and Pd/C (cat.) was hydrogenated at 40 psi overnight. The reaction was filtered and concentrated to provide 13C (39 mg, 99%). LC-MS: 482.37 (M+Na)+.

13D: Example 13

A mixture of 13C (34 mg, 0.074 mmol), commercially available N-(3-(aminomethyl)phenyl)acetamide (30 mg, 0.15 mmol), EDCI (30 mg, 0.15 mmol), HOAT (10 mg, 0.07 mmol), DIEA (0.08 mL, 0.45 mmol) in DMF (2 mL) was stirred at 60° C. for 2 h. The reaction was diluted with water and ethyl acetate. The layers were separated and the organic layer was washed with brine then dried (Na2SO4), filtered and concentrated. The resulting residue was purified via preparative HPLC (MeOH/H2O/TFA) to provide tert-butyl 4-(2-(3-acetamidobenzylamino)-1-(3-ethoxy-4-isopropoxyphenyl)-2-oxyethoxy)benzylcarbamate trifluoroacetic acid salt (32 mg, 71%). This product was dissolved in CH2Cl2 (0.9 mL), and TFA (0.3 mL) was added. After stirring at rt for 20 min, the reaction was concentrated and purified via preparative HPLC (MeOH/H2O/TFA) to provide Example 13 (22 mg, 69%). $^1$H NMR (400 MHz, CD3OD) δ ppm 1.28 (d, J=6.15 Hz, 6H) 1.35 (t, J=6.81 Hz, 3H) 2.10 (s, 3H) 3.96 (q, J=7.03 Hz, 2H) 4.01 (s, 2H) 4.28-4.45 (m, 2H) 4.45-4.57 (m, 1H) 5.60 (s, 1H) 6.84-6.95 (m, 2H) 6.99-7.12 (m, 4H) 7.17 (t, J=7.91 Hz, 1H) 7.34 (t, J=7.91 Hz, 3H) 7.46 (s, 1H) 8.94 (t, J=5.93 Hz, 1H). LC-MS: 506.41 (M+H)+.

Example 14

N-(5-Acetylamino-2-ethanesulfonyl-benzyl)-2-(4-aminomethyl-phenoxy)-2-(3-ethoxy-4-isopropoxy-phenyl)-acetamide Trifluoroacetic Acid Salt

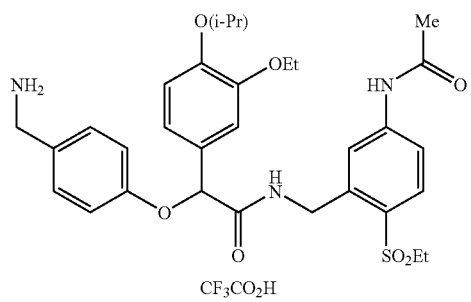

A mixture of 13C (22 mg, 0.048 mmol), 5D (37 mg, 0.15 mmol), EDCI (20 mg, 0.10 mmol), HOAT (6 mg, 0.05 mmol), DIEA (0.05 mL, 0.29 mmol) in DMF (2 mL) was stirred at 60° C. for 3 h. The reaction was diluted with water and ethyl acetate. The layers were separated and the organic layer was washed with brine then dried (Na2SO4), filtered and concentrated. The resulting residue was purified via preparative HPLC (MeOH/H2O/TFA) to provide tert-butyl 4-(2-(5-acetamido-2-(ethylsulfonyl)-benzylamino)-1-(3-ethoxy-4-isopropoxyphenyl)-2-oxyethoxy)benzylcarbamate trifluoroacetic acid salt. This product was dissolved in ethyl acetate (1.5 mL), and 4N HCl in dioxane (1 mL) was added. After stirring at rt for 2 h, the reaction was concentrated and purified via preparative HPLC (MeOH/H2O/TFA) to provide Example 14 (9.5 mg, 28%, 2 steps). $^1$H NMR (400 MHz, CD3OD) δ ppm 1.20 (t, J=7.25 Hz, 3H) 1.26 (d, J=6.15 Hz, 6H) 1.33 (t, J=7.03 Hz, 3H) 2.13 (s, 3H) 3.26-3.33 (m, 2H) 3.89-3.96 (m, 2H) 4.00 (s, 2H) 4.43-4.51 (m, 1H) 4.58-4.80 (m, 2H) 5.63 (s, 1H) 6.88 (d, J=8.35 Hz, 1H) 6.98-7.03 (m, 2H) 7.06 (d, J=8.79 Hz, 2H) 7.32 (d, J=8.35 Hz, 2H) 7.67 (dd, J=8.57, 1.98 Hz, 1H) 7.78 (d, J=1.76 Hz, 1H) 7.84 (d, J=8.79 Hz, 1H) 8.82 (t, J=6.37 Hz, 1H). LC-MS: 598.46 (M+H)+.

Example 15

Methyl 3-((2-(1-aminoisoquinolin-6-yloxy)-2-(3,4-dimethoxyphenyl)acetamido)methyl)-4-(isopropylsulfonyl)phenylcarbamate Trifluoroacetic Acid Salt

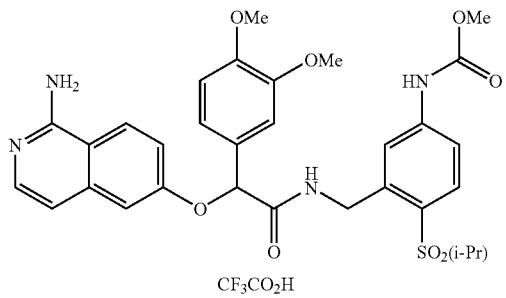

15A: 2-(Isopropylthio)-5-nitrobenzonitrile

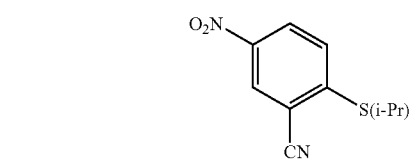

To a solution of 2-fluoro-5-nitrobenzonitrile (2.5 g, 15.6 mmol) in DMF (50 mL) were added 2-propane thiol (1.74 mL, 18.6 mmol) and triethylamine (4.8 mL, 34.4 mmol). After stirring at ambient temperature for 1 h, the reaction mixture was poured into water (250 mL) and extracted with methylene chloride (3×50 mL). The organic layer was washed with water (2×) and brine, then dried over MgSO4 and concentrated to yield 2.98 g (86%) of 15A as a yellow oil which solidified upon standing.

15B: 2-(Isopropylsulfonyl)-5-nitrobenzonitrile

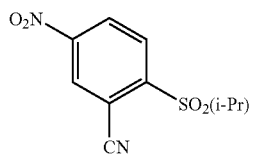

MCPBA (7.40 g, 33.0 mmol) was added portionwise to a solution of 15A (2.98 g, 13.4 mmol) in CH$_2$Cl$_2$ (50 mL) at 0° C. The reaction mixture was allowed to warm to ambient temperature and was stirred over the weekend. The mixture was diluted with CH$_2$Cl$_2$, and then extracted twice with CH$_2$Cl$_2$. The organic layers were combined, washed with 10% NaHSO$_3$ (3×), saturated aqueous NaHCO$_3$ (2×), and brine, then dried over MgSO$_4$ and concentrated to give 3.04 g (91%) of 15B as a white solid. $^1$H NMR (400 MHz, CDCl$_3$) δ ppm 1.40 (d, J=7.03 Hz, 6H) 3.60-3.72 (m, 1H) 8.38 (d, J=8.35 Hz, 1H) 8.63 (dd, J=8.79, 2.20 Hz, 1H) 8.74 (d, J=2.64 Hz, 1H).

15C: 5-Amino-2-(isopropylsulfonyl)benzonitrile

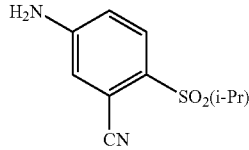

To 2-(isopropylsulfonyl)-5-nitrobenzonitrile (15B) (1.26 g, 4.96 mmol) in THF (20 mL) was added Pd/C (cat.) and the mixture was hydrogenated at 50 psi overnight. The reaction was filtered to provide 15C (1.09 g). LC-MS: 225.3 (M+H)$^+$.

15D: Methyl 3-cyano-4-(isopropylsulfonyl)phenylcarbamate

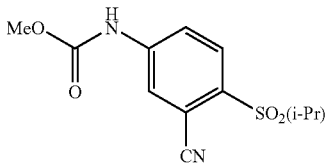

To 15C (450 mg, 2 mmol) in pyridine (10 mL) at 0° C. was added methyl chloroformate (0.8 mL, 10 mmol). The reaction was stirred at 0° C. for 20 min, then warmed to rt for 2 h. The reaction was concentrated, then diluted with ethyl acetate, washed with brine, dried (Na$_2$SO$_4$), filtered and concentrated. The resulting residue was purified via silica gel chromatography (0-60% ethyl acetate/hexanes) to provide 15D (490 mg, 88%). LC-MS: 283.35 (M+H)$^+$.

15E: Methyl 3-(aminomethyl)-4-(isopropylsulfonyl) phenylcarbamate Hydrochloride

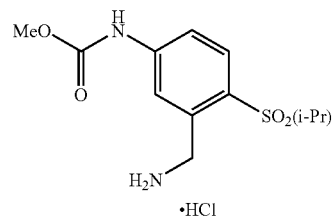

To 15D (230 mg, 0.82 mmol) in THF (15 mL) was added Raney Ni (cat.) and the mixture was hydrogenated at 60 psi for 6 h. The reaction was filtered and concentrated to provide methyl 3-(aminomethyl)-4-(isopropylsulfonyl)phenylcarbamate (227 mg), which was suspended in ether. A solution of 4N HCl in dioxane (0.5 mL) was added and the reaction was concentrated to provide 15E (265 mg, 100%). LC-MS: 287.38 (M+H)$^+$.

15F: Example 15

A mixture of 6G (35 mg, 0.10 mmol), 15E (40 mg, 0.12 mmol), and BOP (66 mg, 0.15 mmol) in DMF (2 mL) was stirred at rt for 5 min. Et$_3$N (70 mg, 0.69 mmol) was added and the reaction was stirred 20 min. Brine was added and the product was extracted with ethyl acetate (3×20 mL). The organic layers were separated, combined and washed dried (Na$_2$SO$_4$), filtered and concentrated. The resulting residue was purified via preparative HPLC (MeOH/H$_2$O/TFA) to provide Example 15 (52 mg, 71%). $^1$H NMR (400 MHz, CD$_3$OD) δ ppm 1.19 (d, J=6.59 Hz, 3H) 1.22 (d, J=7.03 Hz, 3H) 3.40-3.49 (m, 1H) 3.71 (s, 3H) 3.74-3.82 (m, 6H) 4.55-4.79 (m, 2H) 5.88 (s, 1H) 6.85-6.96 (m, 2H) 7.09-7.16 (m, 2H) 7.19 (d, J=2.20 Hz, 1H) 7.34-7.48 (m, 3H) 7.61 (s, 1H) 7.69 (d, J=8.35 Hz, 1H) 8.26 (d, J=9.23 Hz, 1H). LC-MS: 623.2 (M+H)$^+$.

Example 16

3-(3-((2-(1-Aminoisoquinolin-6-yloxy)-2-(3,4-dimethoxyphenyl)acetamido)methyl)-4-(isopropyl-sulfonyl)phenyl)-1,1-dimethylurea Trifluoroacetic Acid Salt

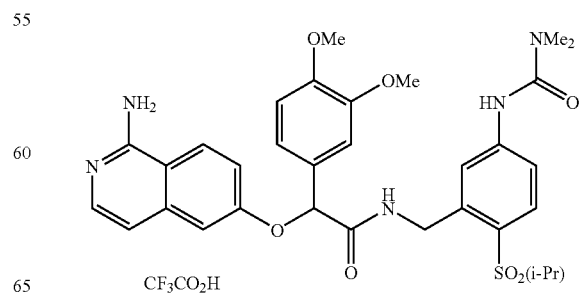

16A: 3-(3-Cyano-4-(isopropylsulfonyl)phenyl)-1,1-dimethylurea

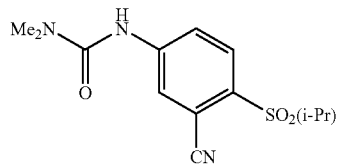

To 15C (67 mg, 0.30 mmol) in methylene chloride (2 mL) at 0° C. was added NaHCO$_3$ (252 mg, 3 mmol) followed by a ca. 20% phosgene solution in toluene (0.3 mL). After stirring at that temperature for 2 h, the reaction was concentrated and diluted with methylene chloride (3 mL). To this solution was added Et$_3$N (130 mg, 1.28 mmol) followed by dimethylamine hydrochloride (43 mg, 0.53 mmol) and the reaction was stirred overnight. The solution was loaded onto a silica gel column and purified via silica gel chromatography (0-80% ethyl acetate/hexane) to provide 16A (44 mg, 50%) and recovered starting material (15C) (20 mg). 16A: LC-MS: 296.02 (M+H)$^+$.

16B: 3-(3-(Aminomethyl)-4-(isopropylsulfonyl)phenyl)-1,1-dimethylurea

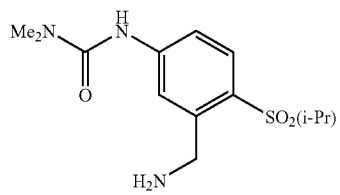

To 16A (45 mg, 0.15 mmol) in THF (10 mL) was added Raney Ni (cat.) and the mixture was hydrogenated at 60 psi for 4 h. The reaction was filtered and concentrated to provide 16B (41 mg, 91%). LC-MS: 300.37 (M+H)$^+$

16C: Example 16

Example 16 (23 mg, 93%) was prepared from 6G and 16B following a procedure analogous to that used in the preparation of 15F. $^1$H NMR (400 MHz, CD$_3$OD) δ ppm 1.19 (d, J=6.59 Hz, 3H) 1.22 (d, J=7.03 Hz, 3H) 2.99 (s, 6H) 3.36-3.46 (m, 1H) 3.78 (s, 3H) 3.79 (s, 3H) 4.62-4.72 (m, J=4.61, 4.61 Hz, 2H) 5.88 (s, 1H) 6.92 (d, J=8.79 Hz, 1H) 6.97 (d, J=7.03 Hz, 1H) 7.09-7.17 (m, 2H) 7.23 (d, J=2.64 Hz, 1H) 7.39-7.46 (m, 2H) 7.49 (dd, J=8.79, 2.20 Hz, 1H) 7.57 (d, J=2.20 Hz, 1H) 7.68 (d, J=8.79 Hz, 1H) 8.28 (d, J=9.23 Hz, 1H). LC-MS: 636.2 (M+H)$^+$.

Utility

The compounds of the present invention are inhibitors of factor VIIa and are useful as anticoagulants for the prevention or treatment of thromboembolic disorders in mammals. In general, a thromboembolic disorder is a circulatory disease caused by blood clots (i.e., diseases involving fibrin formation, platelet activation, and/or platelet aggregation). The term "thromboembolic disorders (or conditions)" as used herein includes arterial or venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary and cerebral arterial thrombosis, cerebral embolism, kidney embolisms, pulmonary embolisms, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, and vessel grafts. The procedures include, but not limited to: cardiopulmonary bypass, percutaneous coronary intervention, and hemodialysis.

It is noted that thrombosis includes vessel occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant or antithrombotic effect of compounds of the present invention is believed to be due to inhibition of serine proteases involved in the coagulation cascade, more specifically, inhibition of the coagulation factor VIIa.

The term "thrombosis", as used herein, refers to formation or presence of a thrombus (pl. thrombi); clotting within a blood vessel which may cause ischemia or infarction of tissues supplied by the vessel. The term "embolism", as used herein, refers to sudden blocking of an artery by a clot or foreign material which has been brought to its site of lodgment by the blood current. The term "thromboembolism", as used herein, refers to obstruction of a blood vessel with thrombotic material carried by the blood stream from the site of origin to plug another vessel. The term "stroke", as used herein, refers to embolic stroke or atherothrombotic stroke arising from occlusive thrombosis in the carotid communis, carotid interna, or intracerebral arteries.

The effectiveness of compounds of the present invention as inhibitors of the coagulation factors VIIa, IXa, Xa, XIa, plasma kallikrein or thrombin, can be determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted in the release of para-nitroaniline (pNA), which was monitored spectrophotometrically by measuring the increase in absorbance at 405 nM, or the release of aminomethylcoumarin (AMC), which was monitored spectrofluorometrically by measuring the increase in emission at 460 nM with excitation at 380 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-Ile-Pro-Arg-pNA (S-2288; Chromogenix or BMPM-2; AnaSpec) at a concentration of 0.001 M. In general, preferred compounds of the present invention, such as the particular compounds disclosed in the above examples, have been identified to be active and exhibit $K_i$'s of equal to or less than 15 μM in the Factor VIIa assay, thereby demonstrating the utility of the compounds of the present invention as especially effective inhibitors of coagulation Factor VIIa, and thus, as inhibitors of the coagulation cascade and as anticoagulants for the prevention or treatment of thromboembolic disorders in mammals. More preferred compounds have $K_i$'s of equal to or less than 5 μM, preferably equal to or less than 1 μM, more preferably equal to or less than 0.5 μM, even more preferably equal to or less than 0.1 μM.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Phe-Gly-Arg-AMC; CenterChem) at a concentration of 0.0004-0.0005 M. In general, compounds tested in the Factor IXa assay are considered to be active if they exhibit a $K_i$ of equal to or less than 15 μM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 μM and the synthetic substrate S-2222 (Bz-Ile-Glu(gamma-OMe, 50%)-Gly-Arg-pNA; Chromogenix) at a concentration of 0.0002-0.0003 M. In general, compounds tested in the Factor Xa assay are considered to be active if they exhibit a $K_i$ of equal to or less than 15 μM.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 μM (Haematologic Technologies) and the synthetic substrate S-2366 (pyroGlu-Pro-Arg-pNA; Chromogenix) at a concentration of 0.0002-0.00025 M. In general, compounds tested in the Factor XIa assay are considered to be active if they exhibit a $K_i$ of equal to or less than 15 μM.

Plasma kallikrein determinations were made in 0.1 M sodium phosphate buffer at a pH of 7.4 containing 0.2 M sodium chloride and 0.5% PEG 8000. Determinations were made using purified human kallikrein (Enzyme Research Laboratories) at a final assay concentration of 200 μM and the synthetic substrate S-2302 (H-(D)-Pro-Phe-Arg-pNA; Chromogenix) at a concentration of 0.00008-0.0004 M. The Km value used for calculation of $K_i$ was 0.00005 to 0.00007 M. In general, compounds tested in the plasma kallikrein assay are considered to be active if they exhibit a $K_i$ of equal to or less than 15 μM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002 M. In general, compounds tested in the thrombin assay are considered to be active if they exhibit a $K_i$ of equal to or less than 15 μM.

The selectivity of a compound may be evaluated by taking the ratio of the $K_i$ value for a given protease with the $K_i$ value for the protease of interest (i.e., selectivity for FVIIa versus protease P=$K_i$ for protease P/$K_i$ for FVIIa). Compounds with selectivity ratios >20 are considered selective. Compounds with selectivity ratios >100 are preferred, and compounds with selectivity ratios >500 are more preferred.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance change vs time) were measured. The following relationship was used to calculate $K_i$ values:

$$(v_o-v_s)/v_s = I/(K_i(1+S/K_m)) \text{ for a competitive inhibitor with one binding site; or}$$

$$v_s/v_o = A+((B-A)/1+((IC_{50}/(I)^n))) \text{ and}$$

$$K_i = IC_{50}/(1+S/K_m) \text{ for a competitive inhibitor}$$

where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme: inhibitor complex;
S is the concentration of substrate; and
$K_m$ is the Michaelis constant for the substrate.

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

In Vivo Electrically-Induced Carotid Artery Thrombosis (ECAT) Model:

The rabbit ECAT model, described by Wong et al. (*J Pharmacol Exp Ther* 2000, 295, 212-218), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to the initiation of thrombosis. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

In Vivo Rabbit Arterio-Venous (AV) Shunt Thrombosis Model:

The rabbit AV shunt model, described by Wong et al. (Wong, P. C. et al. *J Pharmacol Exp Ther* 2000, 292, 351-357), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by a nonlinear least square regression program using the Hill sigmoid $E_{max}$ equation (DeltaGraph; SPSS Inc., Chicago, Ill.).

The compounds of the present invention can be administered alone or in combination with one or more additional therapeutic agents. These other agents include, but are not limited to, other anti-coagulant or coagulation inhibitory agents, anti-platelet or platelet inhibitory agents, or thrombolytic or fibrinolytic agents.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Other anticoagulant agents (or coagulation inhibitory agents) that may be used in combination with the compounds of this invention include warfarin, heparin (either unfractionated heparin or any commercially available low molecular weight heparin, for example LOVANOX™), synthetic pentasaccharide, direct acting thrombin inhibitors including hirudin and argatroban, as well as other factor VIIa inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granular-content secretion of platelets. Such agents include, but are not limited to, the various known non-steroidal anti-inflammatory drugs (NSAIDS) such as acetaminophen, aspirin, codeine, diclofenac, droxicam, fentanyl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicylic acid or ASA), and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR1) antagonists (e.g., SCH-530348, SCH-203099, SCH-529153 and SCH-205831), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, prasugrel, and AZD-6140, and pharmaceutically acceptable salts or prodrugs thereof. Clopidogrel is an even more preferred agent. Ticlopidine and clopidogrel are also preferred compounds since they are known to be more gentle than aspirin on the gastrointestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, antistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term antistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrhythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K⁺ channel openers such as $I_{Ach}$ inhibitors, and $I_{Kur}$ inhibitors (e.g., compounds such as those disclosed in WO01/40231).

Examples of suitable antihypertensive agents for use in combination with the compounds of the present invention include alpha adrenergic blockers; beta adrenergic blockers; calcium channel blockers (e.g., diltiazem, verapamil, nifedipine, amlodipine and mybefradil); diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone); renin inhibitors; angiotensin-converting enzyme (ACE) inhibitors (e.g., captopril, lisinopril, fosinopril, enalapril, ceranopril, cilazapril, delapril, pentopril, quinapril, ramipril, lisinopril), angiotensin AT-1 receptor antagonists (e.g., irbestatin, losartan, valsartan); ET-A receptor antagonists (e.g., sitaxsentan, atrsentan and compounds disclosed in U.S. Pat. Nos. 5,612,359 and 6,043,265); Dual ET-A/AT-1 antagonist (e.g., compounds disclosed in WO 00/01389); neutral endopeptidase (NEP) inhibitors; vasopeptidase inhibitors (dual ACE/NEP inhibitors, e.g., omapatrilat gemopatrilat, nitrates) and β-blockers (for example propranolol, nadolol, or carvedilol).

Examples of suitable cardiac glycosides for use in combination with the compounds of the present invention include digitalis and ouabain.

Examples of suitable mineralocorticoid receptor antagonists for use in combination with the compounds of the present invention include spironolactone and eplirinone.

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DPP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; piroxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., conjugated estrogens) and estradiol.

Examples of suitable anti-obesity agents for use in combination with the compounds of the present invention include orlistat, aP2 inhibitors (such as those disclosed in WO00/59506), and cannabinoid receptor CB1 antagonists (e.g., rimonabant, AVE-1625, SR-147778, and CP-945598).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epothilones, cisplatin, and carboplatin.

Cholesterol/lipid lowering agents for use in combination with the compounds of the present invention include HMG-CoA reductase inhibitors (lovastatin, simvastatin, pravastatin, fluvastatin, atorvastatin, rosuvastatin, and other statins), sequestrants (cholestyramine and colestipol), nicotinic acid, fenofibric acid derivatives (gemfibrozil, clofibrat, fenofibrate and benzafibrate), and probucol.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of plasma kallikrein, thrombin, factor VIIa, IXa, Xa and/or XIa. Such compounds may be provided in a commercial kit, for example, for use in pharmaceutical research involving plasma kallikrein, thrombin, factor VIIa, IXa, Xa and/or XIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving plasma kallikrein, thrombin, factor VIIa, IXa, Xa, and/or XIa. For example, the presence of plasma kallikrein, thrombin, factor VIIa, IXa, Xa and/or XIa in an unknown sample could be determined by addition of the relevant chromogenic substrate, for example, S2288 for factor VIIa, to a series of solutions containing test sample and optionally one of the compounds of the present invention. If production of pNA is observed in the solutions containing test sample, but not in the presence of a compound of the present invention, then one would conclude factor VIIa was present.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.001 to 100 mg/kg of body weight per day, and most preferably between about 0.001 to 20 mg/kg/day. Intravenously, the most preferred doses will range from about 0.1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 0.1 to 7.5 milligrams of the second anticoagulant, per kilogram of patient body weight. For a tablet dosage form, the compounds of this invention generally may be present in an amount of about 5 to 100 milligrams per dosage unit, and the second anti-coagulant in an amount of about 1 to 50 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (II):

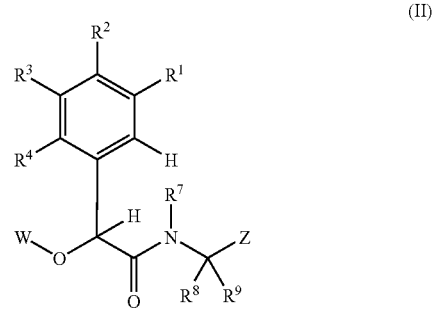

or stereoisomers, tautomers, or pharmaceutically acceptable salts thereof, wherein:

W is substituted with 0-2 $R^6$ and selected from:

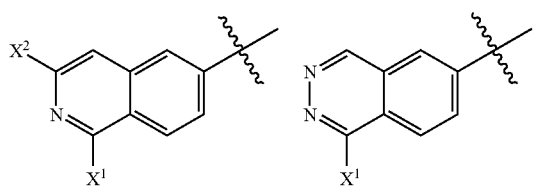

-continued

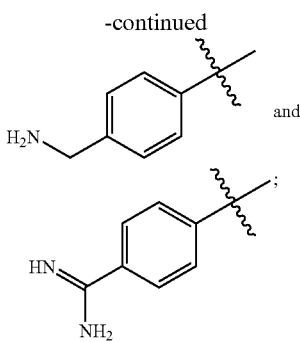
and

X¹ and X² are, independently at each occurrence, H or NH₂;

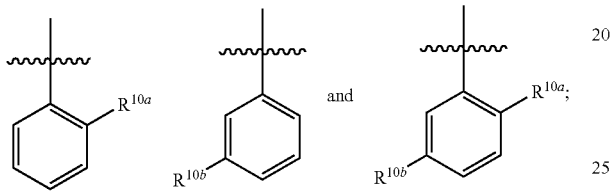

Z is selected from:
R¹ is H, F, Cl, Br, $C_{1-3}$ alkyl substituted with 0-1 OH, $C_{1-3}$ haloalkyl, $C_{2-3}$ alkenyl, $C_{2-3}$ alkynyl, —O—$C_{1-3}$ alkyl, or $C_{3-6}$ cycloalkyl;

R² and R³ are, independently at each occurrence, H, F, Cl, Br, I, OR$^a$, SR$^a$, OCF₃, OCHF₂, OCH₂F, CN, NO₂, —NR$^b$R$^c$, —C(O)R$^a$, —CO₂R$^a$, —NR$^d$C(O)R$^a$, —C(O)NR$^c$R$^d$, —NR$^c$C(O)OR$^a$, —NR$^c$C(O)NR$^c$R$^d$, —SO₂NR$^c$R$^d$, —NR$^c$SO₂NR$^c$R$^d$, —NR$^c$SO₂R$^i$, —NR$^c$SO₂CF₃, —SO₂CF₃, —S(O)$_p$R$^i$, —(CF₂)$_r$CF₃, $C_{1-4}$ alkyl substituted with 0-2 R$^e$, $C_{2-4}$ alkenyl substituted with 0-2 R$^e$, or $C_{2-4}$ alkynyl substituted with 0-2 R$^e$;

R⁴ is, independently at each occurrence, H, F, Cl, Br, I, OR$^a$, SR$^a$, OCF₃, CN, NO₂, —NR$^b$R$^c$, —C(O)R$^a$, —CO₂R$^a$, —NR$^d$C(O)R$^a$, —C(O)NR$^c$R$^d$, —NR$^c$C(O)OR$^a$, —NR$^c$C(O)NR$^c$R$^d$, —SO₂NR$^c$R$^d$, —NR$^c$SO₂NR$^c$R$^d$, —NR$^c$SO₂R$^i$, —NR$^c$SO₂CF₃, —SO₂CF₃, —S(O)$_p$R$^i$, —(CF₂)$_r$CF₃, $C_{1-4}$ alkyl substituted with 0-2 R$^e$, $C_{2-4}$ alkenyl substituted with 0-2 R$^e$, or $C_{2-4}$ alkynyl substituted with 0-2 R$^e$;

R⁶ is, independently at each occurrence, F, Cl, CH₃, OH or CF₃;

R⁷ is H, $C_{1-4}$ alkyl, —CH₂CO₂R$^a$, —CH₂CH₂CO₂R$^a$, —CH₂CH₂OH, —CH₂CH₂CH₂OH, tetrazolyl, —CH₂CONHSO₂R$^e$, or —CH₂CH₂CONHSO₂R$^e$;

R⁸ is H, $C_{1-4}$ alkyl, CO₂R$^a$, —CH₂CO₂R$^a$, —CH₂OH, —CH₂CH₂OH, tetrazolyl, —CONHSO₂R$^e$, or —CH₂CONHSO₂R$^e$;

R⁹ is H or Me;

R$^{10a}$ and R$^{10b}$ are, independently at each occurrence, H, F, Cl, Br, I, SR$^a$, SCF₃, CN, NO₂, —B(OH)₂, —C(O)R$^a$, —(CH₂)$_r$—CO₂R$^a$, —(CH₂)$_r$—NR$^c$CO₂R$^a$, —NR$^d$C(O)R$^a$, —(CH₂)$_r$—C(O)NR$^c$R$^d$, —NR$^c$C(O)NR$^c$R$^d$, —SO₂NR$^c$R$^d$, —OSO₂NR$^c$R$^d$, —NR$^c$SO₂NR$^c$R$^d$, —NR$^c$SO₂R$^i$, —NR$^c$SO₂CF₃, —SO₂CF₃, —S(O)$_p$R$^i$, —(CF₂)$_r$CF₃, $C_{1-6}$ alkyl substituted with 0-2 R$^e$, $C_{2-6}$ alkenyl substituted with 0-2 R$^e$, or $C_{2-6}$ alkynyl substituted with 0-2 R$^e$;

R$^a$ is, independently at each occurrence, H, $C_{1-6}$ alkyl substituted with 0-4 R$^h$, —(CH₂), $C_{3-7}$ carbocycle substituted with 0-4 R$^f$, or —(CH₂),-5- to 10-membered heterocycle comprising: carbon atoms and 1-4 heteroatoms selected from N, NR$^g$, O, and S(O)$_p$, wherein said heteroaryl is substituted with 0-4 R$^f$;

R$^b$ is, independently at each occurrence, H, $C_{1-6}$ alkyl, —(CH₂)$_n$-phenyl, ($C_{1-6}$ alkyl)C(O)—, ($C_{3-6}$ cycloalkyl)-$C_{0-4}$ alkyl-C(O)—, ($C_{6-10}$ aryl)-$C_{0-4}$ alkyl)-C(O)—, (5- to 10-membered heteroaryl)-$C_{0-4}$ alkyl-C(O)—, ($C_{1-6}$ alkyl)-NHC(O)—, ($C_{1-6}$ alkyl)₂-NHC(O)—, ($C_{6-10}$ aryl)-$C_{0-4}$ alkyl-NHC(O)—, (5- to 10-membered heteroaryl)-$C_{0-4}$ alkyl-NHC(O)—, ($C_{1-6}$ alkyl)-SO₂—, ($C_{6-10}$ aryl)-$C_{0-4}$ alkyl-SO₂—, or (5- to 10-membered heteroaryl)-$C_{0-4}$ alkyl-SO₂—, wherein said phenyl, aryl and heteroaryl are substituted with 0-2 R$^f$;

R$^c$ is, independently at each occurrence, H, $C_{1-6}$ alkyl substituted with 0-3 R$^h$, —(CH₂)$_n$—$C_{3-7}$ cycloalkyl substituted with 0-3 R$^h$, or —(CH₂)$_n$-phenyl substituted with 0-3 R$^h$;

R$^d$ is, independently at each occurrence, H, $C_{1-6}$ alkyl, —(CH₂)$_r$—$C_{3-10}$ carbocycle substituted with 0-3 R$^f$, or a —(CH₂)$_r$-5- to 12-membered heterocycle comprising: carbon atoms and 1-4 heteroatoms selected from N, NR$^g$, O, and S(O)$_p$, wherein said heterocycle is substituted with 0-3 R$^f$;

R$^e$ is, independently at each occurrence, =O, OR$^a$, F, Cl, Br, I, CN, NO₂, —SR$^a$, —OCF₃, —NR$^b$R$^c$, —C(O)R$^a$, —CO₂R$^a$, —NR$^d$C(O)R$^a$, —C(O)NR$^c$R$^d$, —OC(O)R$^a$, —NR$^d$C(O)OR$^a$, —NR$^d$C(O)NR$^c$R$^d$, —OC(O)NR$^c$R$^d$, —SO₂NR$^c$R$^d$, —NC(O)OR$^a$, —NR$^c$SO₂NR$^c$R$^d$, —NR$^c$SO₂R$^i$, —NR$^c$SO₂CF₃, —SO₂CF₃, —S(O)$_p$R$^i$, —(CF₂)$_r$CF₃, $C_{3-10}$ carbocycle substituted with 0-3 R$^f$, or a 5- to 12-membered heterocycle comprising: carbon atoms and 1-4 heteroatoms selected from N, NR$^g$, O, and S(O)$_p$, wherein said heterocycle is substituted with 0-3 R$^f$;

R$^f$ is, independently at each occurrence, =O, ORE, F, Cl, Br, I, CN, NO₂, —SR$^g$, —OCF₃, —NR$^c$R$^c$, —C(O)R$^g$, —CO₂R$^g$, —NR$^c$C(O)R$^g$, —C(O)NR$^c$R$^c$, —OC(O)R$^g$, —NR$^c$C(O)OR$^g$, —NR$^c$C(O)NR$^c$R$^c$, —OC(O)NR$^c$R$^c$, —SO₂NR$^c$R$^c$, —NR$^c$SO₂NR$^c$R$^c$, —NR$^c$SO₂R$^i$, —NR$^c$SO₂CF₃, —SO₂CF₃, —S(O)$_p$R$^i$, —(CF₂)$_r$CF₃, $C_{1-6}$ alkyl, $C_{2-6}$ alkenyl, $C_{2-6}$ alkynyl, $C_{3-10}$ carbocycle substituted with 0-3 R$^h$, or a 5- to 12-membered heterocycle comprising: carbon atoms and 1-4 heteroatoms selected from N, NR$^g$, O, and S(O)$_p$, and substituted with 0-3 R$^h$;

R$^g$ is, independently at each occurrence, H, $C_{1-6}$ alkyl, or —(CH₂)$_n$-phenyl;

R$^h$ is, independently at each occurrence, =O, —(CH₂)$_r$OR$^g$, F, Cl, Br, I, CN, NO₂, —OCF₃, —NR$^g$R$^g$, —C(O)R$^g$, —CO₂R$^g$, —NR$^g$C(O)R$^g$, —C(O)NR$^g$R$^g$, —SO₂NR$^g$R$^g$, —NR$^g$SO₂NR$^g$R$^g$, —NR$^g$SO₂—$C_{1-4}$ alkyl, —NR$^g$SO₂CF₃, —NR$^g$SO₂-phenyl, —SO₂CF₃, —S(O)$_p$—$C_{1-4}$ alkyl, —S(O)$_p$-phenyl, —(CF₂)$_r$CF₃, $C_{1-6}$ alkyl, $C_{2-6}$ alkenyl, $C_{2-6}$ alkynyl, ($C_{1-6}$ alkyl)C(O)—, ($C_{3-6}$ cycloalkyl)-$C_{0-4}$ alkyl-C(O)—, ($C_{6-10}$ aryl)-$C_{0-4}$ alkyl)-C(O)—, (5-10 membered heteroaryl)-$C_{0-4}$ alkyl-C(O)—, ($C_{1-6}$ alkyl)-NHC(O)—, ($C_{1-6}$ alkyl)₂-NHC(O)—, ($C_{6-10}$ aryl)-$C_{0-4}$ alkyl-NHC(O)—, (5-10 membered heteroaryl)-$C_{0-4}$ alkyl-NHC(O)—, ($C_{1-6}$ alkyl)-SO₂—, ($C_{6-10}$ aryl)-$C_{0-4}$ alkyl-SO₂—, (5-10 membered heteroaryl)-$C_{0-4}$ alkyl-SO₂—, —(CH$_2$)$_r$—C$_{3-10}$ carbocycle, or a —(CH$_2$)$_r$-5- to 12-membered heterocycle comprising:
carbon atoms and 1-4 heteroatoms selected from N, NR$^g$, O, and S(O)$_p$;
R$^i$ is, independently at each occurrence, H, C$_{1-6}$ alkyl substituted with 0-3 R$^h$, C$_{3-6}$ cycloalkyl substituted with 0-3 R$^h$, —(CH$_2$)$_n$-phenyl substituted with 0-3 R$^h$, —(CH$_2$)$_r$-5-to 10-membered heterocycle comprising: carbon atoms and 1-4 heteroatoms selected from N, NR$^g$, O, and S(O)$_p$, wherein said heterocycle is substituted with 0-3 R$^h$;
n, at each occurrence, is selected from 0, 1, 2, 3, and 4;
p, at each occurrence, is selected from 0, 1, and 2; and
r, at each occurrence, is selected from 0, 1, 2, 3, and 4.

2. A compound according to claim 1, wherein the compound is of Formula (II) or stereoisomers, tautomers, or pharmaceutically acceptable salts thereof, wherein:
W is substituted with 0-1 R$^6$ and selected from:

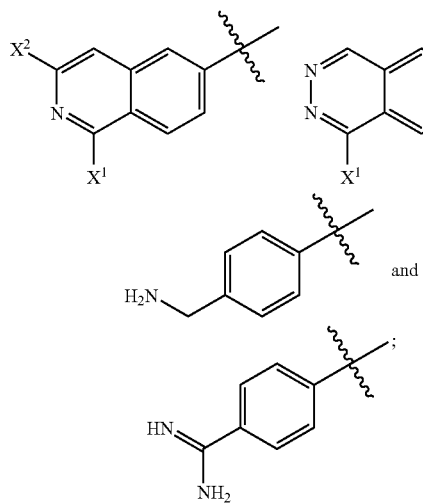

R$^1$ is H, F, Cl, Br, Me, Et, vinyl, 2-propenyl, ethynyl, —CH(OH)Me, OMe, OEt, or cyclopropyl;
R$^2$ and R$^3$ are, independently at each occurrence, H, F, Cl, Br, I, OR$^a$, SR$^a$, OCF$_3$, CN, NO$_2$, —NR$^b$R$^c$, —C(O)R$^a$, —CO$_2$R$^a$, —NR$^d$C(O)R$^a$, —C(O)NR$^c$R$^d$, —SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-4}$ alkyl substituted with 0-2 R$^e$, C$_{2-4}$ alkenyl substituted with 0-2 R$^e$, or C$_{2-6}$ alkynyl substituted with 0-2 R$^e$;
R$^4$ is, independently at each occurrence, H, F, Cl, Br, I, OR$^a$, SR$^a$, OCF$_3$, CN, NO$_2$, —NR$^h$R$^c$, —C(O)R$^a$, —CO$_2$R$^a$, —NR$^d$C(O)R$^a$, —C(O)NR$^c$R$^d$, —SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-4}$ alkyl substituted with 0-2 R$^e$, C$_{2-4}$ alkenyl substituted with 0-2 R$^e$, or C$_{2-4}$ alkynyl substituted with 0-2 R$^e$;
R$^a$ is, independently at each occurrence, H, C$_{1-6}$ alkyl substituted with 0-2 R$^h$, —(CH$_2$)$_r$—C$_{3-6}$ cycloalkyl substituted with 0-2 R$^f$, —(CH$_2$)-phenyl substituted with 0-3 R$^f$, or —(CH$_2$)$_r$-5- to 6-membered heterocycle comprising: carbon atoms and 1-4 heteroatoms selected from N, NR$^g$, O, and S(O)$_p$, wherein said heteroaryl is substituted with 0-3 R$^f$;
R$^b$ is, independently at each occurrence, H, C$_{1-6}$ alkyl, —(CH$_2$)$_n$-phenyl, (C$_{1-6}$ alkyl)C(O)—, (C$_{3-6}$ cycloalkyl)-C$_{0-4}$ alkyl-C(O)—, phenyl-(C$_{0-4}$ alkyl)-C(O)—,
(5- to 6-membered heteroaryl)-C$_{0-4}$ alkyl-C(O)—, (C$_{1-6}$ alkyl)-NHC(O)—,
(C$_{1-6}$ alkyl)$_2$-NHC(O)—, phenyl-C$_{0-4}$ alkyl-NHC(O)—,
(5- to 6-membered heteroaryl)-C$_{0-4}$ alkyl-NHC(O)—, (C$_{1-6}$ alkyl)-SO$_2$—,
phenyl-C$_{0-4}$ alkyl-SO$_2$—, or (5- to 6-membered heteroaryl)-C$_{0-4}$ alkyl-SO$_2$—, wherein said phenyl and heteroaryl are substituted with 0-2 R$^f$;
R$^c$ is, independently at each occurrence, H, C$_{1-6}$ alkyl substituted with 0-3 R$^h$, —(CH$_2$)$_n$—C$_{3-6}$ cycloalkyl substituted with 0-2 R$^h$, or —(CH$_2$)$_n$-phenyl substituted with 0-3 R$^h$;
R$^d$ is, independently at each occurrence, H, C$_{1-6}$ alkyl, —(CH$_2$)$_n$—C$_{3-6}$ cycloalkyl substituted with 0-2 R$^f$, —(CH$_2$)$_r$-phenyl substituted with 0-3 R$^f$, or a —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-3 R$^f$;
R$^e$ is, independently at each occurrence, =O, OR$^a$, F, Cl, Br, I, CN, NO$_2$, —SR$^a$, —OCF$_3$, —NR$^c$R$^c$, —C(O)R$^a$, —CO$_2$R$^a$, —NR$^d$C(O)R$^a$, —C(O)NR$^c$R$^d$, —OC(O)R$^a$, —NR$^d$C(O)OR$^a$, —NR$^d$C(O)NRCR$^d$, —OC(O)NR$^c$R$^d$, —SO$_2$NR$^c$R$^d$, —NC(O)OR$^a$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{3-6}$ cycloalkyl substituted with 0-2 R$^f$, phenyl substituted with 0-3 R$^f$, or a 5- to 10-membered heterocycle comprising: carbon atoms and 1-4 heteroatoms selected from N, NR$^g$, O, and S(O)$_p$, wherein said heterocycle is substituted with 0-3 R$^f$;
R$^f$ is, independently at each occurrence, =O, OR$^g$, F, Cl, Br, I, CN, NO$_2$, —SR$^g$, —OCF$_3$, —NR$^c$R$^c$, —C(O)R$^g$, —CO$_2$R$^g$, —NR$^c$C(O)R$^g$, —C(O)NR$^c$R$^c$, —OC(O)R$^g$, —NR$^c$C(O)OR$^g$, —NR$^c$C(O)NR$^c$R$^c$, —OC(O)NR$^c$R$^c$, —SO$_2$NR$^c$R$^c$, —NR$^c$SO$_2$NR$^c$R$^c$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl, C$_{2-6}$ alkenyl, C$_{2-6}$ alkynyl, C$_{3-6}$ cycloalkyl substituted with 0-2 R$^f$, phenyl substituted with 0-3 R$^f$, or a 5- to 10-membered heterocycle comprising: carbon atoms and 1-4 heteroatoms selected from N, NR$^g$, O, and S(O)$_p$, and substituted with 0-3 R$^h$;
R$^h$ is, independently, at each occurrence, =O, —(CH$_2$)$_r$OR$^g$, F, Cl, Br, I, CN, NO$_2$, —OCF$_3$, —NR$^g$R$^g$, —C(O)R$^g$, —CO$_2$R$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —SO$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$ alkyl)-C(O)—,
(5-10 membered heteroaryl)-C$_{0-4}$ alkyl-C(O)—, (C$_{1-6}$ alkyl)-NHC(O)—, (C$_{1-6}$ alkyl)$_2$-NHC(O)—, (C$_{6-10}$ aryl)-C$_{0-4}$ alkyl-NHC(O)—, (5-10 membered heteroaryl)-C$_{0-4}$ alkyl-NHC(O)—,
(C$_{1-6}$ alkyl)-SO$_2$—, (C$_{6-10}$ aryl)-C$_{0-4}$ alkyl-SO$_2$—, (5-10 membered heteroaryl)-C$_{0-4}$ alkyl-SO$_2$—, C$_{3-6}$ cycloalkyl, phenyl, or a —(CH$_2$)$_r$-5- to 10-membered heterocycle comprising:
carbon atoms and 1-4 heteroatoms selected from N, NR$^g$, O, and S(O)$_p$; and
R$^i$ is, independently at each occurrence, H, C$_{1-6}$ alkyl substituted with 0-3 R$^h$, C$_{3-6}$ cycloalkyl substituted with 0-3 R$^h$, —(CH$_2$)$_n$-phenyl substituted with 0-3 R$^h$, —(CH$_2$)$_r$-5- to 6-membered heterocycle comprising:

carbon atoms and 1-4 heteroatoms selected from N, $NR^g$, O, and $S(O)_p$, wherein said heterocycle is substituted with 0-3 $R^h$.

3. A compound according to claim 2, wherein the compound is of Formula (II) or stereoisomers, tautomers, or pharmaceutically acceptable salts thereof, wherein:
W is substituted with 0-1 $R^6$ and selected from:

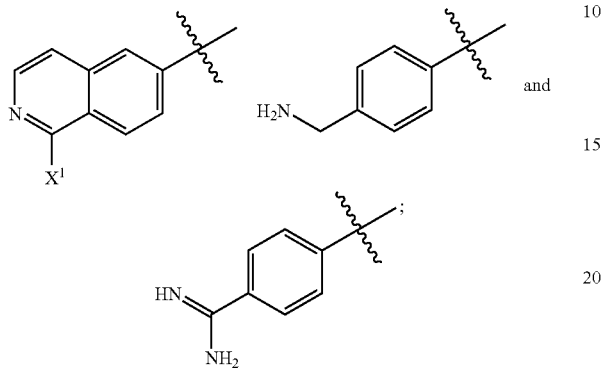

and $R^1$ is H, F, Cl, Br, Me, Et, vinyl, 2-propenyl, ethynyl, —CH(OH)Me, OMe, OEt, or cyclopropyl;
$R^2$ is H, F, Cl, Me, Et, OMe, O(i-Pr), or —OCHF$_2$;
$R^3$ is H, OMe, or OEt;
$R^4$ is H or F;
$R^7$ is H, $C_{1-4}$ alkyl, or —CH$_2$CO$_2$R$^a$;
$R^8$ is H or $C_{1-4}$ alkyl;
$R^9$ is H; and
$R^{10a}$ and $R^{10b}$ are, independently at each occurrence, H, $C_{1-4}$alkyl, F, Cl, —SC$_{1-4}$ alkyl, CF$_3$, SCF$_3$, CO$_2$Me, CONH$_2$, —NHCOH, —NHCOMe, —NHCOEt, —NHCOPr, —NHCO(i-Pr), —NHCO(i-Bu), —NHCO-cyclopropyl,—N(Me)COMe,—NHCO$_2$Me, NHCO$_2$Et, —NHCONH$_2$, —NHCONHMe, —NHCONMe$_2$, —NHCON(Me)Et, 4-F-Ph, NO$_2$, NHCON (Me)(i-Pr), —NHCO-(1-azetidinyl), —NHCO-(1-pyrrolidinyl), —NHCO-(3-thiazolidinyl), —SO$_2$Me, —SO$_2$Et, —SO$_2$Pr, —SO$_2$(i-Pr), —SO$_2$(i-Bu), —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$-(4-morpholinyl), —SO$_2$-(4-thiamorpholinyl), —SO$_2$— (4-Me-1-piperazinyl), —SO$_2$NH$_2$, —SO$_2$NHMe, —SO$_2$NHEt, —SO$_2$NH(i-Pr),—SO$_2$NH-cyclopropyl,—SO$_2$NH-cyclohexyl, —SO$_2$NH(t-Bu), —SO$_2$N(Me)Bn, —SO$_2$NMe$_2$, —OSO$_2$NH$_2$, —NHSO$_2$NH$_2$, —NHSO$_2$Me, Ph, or —B(OH)$_2$.

4. A compound according to claim 3, wherein the compound of Formula (II) or stereoisomers, tautomers, or pharmaceutically acceptable salts thereof, wherein:
$R^1$ is OMe or OEt;
$R^2$ is OMe or O(i-Pr);
$R^3$ is H;
$R^4$ is H or F;
$R^7$ is H or Me;
$R^8$ is H;
$R^9$ is H;
$R^{10a}$ is, independently at each occurrence, H, —SO$_2$—C$_{1-4}$ alkyl, —SO$_2$-cyclopropyl, —SO$_2$-cyclobutyl, or 3,5-diethyl-1H-pyrazol-1-yl; and
$R^{10b}$ is, independently at each occurrence, H, —NHCOMe, —NHCOEt, —NHCO$_2$Me, or —NHCO$_2$Et.

5. A compound according to claim 1, wherein the compound is of Formula (III):

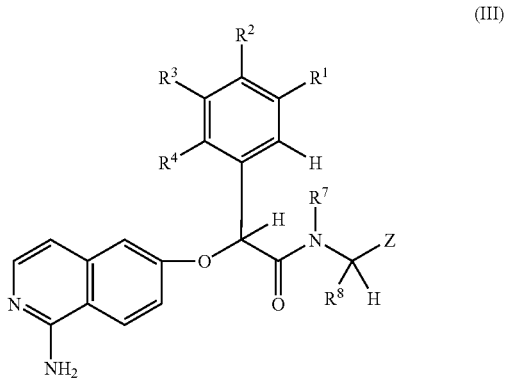

or stereoisomers, tautomers, or pharmaceutically acceptable salts thereof, wherein:

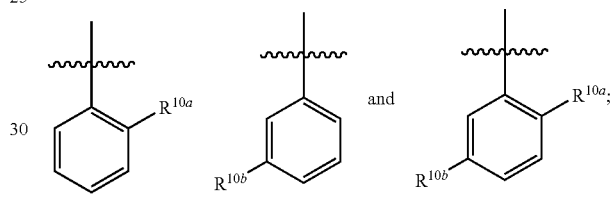

Z is selected from:

$R^1$ is H, F, Cl, Br, Me, Et, vinyl, 2-propenyl, ethynyl, —CH(OH)Me, OMe, OEt, or cyclopropyl;
$R^2$ is H, F, Cl, Me, Et, OMe, O(i-Pr), or —OCHF$_2$;
$R^3$ is H, OMe, or OEt;
$R^4$ is H or F;
$R^7$ is H, $C_{1-4}$ alkyl, or —CH$_2$CO$_2$R$^a$;
$R^8$ is H or $C_{1-4}$ alkyl; and
$R^{10a}$ and $R^{10b}$ are, independently at each occurrence, H, $C_{1-4}$ alkyl, F, Cl, —S—C$_{1-4}$ alkyl, CF$_3$, SCF$_3$, CO$_2$Me, CONH$_2$, —NHCOH, —NHCOMe, —NHCOEt, —NHCOPr, —NHCO(i-Pr), —NHCO(i-Bu), —NHCO-cyclopropyl, —N(Me)COMe, —NHCO$_2$Me, —NHCO$_2$Et, —NHCONH$_2$, —NHCONHMe, —NHCONMe$_2$, —NHCON(Me)Et, —NHCON(Me)(i-Pr), —NHCO-(1-azetidinyl), —NHCO-(1-pyrrolidinyl), —NHCO-(3-thiazolidinyl), —SO$_2$Me, —SO$_2$Et, —SO$_2$Pr, —SO$_2$(i-Pr), —SO$_2$(i-Bu), —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$-(4-morpholinyl), —SO$_2$-(4-thiamorpholinyl), —SO$_2$— (4-Me-1-piperazinyl), —SO$_2$NH$_2$, —SO$_2$NHMe, —SO$_2$NHEt, —SO$_2$NH(i-Pr), —SO$_2$NH-cyclopropyl, —SO$_2$NH-cyclohexyl, —SO$_2$NH(t-Bu), —SO$_2$N(Me)Bn, —SO$_2$NMe$_2$, —OSO$_2$NH$_2$, —NHSO$_2$NH$_2$, —NHSO$_2$Me, Ph, 4-F-Ph, NO$_2$, or —B(OH)$_2$.

6. A compound according to claim 5, wherein the compound is of Formula (III) or stereoisomers, tautomers, or pharmaceutically acceptable salts thereof, wherein:
$R^1$ is H, F, Cl, Me, Et, OMe, or OEt;
$R^8$ is H;
$R^{10a}$ is, independently at each occurrence, H, —$SO_2$—$C_{1-4}$ alkyl, —$SO_2$-cyclopropyl, —$SO_2$-cyclobutyl, —$SO_2$-cyclopentyl, —$SO_2$Ph, —$SO_2$-(1-pyrrolidinyl), —$SO_2$-(1-piperidyl), —$SO_2$-(1-azepanyl), —$SO_2NH$—$C_{1-4}$ alkyl, —$SO_2NH$-cyclopropyl, —$SO_2NMe_2$, $CONMe_2$, CO(1-pyrrolidinyl), CO(1-piperidinyl), 1-piperidyl, 4-morpholinyl, or 3,5-diethyl-1H-pyrazol-1-yl; and
$R^{10b}$ is, independently at each occurrence, H, —NHCOH, —NHCOMe, —NHCOEt, —$NHCO_2$Me, —$NHCO_2$Et, —NHCONHMe, —$NHCONH_2$, —$NHCONMe_2$, —NHCON(Me)Et, —NHCON(Me)(i-Pr), —NHCO-(1-azetidinyl), —NHCO-(1-pyrrolidinyl), —NHCO-(3-thiazolidinyl), —$OSO_2NH_2$, —$NHSO_2NH_2$, —$NHSO_2$Me, —$SO_2NH_2$, or $NO_2$.

7. A compound according to claim 5, wherein the compound is of Formula (III) or stereoisomers, tautomers, or pharmaceutically acceptable salts thereof, wherein:
$R^7$ is H;
$R^8$ is H;
$R^{10a}$ is, independently at each occurrence, —$SO_2$—$C_{1-4}$ alkyl, —$SO_2$-cyclopropyl, —$SO_2$-cyclobutyl, —$SO_2$-cyclopentyl, —$SO_2$Ph, —$SO_2$-(1-pyrrolidinyl), —$SO_2$-(1-piperidyl), —$SO_2$-(1-azepanyl), —$SO_2NH$—$C_{1-4}$ alkyl, —$SO_2NH$-cyclopropyl, —$SO_2NMe_2$, $CONMe_2$, CO(1-pyrrolidinyl), CO(1-piperidinyl), 1-piperidyl, 4-morpholinyl, or 3,5-diethyl-1H-pyrazol-1-yl; and
$R^{10b}$ is, independently at each occurrence, —NHCOH, —NHCOMe, —NHCOEt, —$NHCO_2$Me, —$NHCO_2$Et, —NHCONHMe, —$NHCONMe_2$, —NHCON(Me)Et, —NHCON(Me)(i-Pr), —NHCO-(1-azetidinyl), —NHCO-(1-pyrrolidinyl), —NHCO-(3-thiazolidinyl), —$NHCONH_2$, —$OSO_2NH_2$, —$NHSO_2NH_2$, —$NHSO_2$Me, or —$SO_2NH_2$.

8. A compound according to claim 5, wherein the compound is of Formula (III) or stereoisomers, tautomers, or pharmaceutically acceptable salts-thereof, wherein:
$R^7$ is H, $C_{1-4}$ alkyl, or —$CH_2CO_2R^a$;
$R^8$ is H;
$R^{10a}$ is, independently at each occurrence, —$SO_2$—$C_{1-4}$ alkyl, —$SO_2$-cyclopropyl, —$SO_2$-cyclobutyl, —$SO_2$-cyclopentyl, —$SO_2$Ph, —$SO_2$-(1-pyrrolidinyl), —$SO_2$-(1-piperidyl), —$SO_2$-(1-azepanyl), —$SO_2NH$—$C_{1-4}$ alkyl, —$SO_2NH$-cyclopropyl, —$SO_2NMe_2$, $CONMe_2$, CO(1-pyrrolidinyl), CO(1-piperidinyl), 1-piperidyl, or 4-morpholinyl, or 3,5-diethyl-1H-pyrazol-1-yl; and
$R^{10b}$ is H.

9. A compound according to claim 5, wherein the compound is of Formula (III) or stereoisomers, tautomers, or pharmaceutically acceptable salts-thereof, wherein:
$R^7$ is H, $C_{1-4}$ alkyl, or —$CH_2CO_2R^a$;
$R^8$ is H;
$R^{10a}$ is, independently at each occurrence, —$SO_2$—$C_{1-4}$ alkyl, —$SO_2$-cyclopropyl, —$SO_2$-cyclobutyl, —$SO_2$-cyclopentyl, —$SO_2$Ph, —$SO_2$-(1-pyrrolidinyl), —$SO_2$-(1-piperidyl), —$SO_2$-(1-azepanyl), —$SO_2NH$—$C_{1-4}$ alkyl, —$SO_2NH$-cyclopropyl, —$SO_2NMe_2$, $CONMe_2$, CO(1-pyrrolidinyl), CO(1-piperidinyl), 1-piperidyl, 4-morpholinyl, or 3,5-diethyl-1H-pyrazol-1-yl; and
$R^{10b}$ is, independently at each occurrence, —NHCOH, —NHCOMe, —NHCOEt, —$NHCO_2$Me, —$NHCO_2$Et, —NHCONHMe, —$NHCONMe_2$, —NHCON(Me)Et, —NHCON(Me)(i-Pr), —NHCO-(1-azetidinyl), —NHCO-(1-pyrrolidinyl), —NHCO-(3-thiazolidinyl), —$NHCONH_2$, —$OSO_2NH_2$, —$NHSO_2NH_2$, —$NHSO_2$Me, or —$SO_2NH_2$.

10. A compound according to claim 5, wherein the compound is of Formula (III) or stereoisomers, tautomers, or pharmaceutically acceptable salts-thereof, wherein:
$R^7$ is H, $C_{1-4}$ alkyl, or —$CH_2CO_2R^a$;
$R^8$ is H;
$R^{10a}$ is H.
$R^{10b}$ is, independently at each occurrence, —NHCOH, —NHCOMe, —NHCOEt, —$NHCO_2$Me, —$NHCO_2$Et, —NHCONHMe, —$NHCONMe_2$, —NHCON(Me)Et, —NHCON(Me)(i-Pr), —NHCO-(1-azetidinyl), —NHCO-(1-pyrrolidinyl), —NHCO-(3-thiazolidinyl), —$NHCONH_2$, —$OSO_2NH_2$, —$NHSO_2NH_2$, —$NHSO_2$Me, or —$SO_2NH_2$.

11. A compound according to claim 1, wherein the compound is of Formula (IIa):

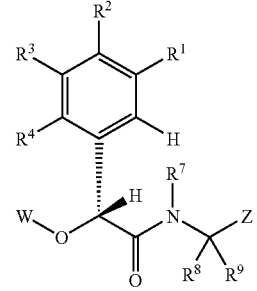

(IIa)

or stereoisomers, tautomers, or pharmaceutically acceptable salts thereof.

12. A compound according to claim 1 wherein the compound is selected from:
N-(2-(cyclopropylsulfonyl)benzyl)-2-(1-aminoisoquinolin-6-yloxy)-2-(3-ethoxy-4-isopropoxyphenyl)-N-methylacetamide;
N-(2-(cyclobutylsulfonyl)benzyl)-2-(1-aminoisoquinolin-6-yloxy)-2-(3-ethoxy-4-isopropoxyphenyl)acetamide;
N-(3-acetylamino-benzyl)-2-(1-aminoisoquinolin-6-yloxy)-2-(3-ethoxy-4-isopropoxy-phenyl)-acetamide;
N-(2-(3,5-diethyl-1H-pyrazol-1-yl)benzyl)-2-(1-aminoisoquinolin-6-yloxy)-2-(3-ethoxy-4-isopropoxyphenyl)acetamide;
N-(5-acetylamino-2-ethanesulfonyl-benzyl)-2-(1-aminoisoquinolin-6-yloxy)-2-(3-ethoxy-4-isopropoxy-phenyl)-acetamide;
N-(5-acetylamino-2-ethanesulfonyl-benzyl)-2-(1-aminoisoquinolin-6-yloxy)-2-(3,4-dimethoxy-phenyl)-acetamide;
N-(5-acetylamino-2-ethanesulfonyl-benzyl)-2-(1-aminoisoquinolin-6-yloxy)-2-(2-fluoro-4,5-dimethoxy-phenyl)-acetamide;
methyl 3-((2-(1-aminoisoquinolin-6-yloxy)-2-(3,4-dimethoxyphenyl)-acetamido)methyl)-4-isopropoxyphenylcarbamate;
N-(3-acetylamino-benzyl)-2-(4-carbamimidoyl-phenoxy)-2-(3-ethoxy-4-isopropoxy-phenyl)-acetamide;
N-benzyl-2-(4-carbamimidoylphenoxy)-2-(3-ethoxy-4-isopropoxyphenyl)acetamide;
N-(2-(cyclopropylsulfonyl)benzyl)-2-(4-carbamimidoylphenoxy)-2-(3-ethoxy-4-isopropoxyphenyl)acetamide;

N-(5-acetylamino-2-ethanesulfonyl-benzyl)-2-(4-carbamimidoyl-phenoxy)-2-(3-ethoxy-4-isopropoxy-phenyl)-acetamide;

N-(3-acetylamino-benzyl)-2-(4-aminomethyl-phenoxy)-2-(3-ethoxy-4-isopropoxy-phenyl)-acetamide;

N-(5-acetylamino-2-ethanesulfonyl-benzyl)-2-(4-aminomethyl-phenoxy)-2-(3-ethoxy-4-isopropoxy-phenyl)-acetamide;

methyl 3-((2-(1-aminoisoquinolin-6-yloxy)-2-(3,4-dimethoxyphenyl)acetamido)methyl)-4-(isopropylsulfonyl)phenylcarbamate; and 3-(3-((2-(1-aminoisoquinolin-6-yloxy)-2-(3,4-dimethoxyphenyl)acetamido)methyl)-4-(isopropylsulfonyl)phenyl)-1,1-dimethylurea;

or stereoisomers, tautomers, or pharmaceutically acceptable salts thereof.

13. A pharmaceutical composition, comprising: a pharmaceutically acceptable carrier and a compound of claim 1 or stereoisomers, tautomers, or pharmaceutically acceptable salts thereof.

14. A pharmaceutical composition, comprising: a pharmaceutically acceptable carrier and a compound of claim 3 or stereoisomers, tautomers, or pharmaceutically acceptable salts hereof.

15. A pharmaceutical composition, comprising: a pharmaceutically acceptable carrier and a compound of claim 5 or stereoisomers, tautomers, or pharmaceutically acceptable salts thereof.

16. A pharmaceutical composition, comprising: a pharmaceutically acceptable carrier and a compound of claim 11 or stereoisomers, tautomers, or pharmaceutically acceptable salts thereof.

17. A pharmaceutical composition, comprising: a pharmaceutically acceptable carrier and a compound of claim 12 or stereoisomers, tautomers, or pharmaceutically acceptable salts thereof.

* * * * *

UNITED STATES PATENT AND TRADEMARK OFFICE
CERTIFICATE OF CORRECTION

PATENT NO. : 8,044,242 B2  Page 1 of 1
APPLICATION NO. : 12/282178
DATED : October 25, 2011
INVENTOR(S) : Alexandra A. Nirschl and Xiaojun Zhang It is certified that error appears in the above-identified patent and that said Letters Patent is hereby corrected as shown below:

Column 84
Line 2, "—(CH$_2$), C$_{3-7}$" should read -- —(CH$_2$)$_r$–C$_{3-7}$ --;
Line 3, "—(CH$_2$),-5-" should read -- —(CH$_2$)$_r$-5- --; and
Line 40, "OR$^E$," should read -- OR$^g$, --.

Column 85
Line 53, "—NR$^h$R$^c$," should read -- —NR$^b$R$^c$, --.

Column 86
Line 23, "—NR$^c$R$^c$," should read -- —NR$^b$R$^c$, --;
Line 25, "—NR$^d$C(O)NRCR$^d$," should read -- —NR$^d$C(O)NR$^c$R$^d$, --; and
Line 26, "—SO 2NR$^c$R$^d$," should read -- —SO$_2$NR$^c$R$^d$, --.

Column 87

Line 10-16, 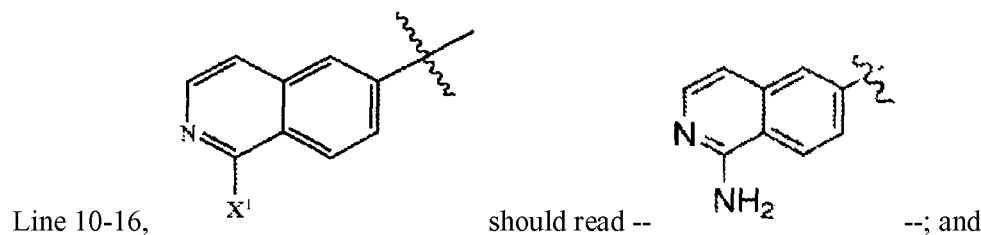 should read -- --; and

Line 35, "C$_{1-h}$alkyl," should read -- C$_{1-4}$ alkyl, --.

Column 90
Line 9, "H." should read -- H; --; and
Line 19, "(Ha):" should read -- (IIa): --.

Signed and Sealed this
Tenth Day of January, 2012

David J. Kappos
*Director of the United States Patent and Trademark Office*